US012570744B2

(12) United States Patent
Mazor et al.

(10) Patent No.: US 12,570,744 B2
(45) Date of Patent: *Mar. 10, 2026

(54) BISPECIFIC PD-1 AND TIGIT BINDING PROTEINS AND USES THEREOF

(71) Applicant: MedImmune, LLC, Gaithersburg, MD (US)

(72) Inventors: Yariv Mazor, Gaithersburg, MD (US); Yue Wang, Gaithersburg, MD (US); Gordon Moody, Gaithersburg, MD (US); Deepali Malhotra, Gaithersburg, MD (US); Michael Overstreet, Gaithersburg, MD (US); Eleanor Clancy-Thompson, Giathersburg, MD (US); Karin Lee, Gaithersburg, MD (US); Stacy Pryts, Gaithersburg, MD (US); Scott Hammond, Gaithersburg, MD (US)

(73) Assignee: MedImmune, LLC

( * ) Notice: Subject to any disclaimer, the term of this patent is extended or adjusted under 35 U.S.C. 154(b) by 0 days.

This patent is subject to a terminal disclaimer.

(21) Appl. No.: 18/441,469

(22) Filed: Feb. 14, 2024

(65) Prior Publication Data

US 2024/0287183 A1 Aug. 29, 2024

Related U.S. Application Data

(63) Continuation of application No. 17/661,307, filed on Apr. 29, 2022, now Pat. No. 11,939,382.

(60) Provisional application No. 63/182,156, filed on Apr. 30, 2021.

(51) Int. Cl.
| | |
|---|---|
| *A61K 45/06* | (2006.01) |
| *A61K 39/395* | (2006.01) |
| *A61P 35/00* | (2006.01) |
| *C07K 16/28* | (2006.01) |
| *A61K 39/00* | (2006.01) |

(52) U.S. Cl.
CPC .... *C07K 16/2818* (2013.01); *A61K 39/39558* (2013.01); *A61K 45/06* (2013.01); *A61P 35/00* (2018.01); *C07K 16/2803* (2013.01); *A61K 2039/505* (2013.01); *C07K 2317/31* (2013.01); *C07K 2317/565* (2013.01); *C07K 2317/72* (2013.01); *C07K 2317/76* (2013.01); *C07K 2317/92* (2013.01)

(58) Field of Classification Search
CPC .. C07K 16/2818; C07K 2317/31; A61P 35/00
See application file for complete search history.

(56) References Cited

U.S. PATENT DOCUMENTS

| | | | |
|---|---|---|---|
| 10,124,061 | B2 | 11/2018 | White et al. |
| 10,213,505 | B2 | 2/2019 | White et al. |
| 10,457,732 | B2 | 10/2019 | Kasturirangan et al. |
| 10,751,415 | B2 | 8/2020 | White et al. |
| 11,279,759 | B2 | 3/2022 | Kasturirangan et al. |
| 11,701,424 | B2 | 7/2023 | White et al. |
| 2020/0095328 | A1* | 3/2020 | Foletti ............... C07K 16/2866 |
| 2020/0172622 | A1 | 6/2020 | Kasturirangan et al. |
| 2020/0347135 | A1 | 11/2020 | Zhang et al. |
| 2021/0000952 | A1 | 1/2021 | White et al. |
| 2022/0251204 | A1 | 8/2022 | Kasturirangan et al. |
| 2022/0411509 | A1 | 12/2022 | Mazor et al. |
| 2024/0075137 | A1 | 3/2024 | White et al. |
| 2024/0139318 | A1 | 5/2024 | White et al. |
| 2025/0074986 | A1 | 3/2025 | Morrow et al. |

FOREIGN PATENT DOCUMENTS

| | | |
|---|---|---|
| WO | 2019129221 A1 | 7/2019 |
| WO | 2020242919 A1 | 12/2020 |

OTHER PUBLICATIONS

Chu, X., Tian, W., Wang, Z. et al. Co-inhibition of TIGIT and PD-1/PD-L1 in Cancer Immunotherapy: Mechanisms and Clinical Trials. Mol Cancer 22, 93 (2023). (Year: 2023).*
Int'l Search Report and Written Opinion for PCT/IB2022/053997 mailed Nov. 7, 2022.
Brown M., et al., "Tolerance to Single, But Not Multiple, Amino Acid Replacements in Antibody VH CDR2: A Means of Minimizing B Cell Wastage from Somatic Hypermutation?," Journal of Immunology, American Association of Immunologists, United States, 1996, vol. 156, No. 9, pp. 3285-3291.
Rudikoff S., et al., "Single Amino Acid Substitution Altering Antigen-binding Specificity", Proceedings of the National Academy of Sciences of the United States of America, Mar. 1982, vol. 79, No. 6, pp. 1979-1983.
Supplementary European Search Report in European Patent Application No. 22795127.4, dated Mar. 14, 2025, 10 Pages.

* cited by examiner

*Primary Examiner* — Aurora M Fontainhas
*Assistant Examiner* — Jennifer A Benavides

(57) ABSTRACT

The disclosure relates to binding proteins, including antibodies, that bind to Programmed Death-1 ("PD-1") and T cell immunoreceptor with Ig and ITIM domains ("TIGIT"). The disclosure also provides compositions comprising such binding proteins and nucleic acid molecules encoding such binding proteins. The disclosure further relates to methods of treating a disorder or condition using such binding proteins.

20 Claims, 33 Drawing Sheets

Specification includes a Sequence Listing.

| Sample ID | KD (M) | KD Error | kon(1/Ms) | kon Error | kdis(1/s) | kdis Error | Full X^2 | Full R^2 |
|---|---|---|---|---|---|---|---|---|
| VL WT + VH WT | 2.27E-10 | 1.28E-11 | 2.19E+05 | 9.67E+02 | 4.96E-05 | 2.78E-06 | 0.115366 | 0.999806 |
| VL GL + VH WT | 4.33E-10 | 1.62E-11 | 2.36E+05 | 1.79E+03 | 1.02E-04 | 3.75E-06 | 0.084777 | 0.999698 |
| VL WT + VH GL | 1.48E-10 | 1.57E-11 | 2.02E+05 | 1.02E+03 | 2.99E-05 | 3.16E-06 | 0.190935 | 0.99369 |
| VL GL + VH GL | 2.23E-10 | 9.01E-12 | 3.04E+05 | 1.46E+03 | 6.78E-05 | 2.72E-06 | 0.050076 | 0.999837 |
| VL GL (CDRL1 M-I) + VH GL | 2.87E-10 | 1.62E-11 | 2.31E+05 | 1.34E+03 | 6.62E-05 | 3.72E-06 | 0.230532 | 0.999599 |

FIG. 5

OE21 Tumor Growth Inhibition

D148026
24 Hours Post Second Dose

Fold change in tumor volume
from baseline

Isotype Control
Anti-PD-1
AZD2936
TIGIT-PD1 Combination

D198165
24 Hours Post Second Dose

Fold change in tumor volume
from baseline

Isotype Control
Anti-PD-1
AZD2936
TIGIT-PD1 Combination

PC9-MART1 Tumor Growth Inhibition

PC9-MART1 Tumor Growth Inhibition

SEQUENCE LISTING

Sequence total quantity: 40
SEQ ID NO: 1              moltype = AA   length = 5
FEATURE                   Location/Qualifiers
REGION                    1..5
                          note = Synthetic peptide
source                    1..5
                          mol_type = protein
                          organism = synthetic construct
SEQUENCE: 1
DYGMH                                                            5

SEQ ID NO: 2              moltype = AA   length = 17
FEATURE                   Location/Qualifiers
REGION                    1..17
                          note = Synthetic peptide
source                    1..17
                          mol_type = protein
                          organism = synthetic construct
SEQUENCE: 2
YISSGSYTIY SADSVKG                                               17

SEQ ID NO: 3              moltype = AA   length = 13
FEATURE                   Location/Qualifiers
REGION                    1..13
                          note = Synthetic peptide
source                    1..13
                          mol_type = protein
                          organism = synthetic construct
SEQUENCE: 3
RAPNSFYEYY FDY                                                   13

SEQ ID NO: 4              moltype = AA   length = 16
FEATURE                   Location/Qualifiers
REGION                    1..16
                          note = Synthetic peptide
source                    1..16
                          mol_type = protein
                          organism = synthetic construct
SEQUENCE: 4
SASSKHTNLY WSRHMY                                                16

SEQ ID NO: 5              moltype = AA   length = 7
FEATURE                   Location/Qualifiers
REGION                    1..7
                          note = Synthetic peptide
source                    1..7
                          mol_type = protein
                          organism = synthetic construct
SEQUENCE: 5
LTSNRAT                                                          7

SEQ ID NO: 6              moltype = AA   length = 9
FEATURE                   Location/Qualifiers
REGION                    1..9
                          note = Synthetic peptide
source                    1..9
                          mol_type = protein
                          organism = synthetic construct
SEQUENCE: 6
QQWSSNPFT                                                        9

SEQ ID NO: 7              moltype = AA   length = 122
FEATURE                   Location/Qualifiers
REGION                    1..122
                          note = Synthetic peptide
source                    1..122
                          mol_type = protein
                          organism = synthetic construct
SEQUENCE: 7
EVQLVESGGG LVQPGGSLRL SCAASGFTFS DYGMHWVRQA PGKGLEWVAY ISSGSYTIYS  60
ADSVKGRFTI SRDNAKNSLY LQMNSLRAED TAVYYCARRA PNSFYEYYFD YWGQGTTVTV  120
SS                                                               122

SEQ ID NO: 8              moltype = AA   length = 452
FEATURE                   Location/Qualifiers
REGION                    1..452
                          note = Synthetic peptide
source                    1..452

```
                              mol_type = protein
                              organism = synthetic construct
SEQUENCE: 8
EVQLVESGGG LVQPGGSLRL SCAASGFTFS DYGMHWVRQA PGKGLEWVAY ISSGSYTIYS   60
ADSVKGRFTI SRDNAKNSLY LQMNSLRAED TAVYYCARRA PNSFYEYYFD YWGQGTTVTV  120
SSASTKGPSV FPLAPSSKST SGGTAALGCL VKDYFPEPVT VSWNSGALTS GVHTFPAVLQ  180
SSGLYSLSSV VTVPSSSLGT QTYICNVNHK PSNTKVDKRV EPKSCDKTHT CPPCPAPEFE  240
GGPSVFLFPP KPKDTLMISR TPEVTCVVVD VSHEDPEVKF NWYVDGVEVH NAKTKPREEQ  300
YNSTYRVVSV LTVLHQDWLN GKEYKCKVSN KALPASIEKT ISKAKGQPRE PQVCTLPPSR  360
EEMTKNQVSL SCAVKGFYPS DIAVEWESNG QPENNYKTTP PVLDSDGSFF LVSKLTVDKS  420
RWQQGNVFSC SVMHEALHNH YTQKSLSLSP GK                                452

SEQ ID NO: 9                  moltype = AA  length = 112
FEATURE                       Location/Qualifiers
REGION                        1..112
                              note = Synthetic peptide
source                        1..112
                              mol_type = protein
                              organism = synthetic construct
SEQUENCE: 9
QIVLTQSPAT LSLSPGERAT LSCSASSKHT NLYWSRHMYW YQQKPGQAPR LLIYLTSNRA   60
TGIPARFSGS GSGTDFTLTI SSLEPEDFAV YYCQQWSSNP FTFGQGTKLE IK           112

SEQ ID NO: 10                 moltype = AA  length = 219
FEATURE                       Location/Qualifiers
REGION                        1..219
                              note = Synthetic peptide
source                        1..219
                              mol_type = protein
                              organism = synthetic construct
SEQUENCE: 10
QIVLTQSPAT LSLSPGERAT LSCSASSKHT NLYWSRHMYW YQQKPGQAPR LLIYLTSNRA   60
TGIPARFSGS GSGTDFTLTI SSLEPEDFAV YYCQQWSSNP FTFGQGTKLE IKRTVAAPSV  120
FIFPPSDEQL KSGTASVVCL LNNFYPREAK VQWKVDNALQ SGNSQESVTE QDSKDSTYSL  180
SSTLTLSKAD YEKHKVYACE VTHQGLSSPV TKSFNRGEC                         219

SEQ ID NO: 11                 moltype = AA  length = 5
FEATURE                       Location/Qualifiers
REGION                        1..5
                              note = Synthetic peptide
source                        1..5
                              mol_type = protein
                              organism = synthetic construct
SEQUENCE: 11
SYAMH                                                                5

SEQ ID NO: 12                 moltype = AA  length = 17
FEATURE                       Location/Qualifiers
REGION                        1..17
                              note = Synthetic peptide
source                        1..17
                              mol_type = protein
                              organism = synthetic construct
SEQUENCE: 12
VISYAGEVKY YADSVKG                                                  17

SEQ ID NO: 13                 moltype = AA  length = 12
FEATURE                       Location/Qualifiers
REGION                        1..12
                              note = Synthetic peptide
source                        1..12
                              mol_type = protein
                              organism = synthetic construct
SEQUENCE: 13
DPLPLHYYGM DV                                                       12

SEQ ID NO: 14                 moltype = AA  length = 13
FEATURE                       Location/Qualifiers
REGION                        1..13
                              note = Synthetic peptide
source                        1..13
                              mol_type = protein
                              organism = synthetic construct
SEQUENCE: 14
SGSSSNIGRR PVN                                                      13

SEQ ID NO: 15                 moltype = AA  length = 7
FEATURE                       Location/Qualifiers
REGION                        1..7
```

```
                       note = Synthetic peptide
source                 1..7
                       mol_type = protein
                       organism = synthetic construct
SEQUENCE: 15
SQNQRPS                                                                      7

SEQ ID NO: 16          moltype = AA  length = 11
FEATURE                Location/Qualifiers
REGION                 1..11
                       note = Synthetic peptide
source                 1..11
                       mol_type = protein
                       organism = synthetic construct
SEQUENCE: 16
AVWDDIGRVL Q                                                                 11

SEQ ID NO: 17          moltype = AA  length = 121
FEATURE                Location/Qualifiers
REGION                 1..121
                       note = Synthetic peptide
source                 1..121
                       mol_type = protein
                       organism = synthetic construct
SEQUENCE: 17
QVQLVESGGG VVQPGRSLRL SCAASGFTFS SYAMHWVRQA PGKGLEWVAV ISYAGEVKYY  60
ADSVKGRFTI SRDNSKNTLY LQMNSLRAED TAVYYCARDP LPLHYYGMDV WGQGTTVTVS  120
S                                                                            121

SEQ ID NO: 18          moltype = AA  length = 451
FEATURE                Location/Qualifiers
REGION                 1..451
                       note = Synthetic peptide
source                 1..451
                       mol_type = protein
                       organism = synthetic construct
SEQUENCE: 18
QVQLVESGGG VVQPGRSLRL SCAASGFTFS SYAMHWVRQA PGKGLEWVAV ISYAGEVKYY  60
ADSVKGRFTI SRDNSKNTLY LQMNSLRAED TAVYYCARDP LPLHYYGMDV WGQGTTVTVS  120
SASTKGPSVC PLAPSSKSTS GGTAALGCLV KDYFPEPVTV SWNSGALTSG VHTFPAVLQS  180
SGLYSLSSVV TVPSSSLGTQ TYICNVNHKP SNTKVDKRVE PKSVDKTHTC PPCPAPEFEG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPASIEKTI SKAKGQPREP QVYTLPPCRE  360
EMTKNQVSLW CLVKGFYPSD IAVEWESNGQ PENNYKTTPP VLDSDGSFFL YSKLTVDKSR  420
WQQGNVFSCS VMHEALHNHY TQKSLSLSPG K                                          451

SEQ ID NO: 19          moltype = AA  length = 110
FEATURE                Location/Qualifiers
REGION                 1..110
                       note = Synthetic peptide
source                 1..110
                       mol_type = protein
                       organism = synthetic construct
SEQUENCE: 19
QSVLTQPPSA SGTPGQRVTI SCSGSSSNIG RRPVNWYQQL PGTAPKLLIY SQNQRPSGVP  60
DRFSGSQSGT SASLAISGLQ SEDEADYFCA VWDDIGRVLQ LGGGTQLTVL                       110

SEQ ID NO: 20          moltype = AA  length = 216
FEATURE                Location/Qualifiers
REGION                 1..216
                       note = Synthetic peptide
source                 1..216
                       mol_type = protein
                       organism = synthetic construct
SEQUENCE: 20
QSVLTQPPSA SGTPGQRVTI SCSGSSSNIG RRPVNWYQQL PGTAPKLLIY SQNQRPSGVP  60
DRFSGSQSGT SASLAISGLQ SEDEADYFCA VWDDIGRVLQ LGGGTQLTVL GQPKAAPSVT  120
LFPPCSEELQ ANKATLVCLI SDFYPGAVTV AWKADSSPVK AGVETTTPSK QSNNKYAASS  180
YLSLTPEQWK SHRSYSCQVT HEGSTVEKTV APTEVS                                     216

SEQ ID NO: 21          moltype = DNA  length = 366
FEATURE                Location/Qualifiers
misc_feature           1..366
                       note = Synthetic nucleotide
source                 1..366
                       mol_type = other DNA
                       organism = synthetic construct
SEQUENCE: 21
gaggtgcagc tggtggaatc cggcggagga ctggtgcagc ctggcggctc cctgagactg  60
```

-continued

```
tcttgcgccg cctccggctt cacattctcc gactacggca tgcactgggt ccgacaggcc   120
cctggaaagg gcctggaatg ggtggcctac atctcctccg gctcctacac catctactcc   180
gccgactccg tgaagggccg gttcaccatc tcccgggaca cgccaagaa ctccctgtac    240
ctgcagatga actccctgcg ggccgaggac acagccgtgt actactgtgc cagacgggcc   300
cctaactcct tctacgagta ctacttcgac tactggggcc agggcaccac cgtgaccgtg   360
tcctct                                                             366
```

SEQ ID NO: 22           moltype = DNA   length = 1359
FEATURE                 Location/Qualifiers
misc_feature            1..1359
                        note = Synthetic nucleotide
source                  1..1359
                        mol_type = other DNA
                        organism = synthetic construct
SEQUENCE: 22

```
gaggtgcagc tggtggaatc cggcggagga ctggtgcagc ctggcggctc cctgagactg   60
tcttgcgccg cctccggctt cacattctcc gactacggca tgcactgggt ccgacaggcc   120
cctggaaagg gcctggaatg ggtggcctac atctcctccg gctcctacac catctactcc   180
gccgactccg tgaagggccg gttcaccatc tcccgggaca cgccaagaa ctccctgtac    240
ctgcagatga actccctgcg ggccgaggac acagccgtgt actactgtgc cagacgggcc   300
cctaactcct tctacgagta ctacttcgac tactggggcc agggcaccac cgtgaccgtg   360
tcctctgcta gcaccaaagg tccgagcgtt tttccgctgg caccgagcag caaaagcacc   420
tctggtggca ccgcagcact gggttgtctg gtgaaagatt attttccgga accggttacc   480
gtttcttgga atagcggtgc actgaccagc ggtgttcata ccttttccggc agttctgcag   540
agcagcggtc tgtatagcct gtctagcgtt gttaccgttc cgagcagcag cctgggcacc   600
cagacctata tttgcaatgt gaatcataaa ccgagcaata caaaagttga taaacgcgtt   660
gaaccgaaaa gctgtgacaa aactcacacg tgcccaccgt gcccagcacc tgagttcgag   720
gggggaccgt cagtcttcct cttcccccca aaacccaagg acaccctcat gatctcccgg   780
acccctgagg tcacatgcgt ggtggtggac gtgagccacg aagaccctga ggtcaagttc   840
aactggtacg tggacggcgt ggaggtgcat aatgccaaga caaagccgcg ggaggagcag   900
tacaacagca cgtaccgtgt ggtcagcgtc ctcaccgtcc tgcaccagga ctggctgaat   960
ggcaaggagt acaagtgcaa ggtctccaac aaagccctcc cagccagcat cgagaaaacc   1020
atctccaaag ccaaagggca gccccgagaa ccacaggtct gcaccctgcc cccatcccgg   1080
gaggagatga ccaagaacca ggtcagcctg acctgcctgg tcaaaggctt ctatcccagc   1140
gacatcgccg tggagtggga gagcaatggg cagccggaga acaactacaa gaccacgcct   1200
cccgtgctgg actccgacgg ctccttcttc ctcgttagca agctcaccgt ggacaagagc   1260
aggtggcagc aggggaacgt cttctcatgc tccgtgatgc atgaggctct gcacaaccac   1320
tacacgcaga agagcctctc cctgtctccg ggtaaatga                         1359
```

SEQ ID NO: 23           moltype = DNA   length = 336
FEATURE                 Location/Qualifiers
misc_feature            1..336
                        note = Synthetic nucleotide
source                  1..336
                        mol_type = other DNA
                        organism = synthetic construct
SEQUENCE: 23

```
cagatcgtgc tgacccagtc ccctgccacc ctgtccctga gccctggcga gagagccacc   60
ctgagctgct ccgcctcctc caagcacacc aacctgtact ggtcccggca catgtactgg   120
tatcagcaga agcccggcca ggcccctcgg ctgctgatct acctgacctc taaccgggcc   180
accggcatcc ctgccagatt ctccggctct ggctccggca ccgacttcac cctgaccatc   240
tccagcctgg aacccgagga cttcgccgtg tactactgcc agcagtggtc ctccaacccc   300
ttcaccttcg gccagggcac caagctggaa atcaag                             336
```

SEQ ID NO: 24           moltype = DNA   length = 660
FEATURE                 Location/Qualifiers
misc_feature            1..660
                        note = Synthetic nucleotide
source                  1..660
                        mol_type = other DNA
                        organism = synthetic construct
SEQUENCE: 24

```
cagatcgtgc tgacccagtc ccctgccacc ctgtccctga gccctggcga gagagccacc   60
ctgagctgct ccgcctcctc caagcacacc aacctgtact ggtcccggca catgtactgg   120
tatcagcaga agcccggcca ggcccctcgg ctgctgatct acctgacctc taaccgggcc   180
accggcatcc ctgccagatt ctccggctct ggctccggca ccgacttcac cctgaccatc   240
tccagcctgg aacccgagga cttcgccgtg tactactgcc agcagtggtc ctccaacccc   300
ttcaccttcg gccagggcac caagctggaa atcaagcgta cggtggctgc accatctgtc   360
ttcatcttcc cgccatctga tgagcagttg aaatctggaa ctgcctctgt tgtgtgcctg   420
ctgaataact tctatcccag agaggccaaa gtacagtgga aggtggataa cgccctccaa   480
tcgggtaact cccaggagag tgtcacagag caggacagca aggacagcac ctacagcctc   540
agcagcaccc tgacgctgag caaagcagac tacgagaaac acaaagtcta cgcctgcgaa   600
gtcacccatc agggcctgag ctcgcccgtc acaaagagct tcaacagggg agagtgttag   660
```

SEQ ID NO: 25           moltype = DNA   length = 363
FEATURE                 Location/Qualifiers
misc_feature            1..363
                        note = Synthetic nucleotide
source                  1..363
```

```
                        mol_type = other DNA
                        organism = synthetic construct
SEQUENCE: 25
caggtgcagc tggtggagtc tggaggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg cggggggaggt gaaatactac   180
gcagactccg tgaagggccg attcaccatc tccagagaca attccaagaa cacgctgtat   240
ctgcaaatga acagcctgag agctgaggac acggctgtgt attactgtgc gagagacccg   300
ctaccgctac attactacgg tatggacgtc tggggccaag gaccacggt caccgtctcc    360
tca                                                                  363

SEQ ID NO: 26           moltype = DNA   length = 1356
FEATURE                 Location/Qualifiers
misc_feature            1..1356
                        note = Synthetic nucleotide
source                  1..1356
                        mol_type = other DNA
                        organism = synthetic construct
SEQUENCE: 26
caggtgcagc tggtggagtc tggaggaggc gtggtccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg cggggggaggt gaaatactac   180
gcagactccg tgaagggccg attcaccatc tccagagaca attccaagaa cacgctgtat   240
ctgcaaatga acagcctgag agctgaggac acggctgtgt attactgtgc gagagacccg   300
ctaccgctac attactacgg tatggacgtc tggggccaag gaccacggt caccgtctcc    360
tcagcgtcga ccaaaggtcc gagcgtgtcg ccgctgccac cgagcagcaa aagcacctct   420
ggtggcaccg cagcactggg ttgtctggtg aaagattatt ttccggaacc ggttaccgtt   480
tcttggaata gcggtgcact gaccagcggt gttcatacct ttccggcagt cctgcagagc   540
agcggtctgt atagcctgtc tagcgttgtt accgttccga gcagcagcct gggcacccag   600
acctatattt gcaatgtgaa tcataaaccg agcaatacca aagttgataa acgcgttgaa   660
ccgaaaagcg tggacaaaac tcacacgtgc ccaccgtgcc cagcacctga gttcgagggg   720
ggaccgtcag tcttcctctt ccccccaaaa cccaaggaca ccctcatgat ctcccggacc   780
cctgaggtca catgcgtggt ggtggacgtg agccacgaag accctgaggt caagttcaac   840
tggtacgtgg acggcgtgga ggtgcataat gccaagacaa agccgcggga ggagcagtac   900
aacagcacgt accgtgtggt cagcgtcctc accgtcctgc accaggactg gctgaatggc   960
aaggagtaca agtgcaaggt ctccaacaaa gccctcccag ccagcatcga gaaaaccatc  1020
tccaaagcca aagggcagcc ccgagaacca caggtctaca ccctgccccc atgccgggag  1080
gagatgacca gaaccaggt cagcctgtgg tgcctggtca aaggcttcta tcccagcgac  1140
atcgccgtgg agtgggagag caatgggcag ccggagaaca actacaagac cacgcctccc  1200
gtgctggact ccgacggctc cttcttcctc tatagcaagc tcaccgtgga caagagcagg  1260
tggcagcagg ggaacgtctt ctcatgctcc gtgatgcatg aggctctgca caaccactac  1320
acgcagaaga gcttaagcct gtctccgggt aaatga                             1356

SEQ ID NO: 27           moltype = DNA   length = 330
FEATURE                 Location/Qualifiers
misc_feature            1..330
                        note = Synthetic nucleotide
source                  1..330
                        mol_type = other DNA
                        organism = synthetic construct
SEQUENCE: 27
cagtctgtgc tgactcagcc tccctcagcg tctgggaccc ccgggcagag ggtcaccatc    60
tcttgttctg gaagcagctc caatatcgga aggaggcctg taaactggta ccagcagctc   120
ccaggaacgg cccccaaact cctcatctat agtcagaatc agcggccctc aggggtccct   180
gaccgattct ctggctccca gtctggcacc tcagcctccc tggccatcag tgggctccag   240
tctgaggatg aggctgatta tttctgtgca gtttgggatg acatcggccg cgtcctgcag   300
ttaggcggag gcacccagct gaccgtccta                                     330

SEQ ID NO: 28           moltype = DNA   length = 651
FEATURE                 Location/Qualifiers
misc_feature            1..651
                        note = Synthetic nucleotide
source                  1..651
                        mol_type = other DNA
                        organism = synthetic construct
SEQUENCE: 28
cagtctgtgc tgactcagcc tccctcagcg tctgggaccc ccgggcagag ggtcaccatc    60
tcttgttctg gaagcagctc caatatcgga aggaggcctg taaactggta ccagcagctc   120
ccaggaacgg cccccaaact cctcatctat agtcagaatc agcggccctc aggggtccct   180
gaccgattct ctggctccca gtctggcacc tcagcctccc tggccatcag tgggctccag   240
tctgaggatg aggctgatta tttctgtgca gtttgggatg acatcggccg cgtcctgcag   300
ttaggcggag gcacccagct gaccgtccta ggtcagccca aggcggcccc ctcggtcact   360
ctgttccgc cctgctctga ggagcttcaa gccaacaagg ccacactggt gtgtctcata   420
agtgacttct acccgggagc cgtgacagtg gcctggaagg cagatagcag cccgtcaag   480
gcgggagtgg agaccaccac accctccaaa caaagcaaca caagtacgc ggccagcagc   540
tacctgagcc tgacgcctga gcagtggaag tcccacagaa gctacagctg ccaggtcacg   600
catgaaggga gcaccgtgga gaagacagtg gcccctacaa agtgtcatg a              651

SEQ ID NO: 29           moltype = AA   length = 9
```

```
FEATURE               Location/Qualifiers
REGION                1..9
                      note = Epstein Barr virus
source                1..9
                      mol_type = protein
                      organism = synthetic construct
SEQUENCE: 29
FLYALALLL                                                                    9

SEQ ID NO: 30         moltype = AA  length = 9
FEATURE               Location/Qualifiers
REGION                1..9
                      note = Epstein Barr virus
source                1..9
                      mol_type = protein
                      organism = synthetic construct
SEQUENCE: 30
CLGGLLTMV                                                                    9

SEQ ID NO: 31         moltype = AA  length = 9
FEATURE               Location/Qualifiers
REGION                1..9
                      note = Epstein Barr virus
source                1..9
                      mol_type = protein
                      organism = synthetic construct
SEQUENCE: 31
GLCTLVAML                                                                    9

SEQ ID NO: 32         moltype = AA  length = 9
FEATURE               Location/Qualifiers
source                1..9
                      mol_type = protein
                      organism = Alphainfluenzavirus influenzae
SEQUENCE: 32
GILGFVFTL                                                                    9

SEQ ID NO: 33         moltype = AA  length = 9
FEATURE               Location/Qualifiers
source                1..9
                      mol_type = protein
                      organism = Alphainfluenzavirus influenzae
SEQUENCE: 33
FMYSDFHFI                                                                    9

SEQ ID NO: 34         moltype = AA  length = 9
FEATURE               Location/Qualifiers
REGION                1..9
                      note = Cytomegalovirus
source                1..9
                      mol_type = protein
                      organism = synthetic construct
SEQUENCE: 34
NLVPMVATV                                                                    9

SEQ ID NO: 35         moltype = AA  length = 121
FEATURE               Location/Qualifiers
REGION                1..121
                      note = Synthetic Construct
source                1..121
                      mol_type = protein
                      organism = synthetic construct
SEQUENCE: 35
EVQLVETGGG LIQPGRSLRL SCAASGFTFS SYAMHWVRQA PGKGLEWVAV ISYAGEVKYY  60
ADSVKGRFTI SRDNSKNTLY LQMNSLRAED TAVYYCARDP LPLHYYGMDV WGQGTTVTVS  120
S                                                                    121

SEQ ID NO: 36         moltype = AA  length = 110
FEATURE               Location/Qualifiers
REGION                1..110
                      note = Synthetic Construct
source                1..110
                      mol_type = protein
                      organism = synthetic construct
SEQUENCE: 36
QSALTQPRSA SGNPGQRVTI SCSGSSSNMG RRPVNWYQQI PGTAPKLLIY SQNQRPSGVP  60
DRFSGSQSGT SASLTISGLQ SEDEAEYFCA VWDDIGRVLQ LGGGTQLAVL            110

SEQ ID NO: 37         moltype = AA  length = 121
```

-continued

```
FEATURE                 Location/Qualifiers
REGION                  1..121
                        note = Synthetic Construct
source                  1..121
                        mol_type = protein
                        organism = synthetic construct
SEQUENCE: 37
QVQLVETGGG LIQPGRSLRL SCAASGFTFS SYAMHWVRQA PGKGLEWVAV ISYAGEVKYY    60
ADSVKGRFTI SRDNSKNTLY LQMNSLRAED TAVYYCARDP LPLHYYGMDV WGQGTTVTVS   120
S                                                                  121

SEQ ID NO: 38           moltype = DNA   length = 363
FEATURE                 Location/Qualifiers
misc_feature            1..363
                        note = Synthetic Construct
source                  1..363
                        mol_type = other DNA
                        organism = synthetic construct
SEQUENCE: 38
gaggtgcagc tggtggagac tggaggaggc ttgatccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg gggtggcaggt gaaatactac   180
gcagactccg tgaagggccg attcaccatc tccagagaca attccaagaa cacgctgtat   240
ctgcaaatga acagcctgag agctgaggac acggctgtgt attactgtgc gagagacccg   300
ctaccgctac attactacgg tatggacgtc tggggccaag ggaccacggt caccgtctcc   360
tca                                                                363

SEQ ID NO: 39           moltype = DNA   length = 330
FEATURE                 Location/Qualifiers
misc_feature            1..330
                        note = Synthetic Construct
source                  1..330
                        mol_type = other DNA
                        organism = synthetic construct
SEQUENCE: 39
cagtctgccc tgactcagcc tcgctcagcg tctgggaacc ccgggcagag ggtcaccatc    60
tcttgttctg gaagcagctc caatatggga aggaggcctg taaactggta ccagcagatc   120
ccaggaacgg cccccaaact cctcatctat agtcagaatc agcggccctc aggggtccct   180
gaccgattct ctggctccca gtctggcacc tcagcctccc tgaccatcag tgggctccag   240
tctgaggatg aggctgaata tttctgtgca gtttgggatg acatcggccg cgtcctgcag   300
ttaggcggag gcacccagct ggccgtccta                                   330

SEQ ID NO: 40           moltype = DNA   length = 363
FEATURE                 Location/Qualifiers
misc_feature            1..363
                        note = Synthetic Construct
source                  1..363
                        mol_type = other DNA
                        organism = synthetic construct
SEQUENCE: 40
caggtgcagc tggtggagac tggaggaggc ttgatccagc ctgggaggtc cctgagactc    60
tcctgtgcag cctctggatt caccttcagt agctatgcta tgcactgggt ccgccaggct   120
ccaggcaagg ggctggagtg ggtggcagtt atatcatatg cggggggaggt gaaatactac   180
gcagactccg tgaagggccg attcaccatc tccagagaca attccaagaa cacgctgtat   240
ctgcaaatga acagcctgag agctgaggac acggctgtgt attactgtgc gagagacccg   300
ctaccgctac attactacgg tatggacgtc tggggccaag ggaccacggt caccgtctcc   360
tca                                                                363
```

BISPECIFIC PD-1 AND TIGIT BINDING PROTEINS AND USES THEREOF

CROSS-REFERENCE TO RELATED APPLICATIONS

This application claims priority to U.S. patent application Ser. No. 17/661,307 filed Apr. 29, 2022, which claims priority benefit of U.S. Provisional Application No. 63/182,156, filed Apr. 30, 2021, the contents of which are hereby incorporated by reference herein.

INCORPORATION-BY-REFERENCE OF MATERIAL SUBMITTED ELECTRONICALLY

Incorporated by reference in its entirety herein is a nucleotide/amino acid sequence listing submitted concurrently herewith and identified as follows: One 58,643 Byte file named "TIGIT-101-US-CNT_SEQ_LIST.xml" created on Feb. 13, 2024.

FIELD OF THE DISCLOSURE

The disclosure relates to binding proteins, including antibodies, that specifically bind to Programmed Death-1 ("PD-1") and T cell immunoreceptor with Ig and ITIM domains ("TIGIT"). The disclosure also provides compositions comprising such binding proteins and nucleic acid molecules encoding such binding proteins. The disclosure further relates to methods of treating a disorder or condition using such binding proteins.

BACKGROUND

Programmed Death-1 ("PD-1") is an approximately 31 kD type I membrane protein that is member of the extended CD28/CTLA4 family of T cell regulators (see Ishida et al., "Induced Expression of PD-1, A Novel Member of the Immunoglobulin Gene Superfamily, Upon Programmed Cell Death," *EMBO J.* 11: 3887-95 (1992)). PD-1 is expressed on activated T cells, B cells, and monocytes and at low levels in natural killer (NK) T cells. PD-1 is a well-validated target for immune mediated therapy in oncology. Antagonistic inhibition of the PD-1/PD-L1 interaction increases T cell activation, enhancing recognition and elimination of tumour cells by the host immune system.

TIGIT (also known as T cell immunoreceptor with Ig and ITIM domains) is an immune receptor present on some T cells and Natural Killer Cells (NK). TIGIT is upregulated by immune cells, including activated T cells, natural killer cells, and regulatory T cells.

SUMMARY

Provided herein is a bispecific binding protein that specifically binds to PD-1 and TIGIT comprising: a) a first binding domain that specifically binds to PD-1, wherein the first binding domain comprises a heavy chain variable domain comprising a HCDR1 having the amino acid sequence of SEQ ID NO: 1, a HCDR2 having the amino acid sequence of SEQ ID NO: 2, and a HCDR3 having the amino acid sequence of SEQ ID NO: 3, and a light chain variable domain comprising a LCDR1 having the amino acid sequence of SEQ ID NO: 4, a LCDR2 having the amino acid sequence of SEQ ID NO: 5 and a LCDR3 having the amino acid sequence of SEQ ID NO: 6; and b) a second binding domain that specifically binds to TIGIT, wherein the second binding domain comprises a heavy chain variable domain comprising a HCDR1 having the amino acid sequence of SEQ ID NO: 11, a HCDR2 having the amino acid sequence of SEQ ID NO: 12, and a HCDR3 having the amino acid sequence of SEQ ID NO: 13, and a light chain variable domain comprising a LCDR1 having the amino acid sequence of SEQ ID NO: 14, a LCDR2 having the amino acid sequence of SEQ ID NO: 15, and a LCDR3 having the amino acid sequence of SEQ ID NO: 16.

Also provided herein is a method of treating a subject having a tumor comprising administering to the subject a therapeutically effective amount of the bispecific binding proteins disclosed herein. Also provided herein is a method of treating or preventing cancer in a subject comprising administering the bispecific binding proteins disclosed herein.

BRIEF DESCRIPTION OF THE DRAWINGS

Figure 3A:
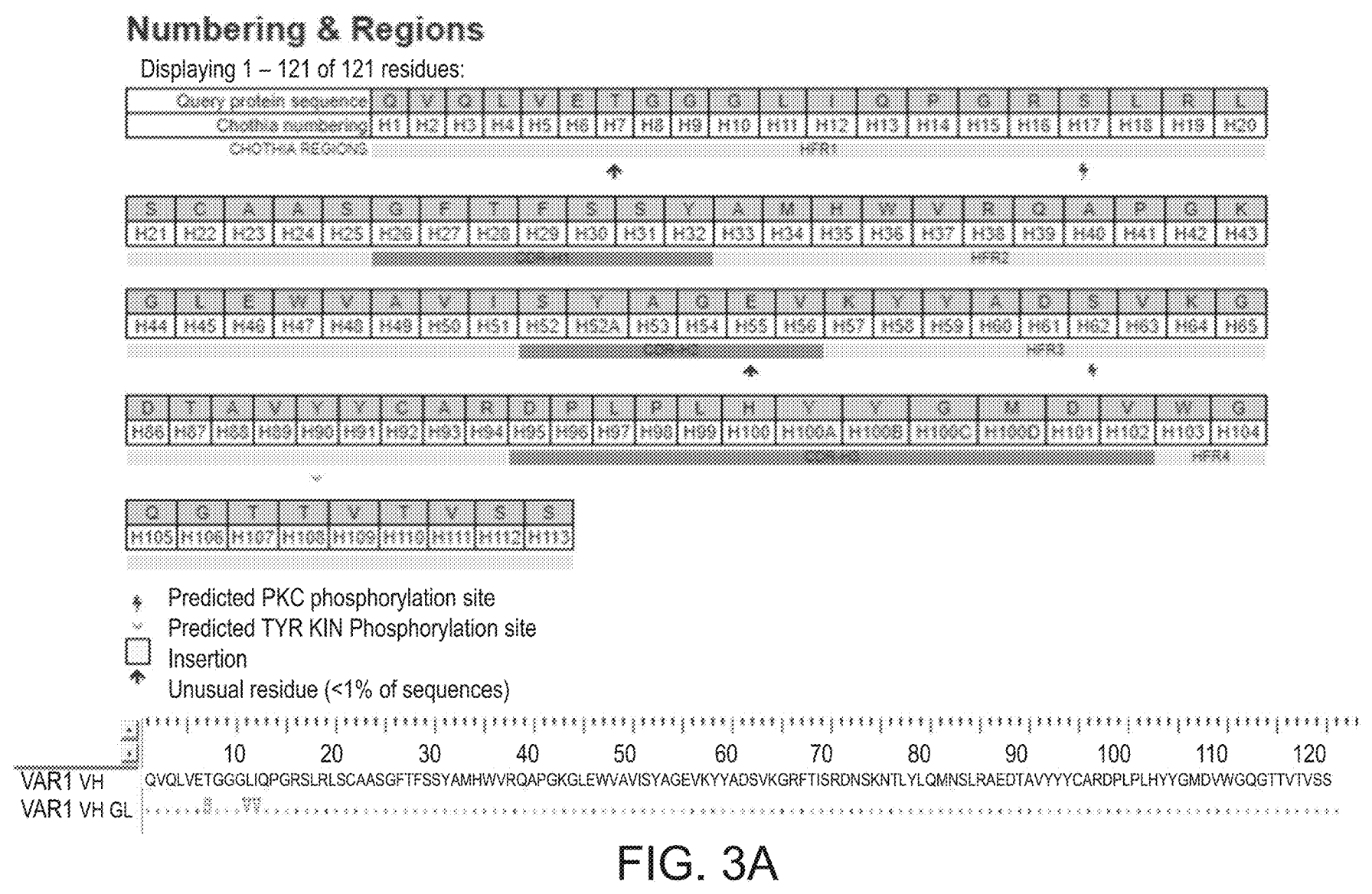

FIGS. 3A and 3B show the alignment of the variable heavy chain and encoding nucleic acid (SEQ ID NO: 40) of parental VAR1 with the germline sequence (SEQ ID NO: 7 and SEQ ID NO: 37). CDRs in FIG. 3A are highlighted according to the Chothia numbering system. CDRs in FIG. 3B are highlighted according to the IMGT numbering system. The alignment illustrates that parental VAR1 had four amino acids in FR1 that were not germline and which were not Vernier residues.

Figure 4B:
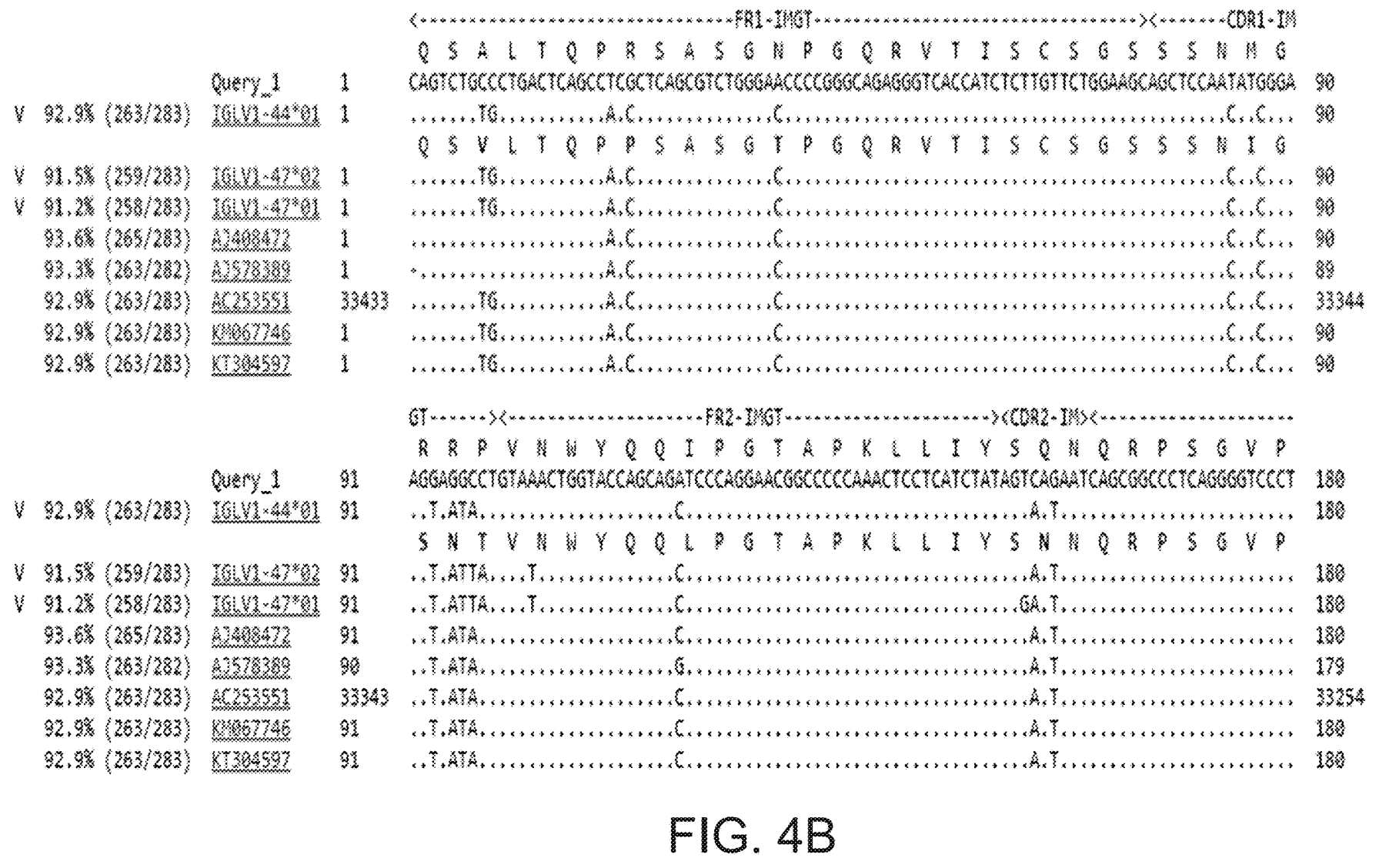
Figure 4B:
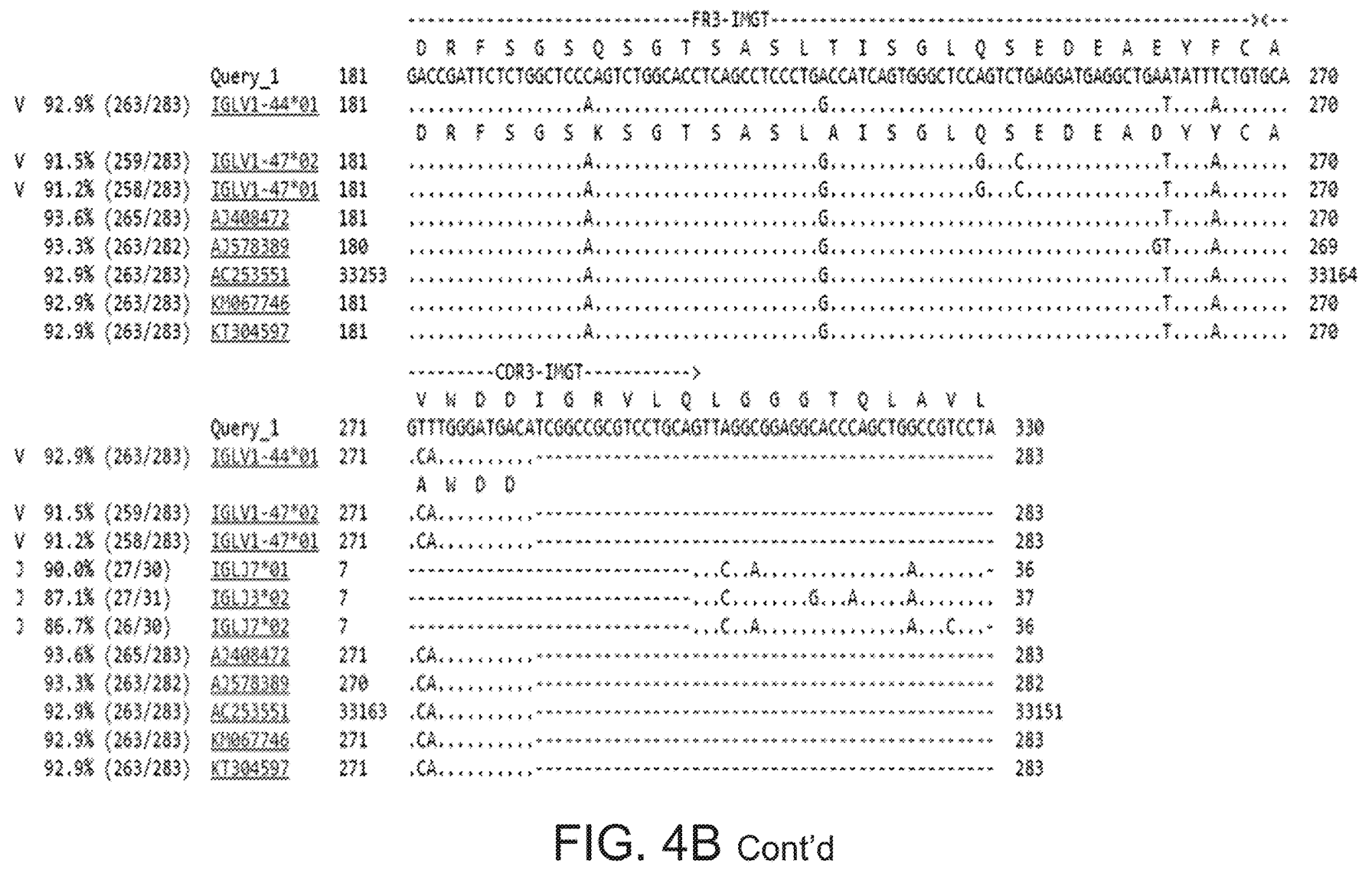

FIGS. 4A and 4B shows the alignment of the variable light chain and encoding nucleic acid (SEQ ID NO: 39) of parental VAR1 with the germline sequence (SEQ ID NO: 19 and SEQ ID NO: 36). The alignment illustrates that the VL of parental VAR1 had ten amino acids that were not germline, a Vernier residue Q (Q-K) in FR3, a chain packing residue F (F-Y) before CDRL3, and a chain packing residue L (L-F) after CDRL3.

FIG. 8A shows simultaneous binding using antigen capture format. Sensors loaded with human TIGIT antigen were exposed to successive association and dissociation interactions first with AZD2936 then with human PD-1. Asso: association; Disso: dissociation; SA: streptavidin. FIG. 8B shows simultaneous binding using antigen capture format. Sensors loaded with human PD-1 antigen were exposed to successive association and dissociation interactions first with AZD2936 then with human TIGIT. Asso: association; Disso: dissociation; Ni-NTA: nickel nitrilotriacetic acid.

FIG. 9A shows cellular binding of AZD2936 to Human TIGIT Receptors on engineered Jurkat PD-1⁻ TIGIT⁺ cells. FIG. 9B shows cellular binding of AZD2936 to Human PD-1 Receptors on engineered Jurkat PD-1⁺

TIGIT⁻ cells. FIG. 9C shows cellular binding of AZD2936 to Human PD-1 and TIGIT Receptors on Jurkat PD-1⁻ TIGIT⁺, Jurkat PD-1⁺TIGIT⁻, or double expressing Jurkat PD-1⁺TIGIT⁺. MFI=geometric mean fluorescence intensity; PD-1=programmed cell-death protein 1; TIGIT=T cell immunoreceptor with Ig and immunoreceptor tyrosine-based inhibitory motif domains. Cellular binding to human single expressing cell lines: Jurkat PD-1⁻ TIGIT⁺ and Jurkat PD-1⁺TIGIT⁻ or human double expressing Jurkat PD-1⁺ TIGIT⁺. Test and control article antibodies were detected with fluorescently conjugated goat anti human IgG secondary antibody and evaluated by flow cytometry.

FIG. 10A shows bioactivity of AZD2936 and Anti-PD-1 Antibody in Human PD 1⁺TIGIT⁻ Jurkat T Cell NFAT-Luciferase Reporter Two-cell Co-culture Assays. FIG. 10B shows bioactivity of AZD2936 in Human PD-1-TIGIT⁺ Jurkat T Cell NFAT Luciferase Reporter Two-cell Co-culture Assays. FIG. 10C shows bioactivity of AZD2936 in human PD-1⁺TIGIT⁺ Jurkat T cell NFAT Luciferase Reporter Two-cell Co-culture Assays. CD155=cluster of differentiation 155; CHO=Chinese hamster ovary; NFAT=nuclear factor of activated T cells; PD-1=programmed cell-death protein 1; RLU=relative light unit; SD=standard deviation; TCR=T cell receptor; TIGIT=T cell immunoreceptor with Ig and immunoreceptor tyrosine-based inhibitory motif domains.

FIG. 11A shows the data for PBMC from five donors. FIG. 11B shows the fold-increase of human IFN-γ released from a T cell and human tumor cells co-culture assay in response to AZD2936 and other antibodies. FIG. 11C shows a concentration titration of antibodies from 10 nM to 0.1 pM. FIG. 11D shows the arithmetic mean cytotoxicity EC50 for AZD2936 (n=6) in assays similarly conducted as in FIG. 11C.

DETAILED DESCRIPTION

Figure 1:
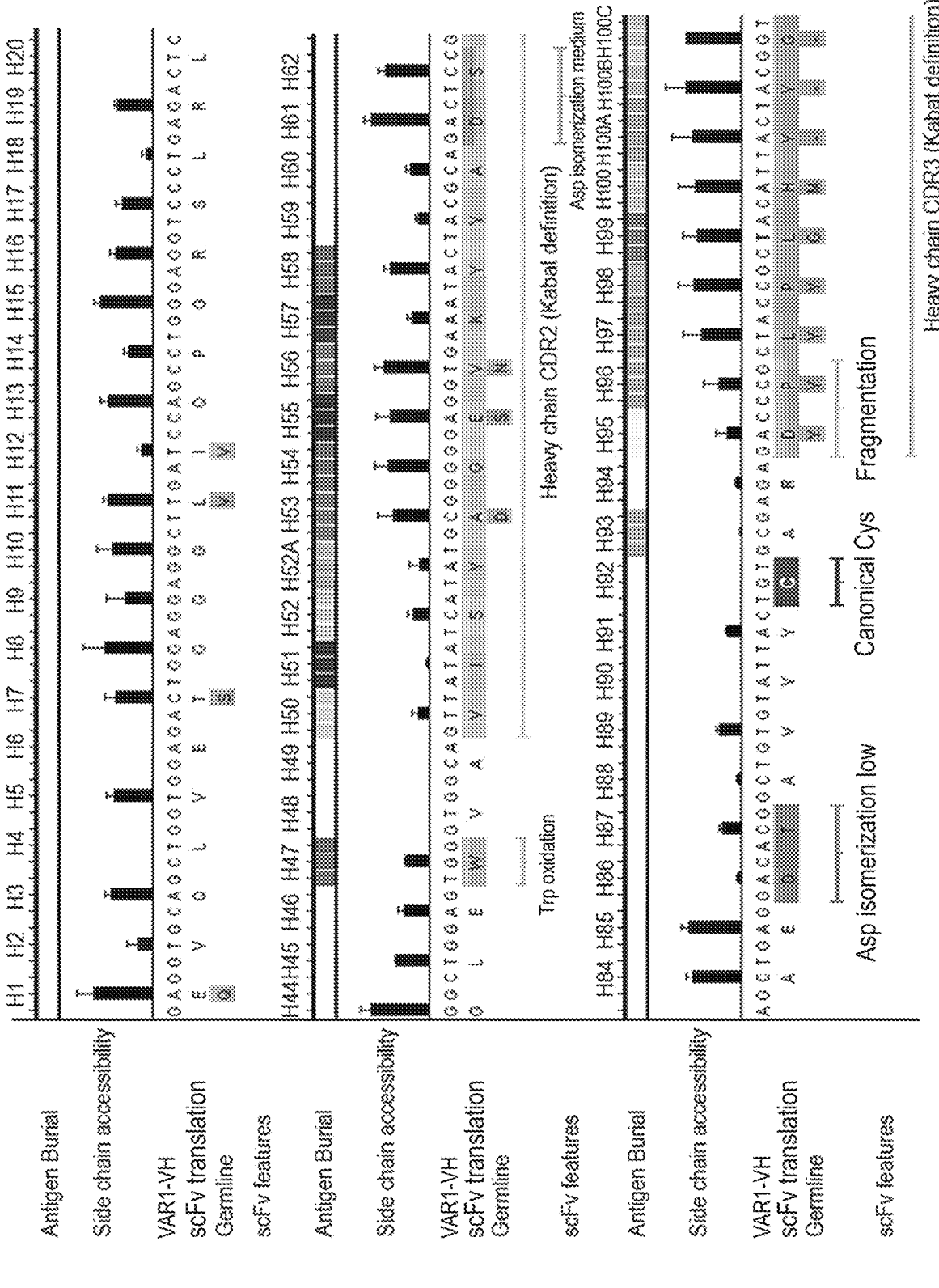
FIG. 1 shows a sequence analysis of the residues identified in the parental VAR1 variable heavy chain (SEQ ID NO: 35) and nucleic acid (SEQ ID NO: 38).
Figure 1:
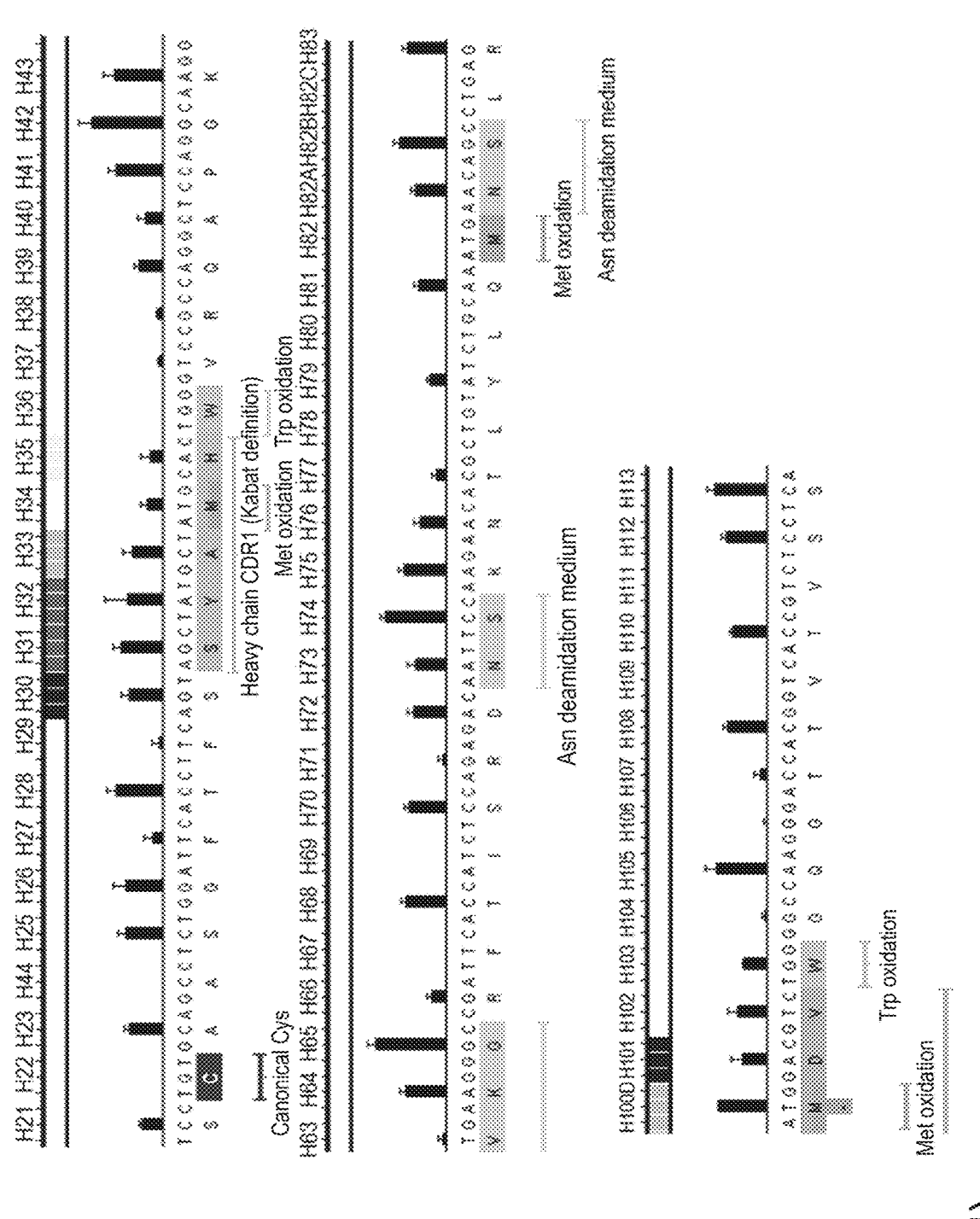

The disclosure relates to binding proteins, including antibodies, that bind to PD-1 and TIGIT. The disclosure also provides compositions comprising such binding proteins and nucleic acid molecules encoding such binding proteins.

The disclosure further relates to methods of treating a disorder or condition using such binding proteins.

As utilized in accordance with the present disclosure, unless otherwise indicated, all technical and scientific terms shall be understood to have the same meaning as commonly understood by one of ordinary skill in the art. Unless otherwise required by context, singular terms shall include pluralities and plural terms shall include the singular.

The term "antibody" as used herein refers to a protein that is capable of recognizing and specifically binding to an antigen. Ordinary or conventional mammalian antibodies comprise a tetramer, which is typically composed of two identical pairs of polypeptide chains, each pair consisting of one "light" chain (typically having a molecular weight of about 25 kDa) and one "heavy" chain (typically having a molecular weight of about 50-70 kDa). The terms "heavy chain" and "light chain," as used herein, refer to any immunoglobulin polypeptide having sufficient variable domain sequence to confer specificity for a target antigen. The amino-terminal portion of each light and heavy chain typically includes a variable domain of about 100 to 110 or more amino acids that typically is responsible for antigen recognition. The carboxyl-terminal portion of each chain typically defines a constant domain responsible for effector function. Thus, in a naturally occurring antibody, a full-length heavy chain immunoglobulin polypeptide includes a variable domain ($V_H$) and three constant domains ($C_{H1}$, $C_{H2}$, and $C_{H3}$) and a hinge region between $C_{H1}$ and $C_{H2}$, wherein the $V_H$ domain is at the amino-terminus of the polypeptide and the $C_{H3}$ domain is at the carboxyl-terminus, and a full-length light chain immunoglobulin polypeptide includes a variable domain ($V_L$) and a constant domain ($C_L$), wherein the $V_L$ domain is at the amino-terminus of the polypeptide and the $C_L$ domain is at the carboxyl-terminus. Those of skill in the art, however, would appreciate that the locations of the domains in a naturally occurring antibody can be modified in certain antibody-like binding protein formats without a loss of antigen-binding capability. Classes of human light chains are termed kappa and lambda light chains.

In some aspects, the light chain constant region is a kappa chain. In some aspects, light chain constant region is a lambda chain.

Within full-length light and heavy chains, the variable and constant domains typically are joined by a "J" region of about 12 or more amino acids, with the heavy chain also including a "D" region of about 10 more amino acids. The variable regions of each light/heavy chain pair typically form an antigen-binding site. The variable domains of naturally occurring antibodies typically exhibit the same general structure of relatively conserved framework regions (FR) joined by three hypervariable regions, also called complementarity determining regions or CDRs. The CDRs from the two chains of each pair typically are aligned by the framework regions, which may enable binding to a specific epitope. From the amino-terminus to the carboxyl-terminus, both light and heavy chain variable domains typically comprise the domains FR1, CDR1, FR2, CDR2, FR3, CDR3, and FR4.

The term "antibody fragment" refers to a portion of an intact or full-length chain or an antibody, generally the target binding or variable region. Examples of antibody fragments include, but are not limited to, $F_{ab}b$, $F_{ab}$, $F_{(ab')2}$ and $F_v$ fragments. As used herein, the term "functional fragment" is generally synonymous with "antibody fragment," and with respect to antibodies, can refer to antibody fragments such as $F_v$, $F_{ab}$, $F_{(ab')2}$.

Reference to the numbering of amino acid residues described herein is performed according to the EU numbering system (also described in Kabat et al, Sequences of Proteins of Immunological Interest, 5th Ed. Public Health Service, National Institutes of Health, Bethesda, MD. (1991)).

The term "vector," refers to any molecule (e.g., nucleic acid, plasmid, or virus) that is used to transfer coding information to a host cell. One type of vector is a "plasmid," which refers to a circular double-stranded DNA molecule into which additional DNA segments may be inserted. Another type of vector is a viral vector, wherein additional DNA segments may be inserted into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell and thereby are replicated along with the host genome. In addition, certain vectors are capable of directing the expression of genes to which they are operatively linked. Such vectors are referred to herein as "expression vectors."

The term "human antibody," as used herein, includes antibodies having variable and constant regions substantially corresponding to human germline immunoglobulin sequences. In some aspects, human antibodies are produced in non-human mammals, including, but not limited to, rodents, such as mice and rats, and lagomorphs, such as rabbits. In other aspects, human antibodies are produced in hybridoma cells. In still other aspects, human antibodies are produced recombinantly. In some aspects, the bispecific binding protein is a human or humanized antibody.

The term "antigen" or "target antigen" as used herein refers to a molecule or a portion of a molecule that is capable of being recognized by and bound by binding proteins of the disclosure. The target antigen is capable of being used in an animal to produce antibodies capable of binding to an epitope of that antigen. A target antigen may have one or more epitopes.

The term "epitope" as used herein refers to a region or structural element of an antigen that is recognized and bound by a binding protein of the disclosure. More precisely, the epitope is the specific structure that is bound by the CDRs of the binding protein. Epitopes can comprise protein structural elements, carbohydrates or even portions of lipid structures found in membranes. A binding protein is said to specifically bind an antigen when it preferentially recognizes its antigen target in a complex mixture of proteins and/or macromolecules. The term "specifically binds" refers to a binding protein that specifically binds to a molecule or a fragment thereof (e.g., antigen). A binding protein that specifically binds a molecule or a fragment thereof may bind to other molecules with lower affinity as determined by, for example, immunoassays, BIAcore, or other assays known in the art. In particular, antibodies or fragments that specifically bind to at least one molecule or a fragment thereof can compete off molecules that bind non-specifically. The present disclosure specifically encompasses antibodies with multiple specificities (e.g., an antibody with specificity for two or more discrete antigens. For example, a bispecific antibody can bind to two adjacent epitopes on a single target antigen, or can bind to two different antigens.

The term "antigen binding site" as used herein refers to a site created on the surface of a binding protein of the disclosure where an antigen or an epitope on an antigen is bound. The antigen binding site of the binding protein is typically described by reference to the loop structures created by complementarity determining regions (CDRs) of the binding protein.

In some aspects, the binding proteins provided herein are bispecific. As used herein, bispecific binding proteins have binding specificities for at least two independent antigens (or targets) or different epitopes within the same antigen. Exemplary bispecific binding proteins may bind to two different epitopes of a target, or may bind two different targets. Other such binding proteins may combine a first target binding site with a second binding site for another target. In some aspects, the binding protein is a bispecific antibody.

In some aspects, bispecific antibodies provide additive and/or synergistic therapeutic effects derived from targeting two antigens simultaneously, with the administration of a single manufactured molecule.

In some aspects, the antibodies provided herein are monovalent bispecific antibodies (MBab). The monovalent bispecific antibody scaffolds described herein provide a superior platform for the generation of bispecific antibodies that fulfill all the benefits associated with bispecific antibodies while reducing the potential therapeutic risks mentioned above due to their monovalent nature. Furthermore, the MBabs provided herein are readily expressed, stable, and are likely to have low immunogenicity. As used herein, the term "monovalent bispecific," which may be abbreviated "MBab," refers to bispecific antibodies, where each arm can specifically bind to a different target antigen, and for a given pair of different target antigens (A and B), the MBab can bind to one of each. In certain aspects, monovalent bispecific antibodies can specifically bind to two independent antigens (or targets) or two independent epitopes on the same antigen. Typically, monovalent bispecific antibodies comprise two different variable regions. In some aspects, the binding affinity for the two independent antigens is about the same. In some aspects, the binding affinities for the two independent antigens are different.

In some aspects provided herein is a bispecific binding protein that specifically binds to PD-1 and TIGIT comprising: a) a first binding domain that specifically binds to PD-1, wherein the first binding domain comprises a heavy chain variable domain comprising a HCDR1 having the amino acid sequence of SEQ ID NO: 1, a HCDR2 having the amino acid sequence of SEQ ID NO: 2, and a HCDR3 having the amino acid sequence of SEQ ID NO: 3, and a light chain variable domain comprising a LCDR1 having the amino acid sequence of SEQ ID NO: 4, a LCDR2 having the amino acid sequence of SEQ ID NO: 5 and a LCDR3 having the amino acid sequence of SEQ ID NO: 6; and b) a second binding domain that specifically binds to TIGIT, wherein the second binding domain comprises a heavy chain variable domain comprising a HCDR1 having the amino acid sequence of SEQ ID NO: 11, a HCDR2 having the amino acid sequence of SEQ ID NO: 12, and a HCDR3 having the amino acid sequence of SEQ ID NO: 13, and a light chain variable domain comprising a LCDR1 having the amino acid sequence of SEQ ID NO: 14, a LCDR2 having the amino acid sequence of SEQ ID NO: 15, and a LCDR3 having the amino acid sequence of SEQ ID NO: 16.

In some aspects, the first binding domain that specifically binds to PD-1 comprises a heavy chain variable domain having the amino acid sequence of SEQ ID NO: 7 and a light chain variable domain having the amino acid sequence of SEQ ID NO: 9. In some aspects, the first binding domain that specifically binds to PD-1 comprises a heavy chain having the amino acid sequence of SEQ ID NO: 8 and a light chain having the amino acid sequence of SEQ ID NO: 10.

In some aspects, the first binding domain that specifically binds to PD-1 comprises a heavy chain variable domain having an amino acid sequence that is at least 90, 91, 92, 93, 94, 95, 96, 97, 98, or 99% identical to the amino acid sequence of SEQ ID NO: 7. In some aspects, the first binding domain that specifically binds to PD-1 comprises a light chain variable domain having an amino acid sequence that is at least 90, 91, 92, 93, 94, 95, 96, 97, 98, or 99% identical to the amino acid sequence of SEQ ID NO: 9.

In some aspects, the first binding domain that specifically binds to PD-1 comprises a heavy chain having an amino acid sequence that is at least 90, 91, 92, 93, 94, 95, 96, 97, 98, or 99% identical to the amino acid sequence of SEQ ID NO: 8. In some aspects, the first binding domain that specifically binds to PD-1 comprises a light chain having an amino acid sequence that is at least 90, 91, 92, 93, 94, 95, 96, 97, 98, or 99% identical to the amino acid sequence of SEQ ID NO: 10.

In some aspects, the second binding domain that specifically binds TIGIT comprises a heavy chain variable domain having the amino acid sequence of SEQ ID NO: 17 and a light chain variable domain having the amino acid sequence of SEQ ID NO: 19. In some aspects, the second binding domain that specifically binds to TIGIT comprises a heavy chain having the amino acid sequence of SEQ ID NO: 18 and a light chain having the amino acid sequence of SEQ ID NO: 20.

In some aspects, the second binding domain that specifically binds to TIGIT comprises a heavy chain variable domain having an amino acid sequence that is at least 90, 91, 92, 93, 94, 95, 96, 97, 98, or 99% identical to the amino acid sequence of SEQ ID NO: 17. In some aspects, the second binding domain that specifically binds to TIGIT comprises a light chain variable domain having an amino acid sequence that is at least 90, 91, 92, 93, 94, 95, 96, 97, 98, or 99% identical to the amino acid sequence of SEQ ID NO: 19.

In some aspects, the second binding domain that specifically binds to TIGIT comprises a heavy chain having an amino acid sequence that is at least 90, 91, 92, 93, 94, 95, 96, 97, 98, or 99% identical to the amino acid sequence of SEQ ID NO: 18. In some aspects, the second binding domain that specifically binds to TIGIT comprises a light chain having an amino acid sequence that is at least 90, 91, 92, 93, 94, 95, 96, 97, 98, or 99% identical to the amino acid sequence of SEQ ID NO: 20.

In some aspects, the first binding domain that specifically binds to PD-1 comprises a heavy chain variable domain that is encoded by the nucleic acid sequence of SEQ ID NO: 21 and a light chain variable domain is encoded by the nucleic acid sequence of SEQ ID NO: 23. In some aspects, the first binding domain that specifically binds to PD-1 comprises a heavy chain is encoded by the nucleic acid sequence of SEQ ID NO: 22 and a light chain is encoded by the nucleic acid sequence of SEQ ID NO: 24.

In some aspects, the first binding domain that specifically binds to PD-1 comprises a heavy chain variable domain that is encoded by a nucleic acid sequence that is at least 90, 91, 92, 93, 94, 95, 96, 97, 98, or 99% identical to SEQ ID NO: 21 and a light chain variable domain is encoded by a nucleic acid sequence that is at least 90, 91, 92, 93, 94, 95, 96, 97, 98, or 99% identical to SEQ ID NO: 23.

In some aspects, the first binding domain that specifically binds to PD-1 comprises a heavy chain is encoded by a nucleic acid sequence that is at least 90, 91, 92, 93, 94, 95, 96, 97, 98, or 99% identical to SEQ ID NO: 22 and a light chain is encoded by a nucleic acid sequence that is at least 90, 91, 92, 93, 94, 95, 96, 97, 98, or 99% identical to SEQ ID NO: 24.

In some aspects, the second binding domain that specifically binds TIGIT comprises a heavy chain variable domain that is encoded by the nucleic acid sequence of SEQ ID NO: 25 and a light chain variable domain that is encoded by the nucleic acid sequence of SEQ ID NO: 27. In some aspects, the second binding domain that specifically binds to TIGIT comprises a heavy chain that is encoded by the nucleic acid sequence of SEQ ID NO: 26 and a light chain that is encoded by the nucleic acid sequence of SEQ ID NO: 28.

In some aspects, the second binding domain that specifically binds TIGIT comprises a heavy chain variable domain that is encoded by a nucleic acid sequence that is at least 90, 91, 92, 93, 94, 95, 96, 97, 98, or 99% identical to SEQ ID NO: 25 and a light chain variable domain that is encoded by a nucleic acid sequence that is at least 90, 91, 92, 93, 94, 95, 96, 97, 98, or 99% identical to ID NO: 27.

In some aspects, the second binding domain that specifically binds to TIGIT comprises a heavy chain that is encoded by a nucleic acid sequence that is at least 90, 91, 92, 93, 94, 95, 96, 97, 98, or 99% identical to SEQ ID NO: 26 and a light chain that is encoded by a nucleic acid sequence that is at least 90, 91, 92, 93, 94, 95, 96, 97, 98, or 99% identical to SEQ ID NO: 28.

In one aspect, useful bispecific binding proteins compete with any bispecific binding proteins contained herein for binding to both PD-1 and TIGIT. In one aspect, a useful binding protein competes with an antibody comprising SEQ ID NO: 7, SEQ ID NO: 9, SEQ ID NO: 17, and SEQ ID NO: 19 for binding to both PD-1 and TIGIT. In another aspect, a useful binding protein competes with an antibody comprising SEQ ID NO: 8, SEQ ID NO: 10, SEQ ID NO: 18, and SEQ ID NO: 20 for binding to both PD-1 and TIGIT.

In one aspect, the disclosure provides a nucleic acid comprising a nucleotide sequence encoding a bispecific binding protein as described herein.

In one aspect, the disclosure provides a nucleic acid sequence encoding a bispecific binding protein as described herein, where the nucleic acid sequence comprises one or more of: a sequence at least 90, 91, 92, 93, 94, 95, 96, 97, 98, or 99% identical to SEQ ID NO:21, a sequence at least 90, 91, 92, 93, 94, 95, 96, 97, 98, or 99% identical to SEQ ID NO:23, a sequence at least 90, 91, 92, 93, 94, 95, 96, 97, 98, or 99% identical to SEQ ID NO:25, or sequence at least 90, 91, 92, 93, 94, 95, 96, 97, 98, or 99% identical to SEQ ID NO:27. In one aspect the nucleic acid sequence comprises a sequence at least 90, 91, 92, 93, 94, 95, 96, 97, 98, or 99% identical to SEQ ID NO:21, a sequence at least 90, 91, 92, 93, 94, 95, 96, 97, 98, or 99% identical to SEQ ID NO:23, a sequence at least 90, 91, 92, 93, 94, 95, 96, 97, 98, or 99% identical to SEQ ID NO:25, and sequence at least 90, 91, 92, 93, 94, 95, 96, 97, 98, or 99% identical to SEQ ID NO:27.

In one aspect the nucleic acid sequence encoding a bispecific binding protein as described herein comprises SEQ ID NO:21, SEQ ID NO:23, SEQ ID NO:25, and SEQ ID NO:27.

In one aspect, the disclosure provides a nucleic acid sequence encoding a bispecific binding protein as described herein, where the nucleic acid sequence comprises one or more of: a sequence at least 90, 91, 92, 93, 94, 95, 96, 97, 98, or 99% identical to SEQ ID NO:22, a sequence at least 90, 91, 92, 93, 94, 95, 96, 97, 98, or 99% identical to SEQ ID NO:24, a sequence at least 90, 91, 92, 93, 94, 95, 96, 97, 98, or 99% identical to SEQ ID NO:26, or sequence at least 90, 91, 92, 93, 94, 95, 96, 97, 98, or 99% identical to SEQ ID NO:28. In one aspect the nucleic acid sequence comprises a sequence at least 90, 91, 92, 93, 94, 95, 96, 97, 98, or 99% identical to SEQ ID NO:22, a sequence at least 90, 91, 92, 93, 94, 95, 96, 97, 98, or 99% identical to SEQ ID NO:24, a sequence at least 90, 91, 92, 93, 94, 95, 96, 97, 98, or 99% identical to SEQ ID NO:26, and sequence at least 90, 91, 92, 93, 94, 95, 96, 97, 98, or 99% identical to SEQ ID NO:28.

In one aspect the nucleic acid sequence encoding a bispecific binding protein as described herein comprises SEQ ID NO:22, SEQ ID NO:24, SEQ ID NO:26, and SEQ ID NO:28.

In one aspect, the disclosure provides a host cell comprising a nucleic acid as described herein. In one aspect, the disclosure provides a host cell comprising a vector comprising a nucleic acid as described herein. In one aspect the disclosure provides a host cell having a nucleic acid as described herein integrated into its genome.

In one aspect, the disclosure provides a host cell comprising a vector comprising a nucleic acid sequence at least 90, 91, 92, 93, 94, 95, 96, 97, 98, or 99% identical to SEQ ID NO:21, a nucleic acid sequence at least 90, 91, 92, 93, 94, 95, 96, 97, 98, or 99% identical to SEQ ID NO:23, a nucleic acid sequence at least 90, 91, 92, 93, 94, 95, 96, 97, 98, or 99% identical to SEQ ID NO:25, and/or a nucleic acid sequence at least 90, 91, 92, 93, 94, 95, 96, 97, 98, or 99% identical to SEQ ID NO:27.

In one aspect, the disclosure provides a host cell comprising a vector comprising a nucleic acid sequence at least 90, 91, 92, 93, 94, 95, 96, 97, 98, or 99% identical to SEQ ID NO:22, a nucleic acid sequence at least 90, 91, 92, 93, 94, 95, 96, 97, 98, or 99% identical to SEQ ID NO:24, a nucleic acid sequence at least 90, 91, 92, 93, 94, 95, 96, 97, 98, or 99% identical to SEQ ID NO:26, and/or a nucleic acid sequence at least 90, 91, 92, 93, 94, 95, 96, 97, 98, or 99% identical to SEQ ID NO:28.

In one aspect, the disclosure provides a bispecific binding protein produced by a host cell as described herein.

The term "native Fc" as used herein refers to a molecule comprising the sequence of a non-antigen binding fragment resulting from digestion of an antibody or produced by other means, whether in monomeric or multimeric form, and can contain the hinge region. The original immunoglobulin source of the native Fc is preferably of human origin and can be any of the immunoglobulins. Native Fc molecules are made up of monomeric polypeptides that can be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, and IgE) or subclass (e.g., IgG1, IgG2, IgG3, IgA1, and IgGA2). One example of a native Fc is a disulfide-bonded dimer resulting from papain digestion of an IgG. The term "native Fc" as used herein is generic to the monomeric, dimeric, and multimeric forms.

In some aspects, the Fc region is or includes a domain that is one or more of an Fc region from an IgG1, IgG2, IgG3, IgG4, IgA, IgM, IgE, or IgD. In some aspects, the antibody is an IgG1 antibody.

The term "Fc variant" as used herein refers to a molecule or sequence that is modified from a native Fc but still comprises a binding site for the salvage receptor, FcRn (neonatal Fc receptor). Exemplary Fc variants, and their interaction with the salvage receptor, are known in the art. Thus, the term "Fc variant" can comprise a molecule or sequence that is humanized from a non-human native Fc.

Furthermore, a native Fc comprises regions that can be removed or mutated to produce an Fc variant to alter certain residues that provide structural features or biological activity that are not required for the binding proteins of the disclosure. Thus, the term "Fc variant" comprises a molecule or sequence that lacks one or more native Fc sites or residues, or in which one or more Fc sites or residues has been modified, that affect or are involved in: (1) disulfide bond formation, (2) incompatibility with a selected host cell, (3) N-terminal heterogeneity upon expression in a selected host cell, (4) glycosylation, (5) interaction with complement, (6) binding to an Fc receptor other than a salvage receptor, or (7) antibody-dependent cellular cytotoxicity (ADCC).

In some aspects, the bispecific binding protein comprises an variant Fc region comprising at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R, 243W, 243L 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 434W, 434Y, 436H, 440Y and 443W as numbered by the EU index as set forth in Kabat.

In some aspects, the variant Fc region comprises one or more modifications at positions selected from 428 and 434 as numbered by the EU index as set forth in Kabat. In some aspects, the variant Fc region comprises one or more amino acid substitutions at positions selected from 428 and 434 as numbered by the EU index as set forth in Kabat. In some aspects, the variant Fc region comprises one or more amino acid substitutions selected from 428L, 428F, 434A, 434W, and 434Y.

Fc region engineering is widely used in the art to extend the half-life of therapeutic antibodies and protect from degradation in vivo. In some aspects, the Fc region of an IgG antibody or antigen-binding fragment can be modified in order to increase the affinity of the IgG molecule for the Fc Receptor-neonate (FcRn), which mediates IgG catabolism and protects IgG molecules from degradation.

Other suitable Fc region amino acid substitutions or modifications are known in the art and include, for example, the triple substitution methionine (M) to tyrosine (Y) substitution in position 252, a serine (S) to threonine (T) substitution in position 254, and a threonine (T) to glutamic acid (E) substitution in position 256, numbered according to the EU index as in Kabat (M252Y/S254T/T256E; referred to as "YTE" or "YTE mutation") (see, e.g., U.S. Pat. No. 7,658,921; U.S. Patent Application Publication 2014/0302058; and Yu et al., Antimicrob. Agents Chemother., 61(1): e01020-16 (2017), each of which is herein incorporated by reference in its entirety).

In some aspects, the antibody or antigen-binding fragment thereof comprises an Fc region that has been engineered to improve half-life. In some aspects, the antibody or antigen-binding fragment thereof comprises an Fc region with a YTE mutation.

In some aspects, the Fc region is aglycosylated. In some aspects, the Fc region is deglycosylated. In some aspects, the Fc region has reduced fucosylation or is afucosylated.

In some aspects, the Fc variant antibody or binding fragment thereof has an increased binding affinity for FcRn.

The triple mutation (TM) L234F/L235E/P331S (according to European Union numbering convention; Sazinsky et al. Proc Natl Acad Sci USA, 105:20167-20172 (2008)) in the heavy chain constant region can significantly reduce IgG effector function. In some aspects, the antibody or antigen-binding fragment thereof comprises an Fc region with a L234F/L235E/P331S triple mutation (TM).

In some aspects, the Fc variant antibody or binding fragment thereof has reduced complement dependent cytotoxicity (CDC) when administered in vivo. In some aspects, the Fc variant antibody or binding fragment thereof has reduced CDC compared to an antibody or binding variant thereof that contains a wild-type Fc region. In some aspects, the Fc variant antibody or binding fragment thereof does not trigger CDC when administered in vivo. In some aspects, the Fc variant antibody or binding fragment thereof causes reduced CDC when administered in vivo. In some aspects, the Fc variant antibody or binding fragment thereof having reduced CDC activity or no CDC activity comprises the triple mutation (L234F/L235E/P331S) in the variant Fc region.

In some aspects, the Fc variant antibody or binding fragment thereof has reduced antibody dependent cellular cytotoxicity (ADCC) when administered in vivo. In some aspects, the Fc variant antibody or binding fragment thereof has reduced ADCC compared to an antibody or binding variant thereof that contains a wild-type Fc region. In some aspects, the Fc variant antibody or binding fragment thereof does not trigger ADCC when administered in vivo. In some aspects, the Fc variant antibody or binding fragment thereof causes reduced ADCC when administered in vivo. In some aspects, the Fc variant antibody or binding fragment thereof having reduced ADCC activity or no ADCC activity comprises the triple mutation (L234F/L235E/P331S) in the variant Fc region.

In some aspects, the antibody or binding fragment thereof having reduced CDC activity has reduced toxicity when administered to a subject. In some aspects, the antibody or binding fragment thereof having reduced ADCC activity has reduced toxicity when administered to a subject.

The term "Fc domain" as used herein encompasses native Fc and Fc variants and sequences as defined above. As with Fc variants and native Fc molecules, the term "Fc domain" includes molecules in monomeric or multimeric form, whether digested from whole antibody or produced by other means.

To improve the yields of the binding proteins, the $C_{H3}$ domains can be altered by the "knob-into-holes" technology which is described in detail with several exemplary molecules in, for example, International Publication No. WO 96/027011, Ridgway et al., 1996, *Protein Eng.* 9: 617-21; and Merchant et al., 1998, *Nat. Biotechnol.* 16: 677-81. Specifically, the interaction surfaces of the two $C_{H3}$ domains are altered to increase the heterodimerization of both heavy chains containing these two $C_{H3}$ domains. Each of the two $C_{H3}$ domains (of the two heavy chains) can be the "knob," while the other is the "hole." The introduction of a disulfide bridge further stabilizes the heterodimers (Merchant et al., 1998; Atwell et al., 1997, *J. Mol. Biol.* 270: 26-35) and increases the yield.

In some aspects, the binding proteins have a "DuetMab" format. DuetMab has the following basic structure: an Fc region having a modified heavy chain, wherein the $C_{H1}$ region of the modified heavy chain has a substitution of a native cysteine to a non-cysteine amino acid, and a substitution of a native non-cysteine amino acid to a cysteine amino acid; a modified corresponding light chain, where the $C_L$ region of the modified light chain also has a substitution of a native cysteine to a non-cysteine amino acid, and a substitution of a native non-cysteine amino acid to a cysteine amino acid; a second Fc region having a second heavy chain; and second corresponding modified light chain, where the modified heavy chain is directly linked to the corresponding modified light chain, and on a separate target binding arm, the second heavy chain is directly linked to the second corresponding light chain, and where the substituted cysteine of the modified heavy chain, resulting from the substitution of the native non-cysteine amino acid to the cysteine amino acid, and the substituted cysteine of the modified corresponding light chain, resulting from the substitution of the native non-cysteine amino acid to the cysteine amino acid, can form a disulphide bond. Disclosure related to DuetMab can found, for example, in U.S. Pat. No. 9,527,927 or U.S. Pat. No. 11,279,759, both incorporated herein by reference in their entirety.

The term "$K_D$," as used herein, refers to the dissociation constant ($K_D=[A]\times[B]/[AB]$) of the interaction between a binding protein the disclosure and an antigen target and has the units of moles/liter. A binding protein of the disclosure typically has a dissociation constant ($K_D$) of $10^{-5}$ to $10^{-12}$ moles/liter or less, or $10^{-7}$ to $10^{-12}$ moles/liter or less, or $10^{-3}$ to $10^{-12}$ moles/liter, and/or with a binding affinity of at least $10^7$ M$^{-1}$, or at least $10^8$ M$^{-1}$, or at least $10^9$ M$^{-1}$, or at least $10^{12}$ M$^{-1}$. Any $K_D$ value greater than $10^{-4}$ moles/liter is generally considered to indicate non-specific binding. Therefore, the lower the $K_D$ value, the greater the affinity. In some aspects, a binding protein of the disclosure will bind to a desired antigen with an affinity less than 500 nM, or less than 200 nM, or less than 10 nM, or less than 500 pM. High affinity or very strong binding is often associated with greater efficacy, but it is not always the case that the greater the affinity the greater the efficacy.

The dissociation constant ($K_D$) can be determined, for example, by surface plasmon resonance (SPR). Generally, surface plasmon resonance analysis measures real-time binding interactions (both on rate and off rate) between a ligand (a target antigen on a biosensor matrix) and an analyte by surface plasmon resonance using, for example, the BIAcore® system (Pharmacia Biosensor; Piscataway, NJ). Surface plasmon analysis can also be performed by immobilizing the analyte and presenting the ligand. Specific binding of binding protein of the disclosure to an antigen or antigenic determinant can also be determined in any suitable manner known in the art, including, for example, Scatchard analysis and/or competitive binding assays, such as radioimmunoassays (RIA), enzyme linked immunosorbent assays (ELISA), enzyme immunoassays (EIA), and sandwich competition assays.

In one aspect, the equilibrium dissociation constant ($K_D$) of an interaction of a bispecific binding protein as described herein with human TIGIT is less than or equal to about 15 pM. In one aspect, the $K_D$ of an interaction of a bispecific binding protein as described herein with human TIGIT is less than or equal to about 9 pM. In one aspect, the $K_D$ of an interaction of a bispecific binding protein as described herein with human TIGIT is less than or equal to about 15, 14, 13, 12, 11, 10, 9, or 8 pM.

In one aspect, the $K_D$ of an interaction of a bispecific binding protein as described herein with human TIGIT is from about 9 pM to about 15 pM. In one aspect, the $K_D$ of an interaction of a bispecific binding protein as described herein with human TIGIT is from about 10 pM to about 15 pM. In one aspect, the $K_D$ of an interaction of a bispecific binding protein as described herein with human TIGIT is from about 11 pM to about 15 pM. In one aspect, the $K_D$ of an interaction of a bispecific binding protein as described herein with human TIGIT is from about 12 pM to about 15 pM. In one aspect, the $K_D$ of an interaction of a bispecific binding protein as described herein with human TIGIT is from about 13 pM to about 15 pM. In one aspect, the $K_D$ of an interaction of a bispecific binding protein as described herein with human TIGIT is from about 14 pM to about 15 pM.

In one aspect, the $K_D$ of an interaction of a bispecific binding protein as described herein with human PD-L1 is less than or equal to about 0.4 nM. In one aspect, the $K_D$ of an interaction of a bispecific binding protein as described herein with human PD-L1 is from about 0.2 nM to about 0.5 nM. In one aspect, the $K_D$ of an interaction of a bispecific binding protein as described herein with human PD-L1 is from about 0.3 nM to about 0.5 nM. In one aspect, the $K_D$ of an interaction of a bispecific binding protein as described herein with human PD-L1 is from about 0.4 nM to about 0.5 nM.

In particular aspects provided herein is a method of treating a subject having a disease or condition comprising administering to the subject a therapeutically effective amount of the binding proteins disclosed herein. The disclosure provides methods of inducing an immune response in a subject as well as methods for treating or preventing a tumor and/or cancer in a subject by administering the proteins, nucleic acid molecules and/or compositions to the subject.

In particular aspects provided herein is a method of inducing an immune response in a subject comprising administering to the subject a bispecific protein as described herein. In one aspect, provided herein is a method of inducing an immune response in a subject comprising administering to the subject a nucleic acid as described herein. In one aspect, provided herein is a method of inducing an immune response in a subject comprising administering to the subject a pharmaceutical composition as described herein.

In one aspect, provided herein is a bispecific protein as defined herein for use in therapy. In one aspect, provided herein is a bispecific protein as defined herein for use in the treatment of cancer. In one aspect, provided herein is the use of a bispecific protein as defined herein in the manufacture of a medicament for the treatment of cancer. In one aspect, provided herein is a nucleic acid as defined herein for use in therapy. In one aspect, provided herein is a nucleic acid as defined herein for use in the treatment of cancer. In one aspect, provided herein is the use of a nucleic acid as defined herein in the manufacture of a medicament for the treatment of cancer.

In one aspect, the method of treating comprises administering to the subject a therapeutically effective amount of the binding proteins disclosed herein in combination with an additional anti-cancer compound. In some aspects, the anti-cancer compound is a small molecule drug. In some aspects, the anti-cancer compound is pemetrexed, carboplatin, gemcitabine, cisplatin, paclitaxel or combinations thereof. In some aspects, the binding protein and additional anti-cancer treatment are administered simultaneously. In some aspects, the binding protein and additional anti-cancer treatment are not administered simultaneously but are administered during the same course of treatment.

A "disease" or "condition" refers to any condition that would benefit from treatment using the methods of the disclosure. "Disease" and "condition" are used interchangeably herein and include chronic and acute disorders or diseases, including those pathological conditions that predispose a patient to the disorder in question. In some aspects, the disease is a tumor. In some aspects, the disease is a solid tumor. In some aspects, the disease is cancer. In some aspects, the cancer is one or more of ovarian cancer, breast cancer, colorectal cancer, prostate cancer, cervical cancer, uterine cancer, testicular cancer, bladder cancer, head and neck cancer, melanoma, pancreatic cancer, renal cell carcinoma, and lung cancer. In some aspects, the disease is non-small cell lung cancer (NSCLC). In some aspects, the NSCLC is advanced or metastatic. In some aspects, the advanced NSCLC is stage III or stage IV NSCLC.

The term "subject" is intended to include human and non-human animals, particularly mammals. In certain aspects, the subject is a human patient.

The terms "treatment" or "treat" as used herein refer to both therapeutic treatment and prophylactic or preventative measures. Those in need of treatment include subjects having a disease or condition as well as those prone to having disease or condition or those for which a disease or condition is to be prevented.

The terms "administration" or "administering" as used herein refer to providing, contacting, and/or delivering a compound or compounds by any appropriate route to achieve the desired effect. Administration may include, but is not limited to, oral, sublingual, parenteral (e.g., intravenous, subcutaneous, intracutaneous, intramuscular, intraarticular, intraarterial, intrasynovial, intrasternal, intrathecal, intralesional, or intracranial injection), transdermal, topical, buccal, rectal, vaginal, nasal, ophthalmic, via inhalation, and implants.

The terms "co-administered" or "in combination" as used herein refer to simultaneous or sequential administration of multiple compounds or agents. A first compound or agent may be administered before, concurrently with, or after administration of a second compound or agent. The first compound or agent and the second compound or agent may be simultaneously or sequentially administered on the same day, or may be sequentially administered within 1 day, 2 days, 3 days, 4 days, 5 days, 6 days, 1 week, 2 weeks, 3 weeks, or 1 month of each other. In some aspects, compounds or agents are co-administered during the period in which each of the compounds or agents are exerting at least some physiological effect and/or has remaining efficacy.

The terms "pharmaceutical composition" or "therapeutic composition" as used herein refer to a compound or composition capable of inducing a desired therapeutic effect when properly administered to a subject. In some aspects, the disclosure provides a pharmaceutical composition comprising a pharmaceutically acceptable carrier and a therapeutically effective amount of binding proteins of the disclosure.

A "therapeutically effective dose" or "therapeutic dose" is an amount sufficient to effect desired clinical results (i.e., achieve therapeutic efficacy). A therapeutically effective dose can be administered in one or more administrations.

The terms "pharmaceutically acceptable carrier" or "physiologically acceptable carrier" as used herein refer to one or more formulation materials suitable for accomplishing or enhancing the delivery of one or more binding proteins of the disclosure.

In some aspects, the binding proteins disclosed herein may be formulated with a pharmaceutically acceptable carrier, excipient, or stabilizer, as pharmaceutical compositions. In certain aspects, such pharmaceutical compositions are suitable for administration to a human or non-human animal via any one or more routes of administration using methods known in the art. The term "pharmaceutically acceptable carrier" means one or more non-toxic materials that do not interfere with the effectiveness of the biological activity of the active ingredients. Such preparations may routinely contain salts, buffering agents, preservatives, compatible carriers, and optionally other therapeutic agents. Such pharmaceutically acceptable preparations may also contain compatible solid or liquid fillers, diluents or encapsulating substances which are suitable for administration into a human. Other contemplated carriers, excipients, and/or additives, which may be utilized in the formulations described herein include, for example, flavoring agents, antimicrobial agents, sweeteners, antioxidants, antistatic agents, lipids, protein excipients such as serum albumin, gelatin, casein, salt-forming counterions such as sodium, and the like. These and additional known pharmaceutical carriers, excipients, and/or additives suitable for use in the formulations described herein are known in the art, for example, as listed in "Remington: The Science & Practice of Pharmacy," 21st ed., Lippincott Williams & Wilkins, (2005), and in the "Physician's Desk Reference," 60th ed., Medical Economics, Montvale, N.J. (2005). Pharmaceutically acceptable carriers can be selected that are suitable for the mode of administration, solubility, and/or stability desired or required.

In some aspects, the pharmaceutical compositions of the disclosure include an additional anti-cancer compound. In some aspects, the anti-cancer compound is a small molecule drug. In some aspects, the anti-cancer compound is pemetrexed, carboplatin, gemcitabine, cisplatin, paclitaxel or combinations thereof. In some aspects, the anti-cancer compound is pemetrexed. In some aspects, the anti-cancer compound is carboplatin. In some aspects, the anti-cancer compound is gemcitabine. In some aspects, the anti-cancer compound is cisplatin. In some aspects, the anti-cancer compound is paclitaxel.

In one aspect, the formulations of the disclosure are pyrogen-free formulations that are substantially free of endotoxins and/or related pyrogenic substances. Endotoxins include toxins that are confined inside a microorganism and are released only when the microorganisms are broken down or die. Pyrogenic substances also include fever-inducing, thermostable substances (glycoproteins) from the outer membrane of bacteria and other microorganisms. Both of these substances can cause fever, hypotension, and shock if administered to humans. Due to the potential harmful effects, even low amounts of endotoxins must be removed from intravenously administered pharmaceutical drug solutions. The Food & Drug Administration ("FDA") has set an upper limit of 5 endotoxin units (EU) per dose per kilogram body weight in a single one-hour period for intravenous drug applications (The United States Pharmacopeial Convention, Pharmacopeial Forum 26(1): 223 (2000)). In certain aspects, the endotoxin and pyrogen levels in the composition are less than 10 EU/mg, or less than 5 EU/mg, or less than 1 EU/mg, or less than 0.1 EU/mg, or less than 0.01 EU/mg, or less than 0.001 EU/mg.

When used for in vivo administration, the formulations of the disclosure should be sterile. The formulations of the disclosure may be sterilized by various sterilization methods, including, for example, sterile filtration or radiation. In one aspect, the formulation is filter sterilized with a presterilized 0.22-micron filter. Sterile compositions for injection can be formulated according to conventional pharmaceutical practice as described in "Remington: The Science & Practice of Pharmacy," 21st ed., Lippincott Williams & Wilkins, (2005).

In some aspects, therapeutic compositions can be formulated for particular routes of administration, such as oral, nasal, pulmonary, topical (including buccal and sublingual), rectal, vaginal, and/or parenteral administration. The terms "parenteral administration" and "administered parenterally" as used herein refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection, and infusion. Formulations of the disclosure that are suitable for topical or transdermal administration include powders, sprays, ointments, pastes, creams, lotions, gels, solutions, patches, and inhalants. The antibodies and other actives may be mixed under sterile conditions with a pharmaceutically acceptable carrier, and with any preservatives, buffers, or propellants which may be required (see, e.g., U.S. Pat. Nos. 7,378,110; 7,258,873; and 7,135,180; U.S. Patent Application Publication Nos. 2004/0042972 and 2004/0042971).

The formulations can be presented in unit dosage form and can be prepared by any method known in the art of pharmacy. Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient (e.g., "a therapeutically effective amount"). The selected dosage level will depend upon a variety of pharmacokinetic factors including the activity of the particular compositions employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. These dosages may be administered daily, weekly, biweekly, monthly, or less frequently, for example, biannually, depending on dosage, method of administration, disorder or symptoms to be treated, and individual subject characteristics. Dosages can also be administered via continuous infusion (such as through a pump). The administered dose may also depend on the route of administration. For example, subcutaneous administration may require a higher dosage than intravenous administration. As noted above, any commonly used dosing regimen (e.g., 1-10 mg/kg administered by injection or infusion daily or twice a week) may be adapted and suitable in the methods relating to treating human cancer patients.

All references cited herein, including patents, patent applications, papers, textbooks and the like, and the references cited therein, to the extent that they are not already, are hereby incorporated herein by reference in their entirety.

Without limiting the disclosure, a number of aspects of the disclosure are described herein for purpose of illustration.

EXAMPLES

The Examples that follow are illustrative of specific aspects of the disclosure, and various uses thereof. They are set forth for explanatory purposes only and should not be construed as limiting the scope of the disclosure in any way.

Figure 2:
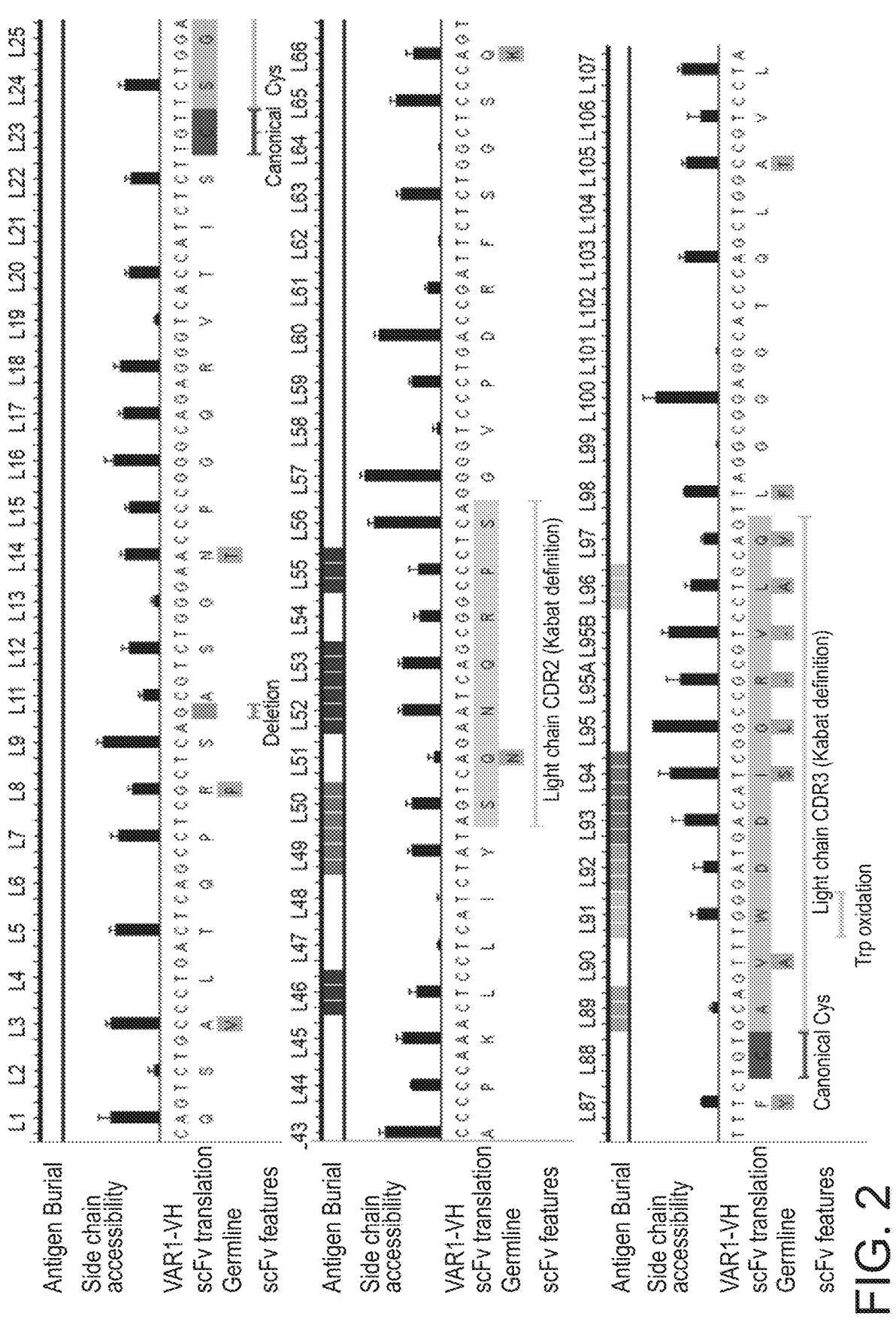
FIG. 2 shows a sequence analysis of the residues identified in the parental VAR1 variable light chain (SEQ ID NO: 36) and nucleic acid (SEQ ID NO: 39).
Figure 2:
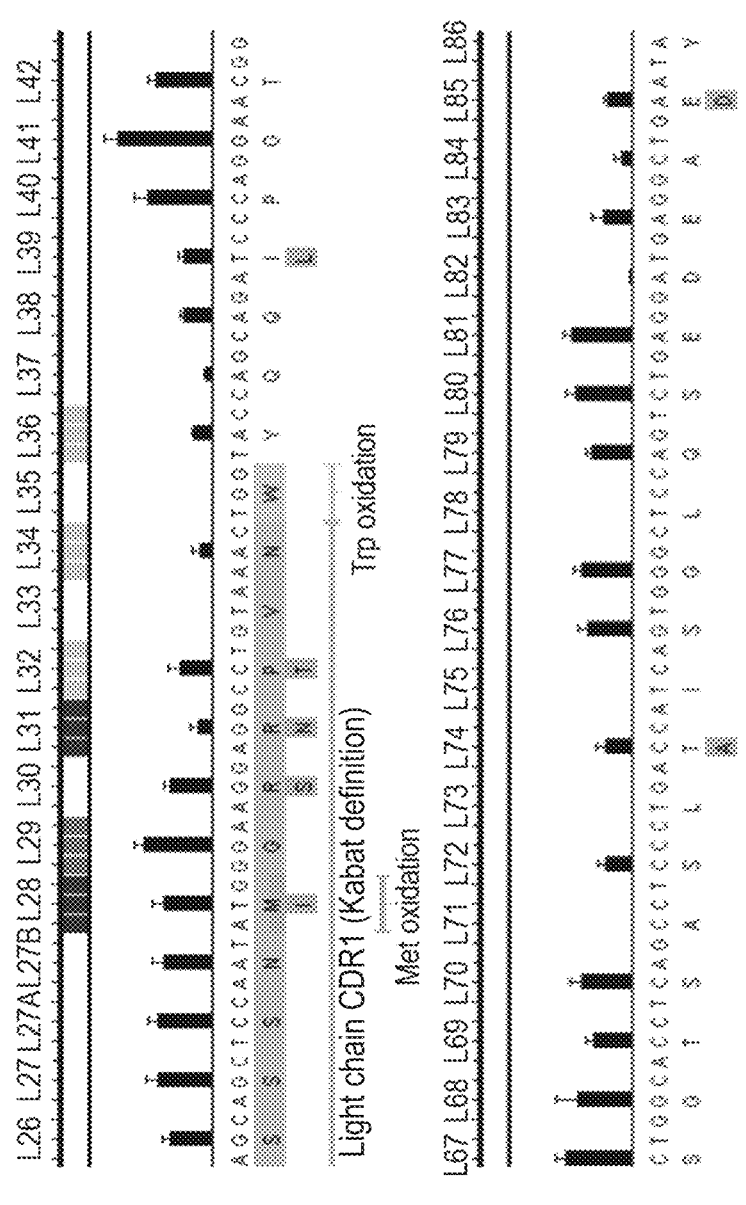
Figure 3B:
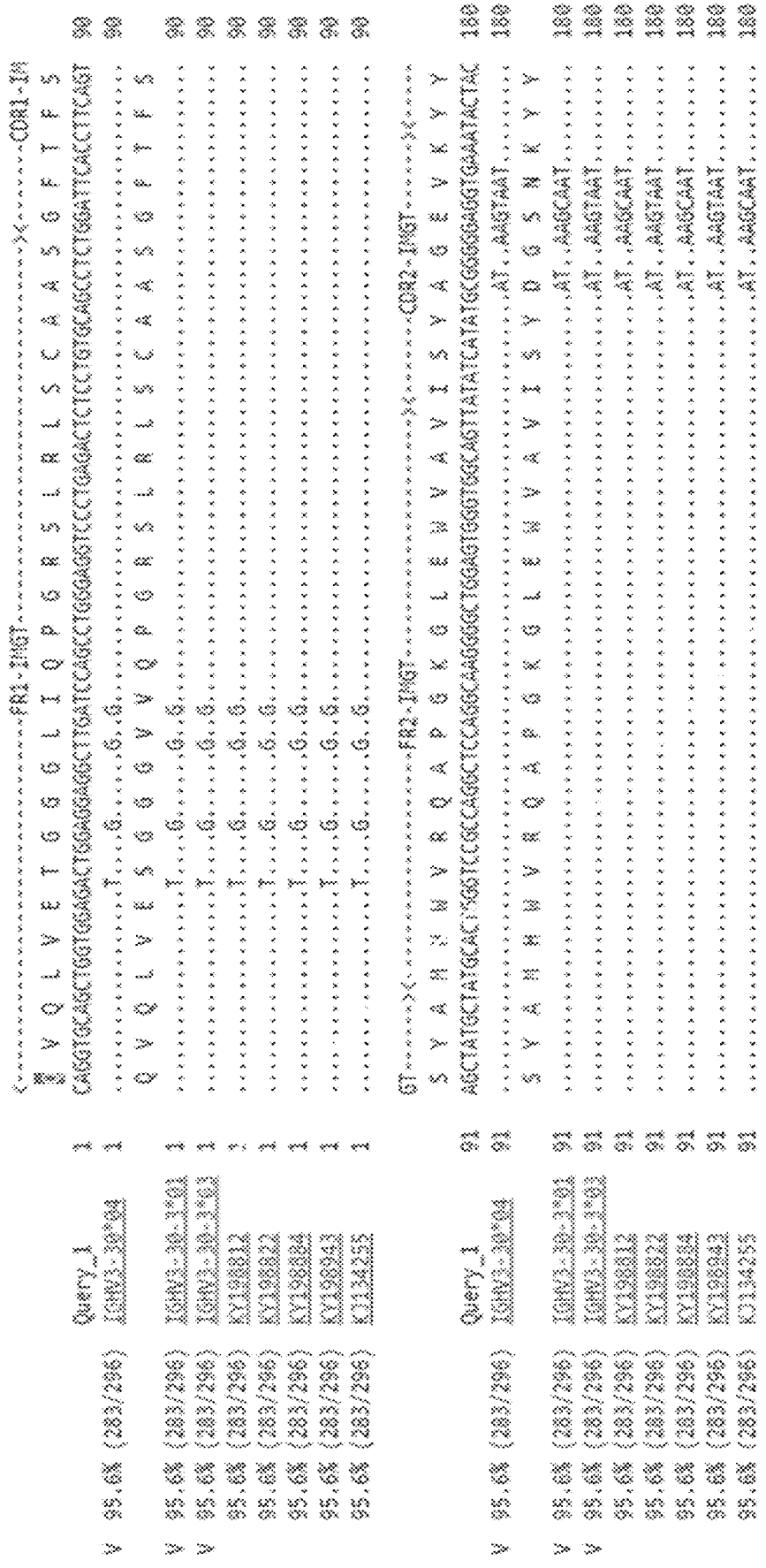
Figure 3B:
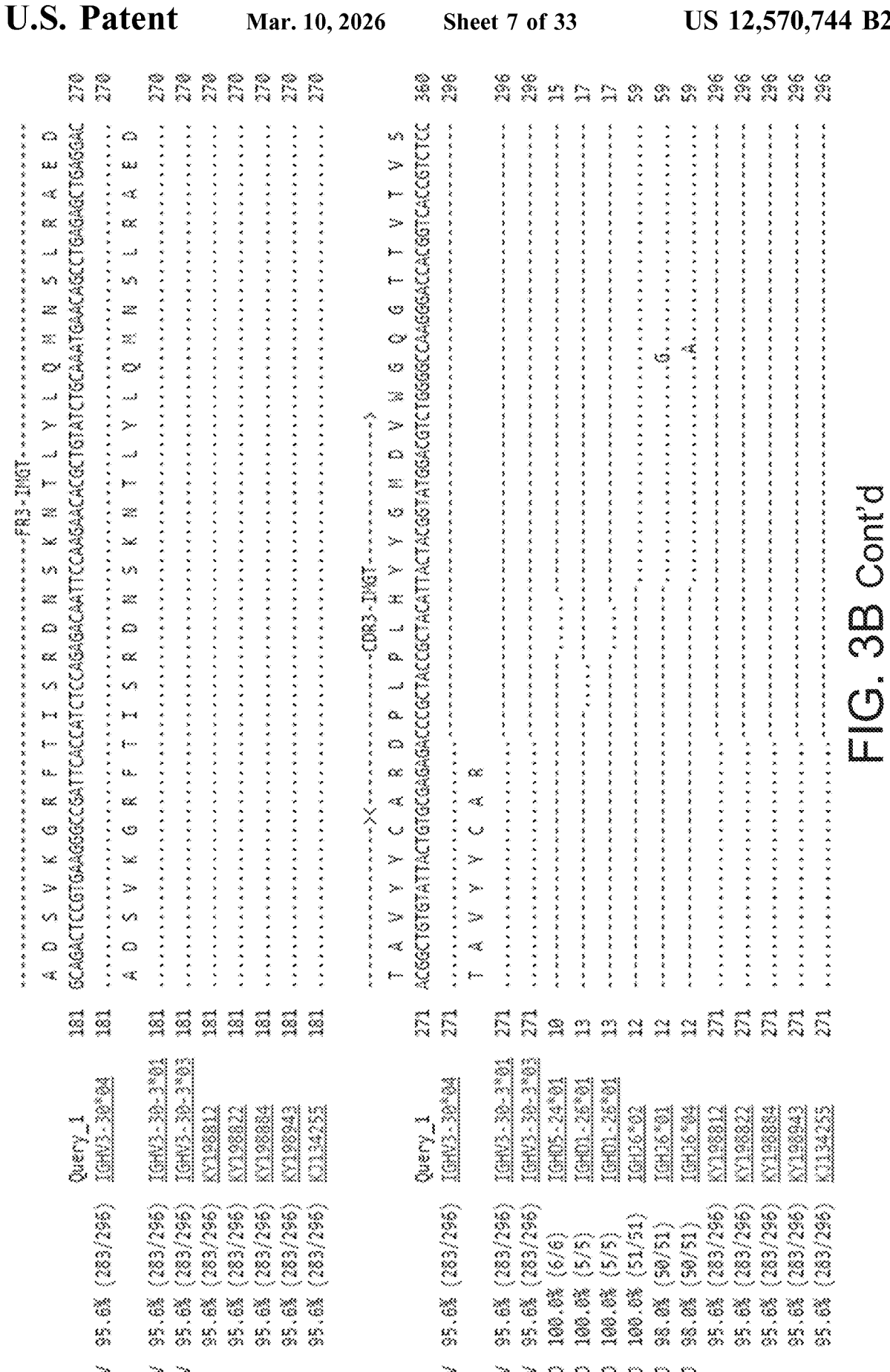
Figure 4A:
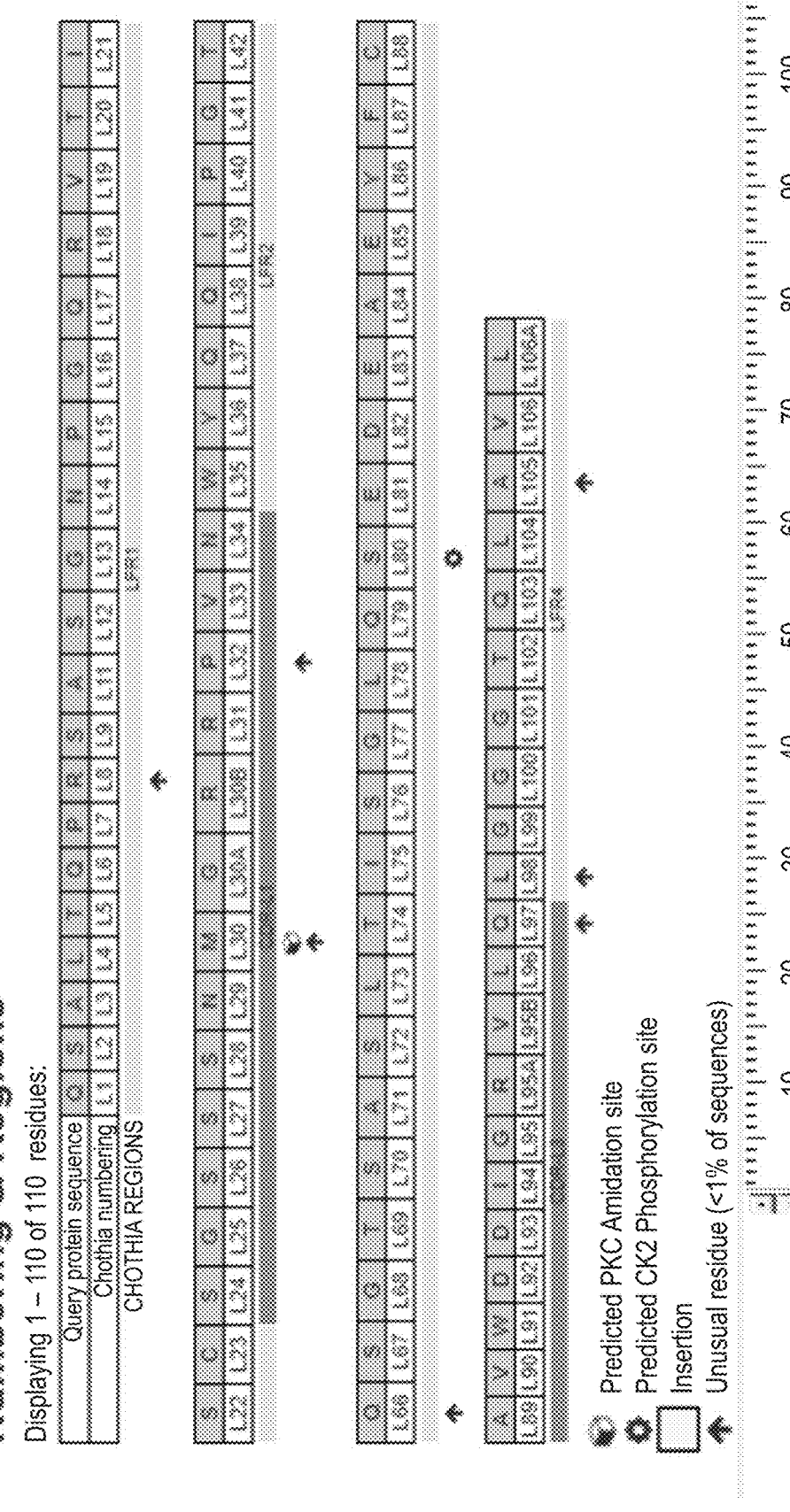

Example 1: Generation and Characterization of Anti-TIGIT Portion of Bispecific Antibodies A series of monoclonal TIGIT antibodies were developed and characterized. The sequences in the parental VAR1 (P-VAR1) WT variable heavy and light chains (VL WT+VH WT) were reviewed. In the variable heavy chain, a potential risk of methionine oxidation was identified in the CDRH3 region and a potential risk of DP fragmentation was identified in the CDRH3 region (FIG. 1). In the variable light chain, a potential risk of methionine oxidation was identified in the CDRL1 region (FIG. 2). Five variant monoclonal antibodies were generated to remove this potential oxidation and to match germline (GL) sequences:

$$VL\ WT + VH\ WT;$$
$$VL\ GL + VH\ WT;$$
$$VL\ WT + VH\ GL;$$
$$VL\ GL + VH\ GL;$$
$$VL\ GL\ (CDRL1\ M\text{-}I) + VH\ GL$$

Figure 5:
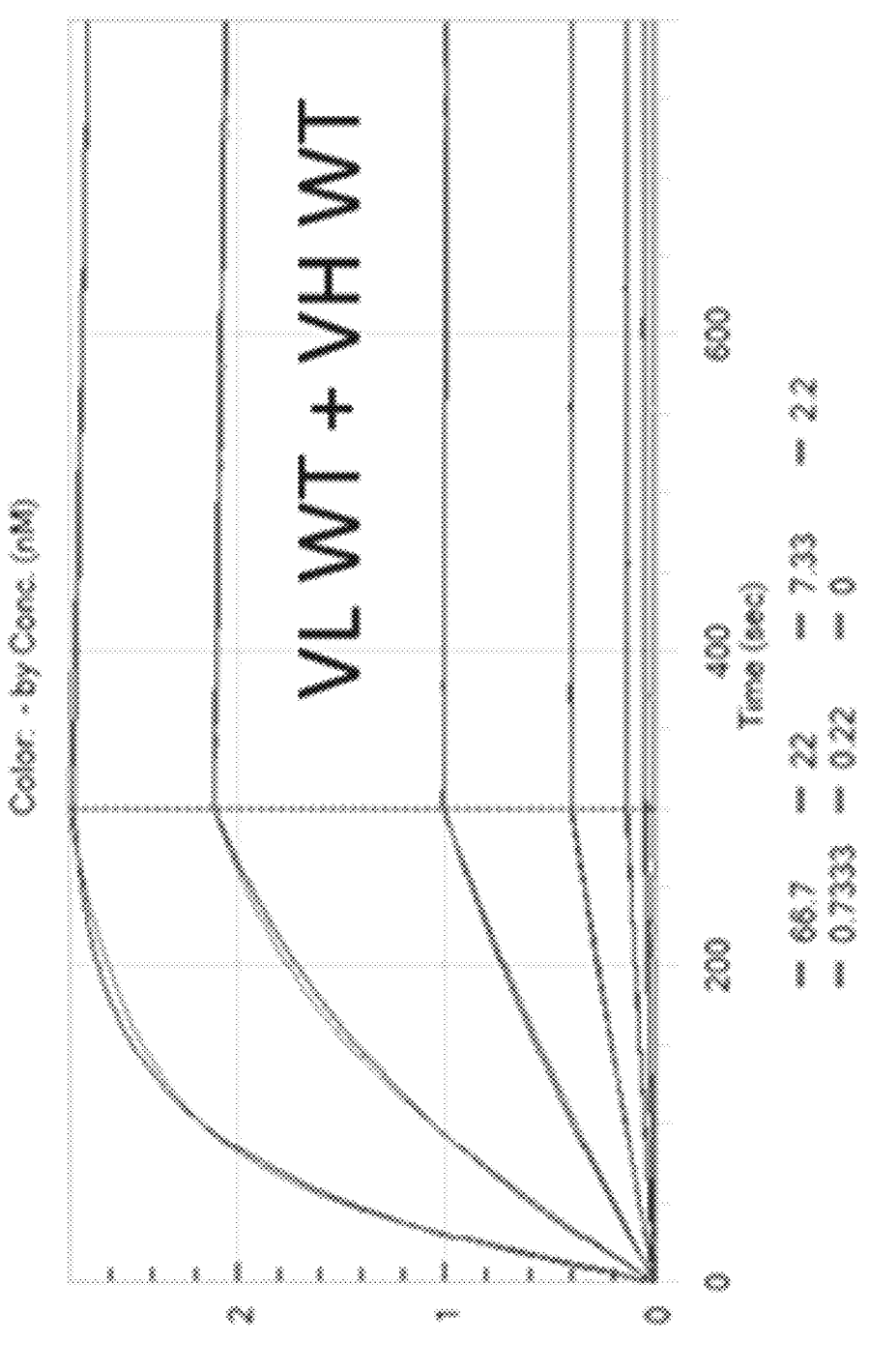
FIG. 5 shows that the VAR1 variants maintained efficient expression and pairing properties.
Figure 5:
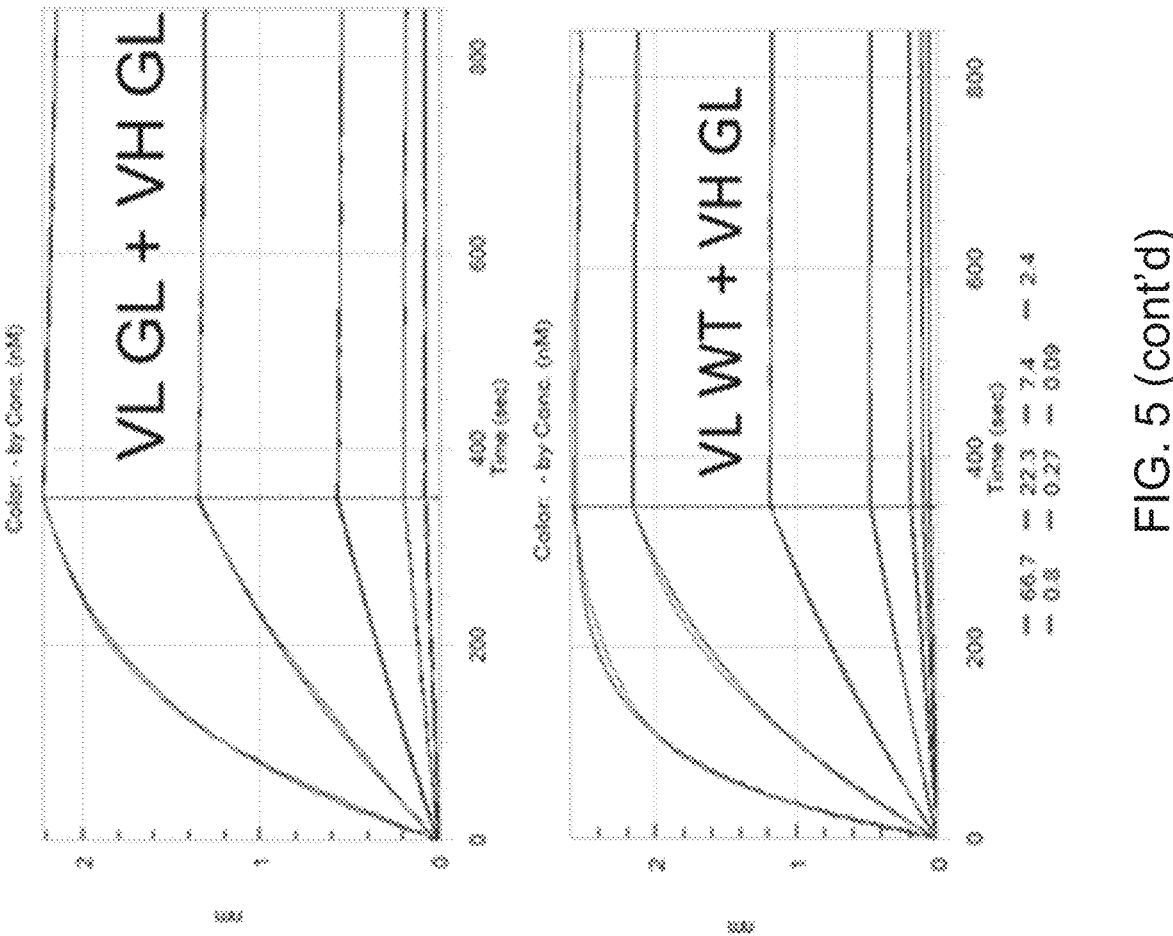
Figure 5:
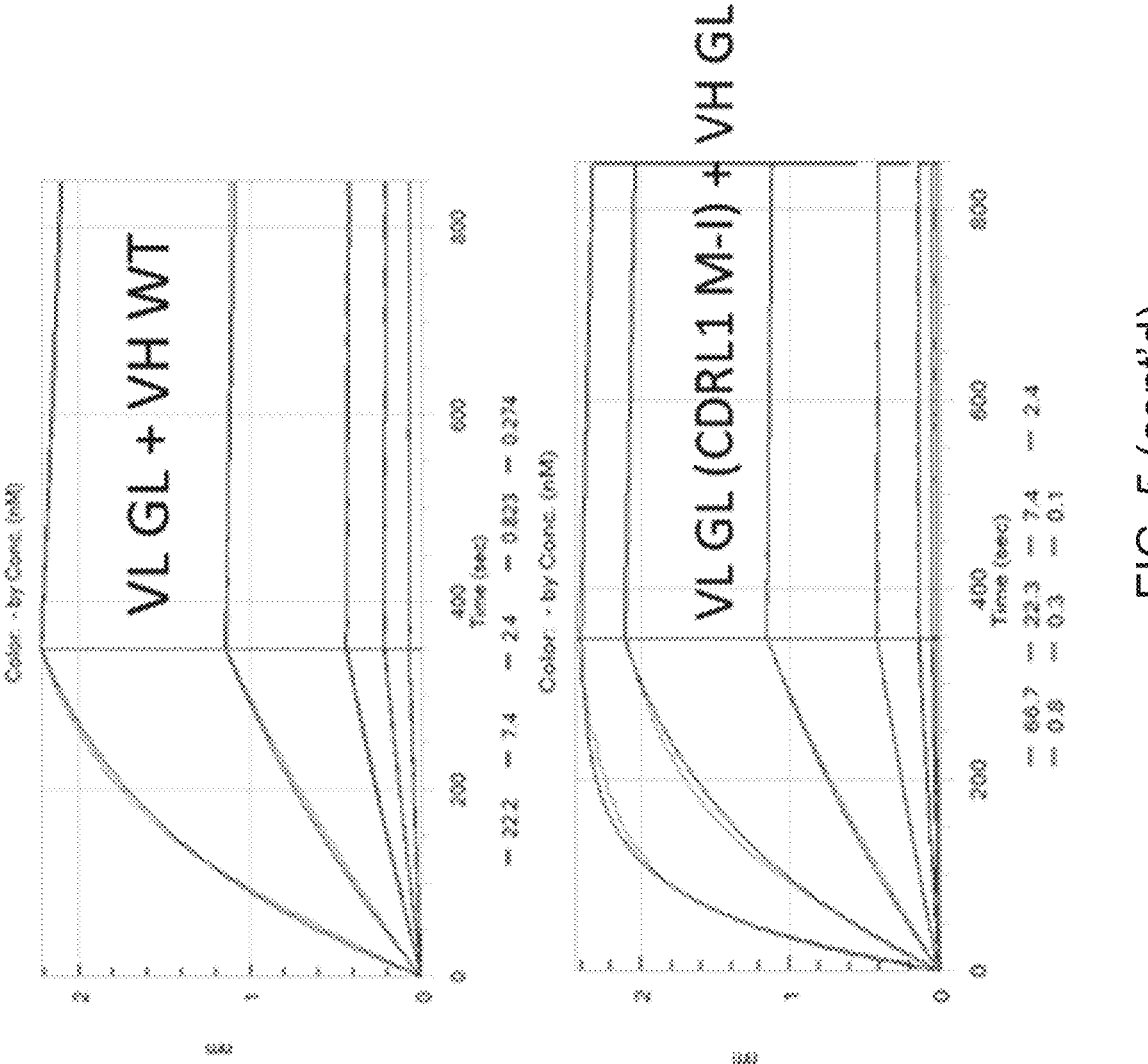
Figure 6A:
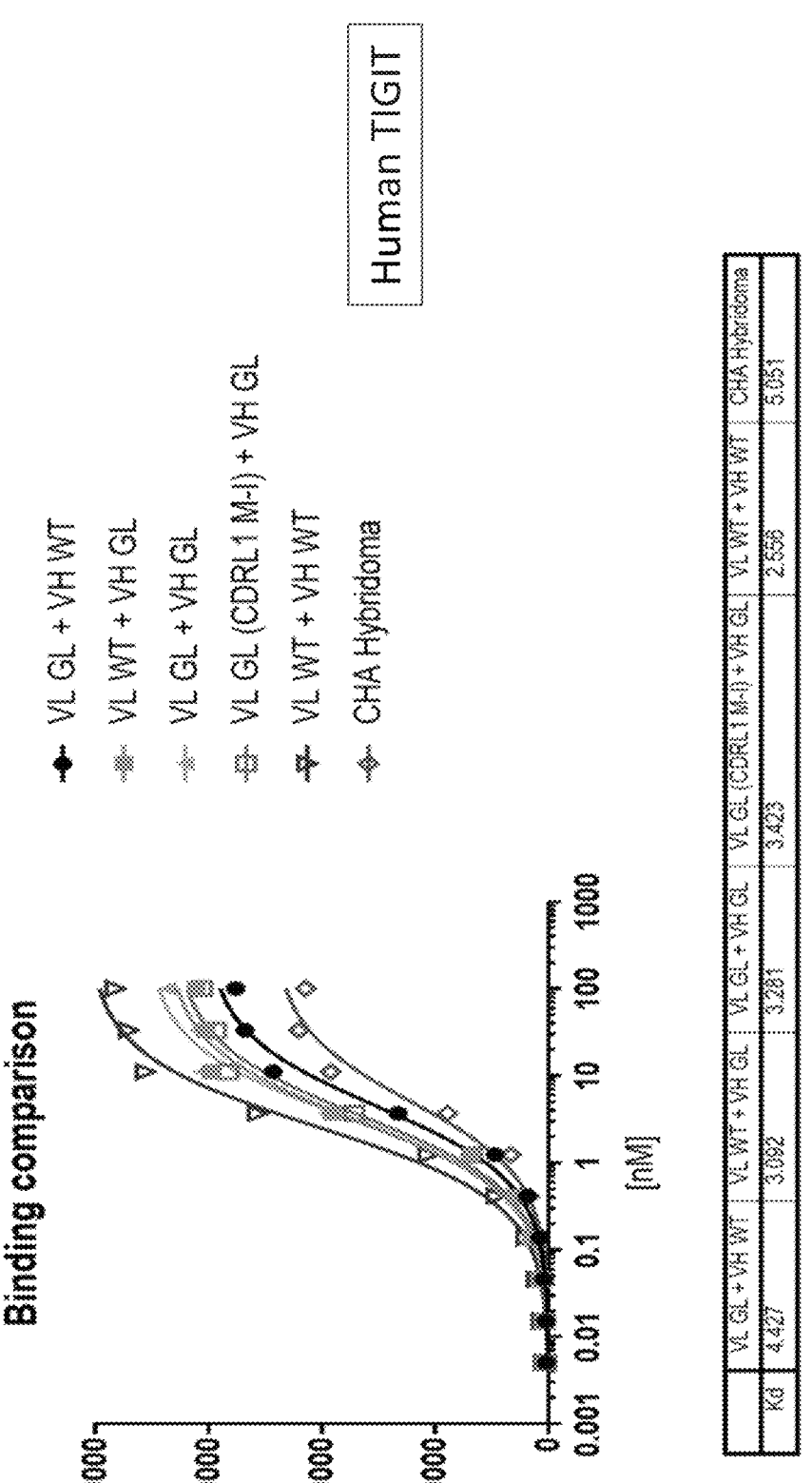
FIGS. 6A and 6B show that the VAR1 variants retained the cell binding properties of the parental mAbs to human and cynomolgus TIGIT OE 293s. Data are presented as median fluorescence intensity (MFI).
Figure 6B:
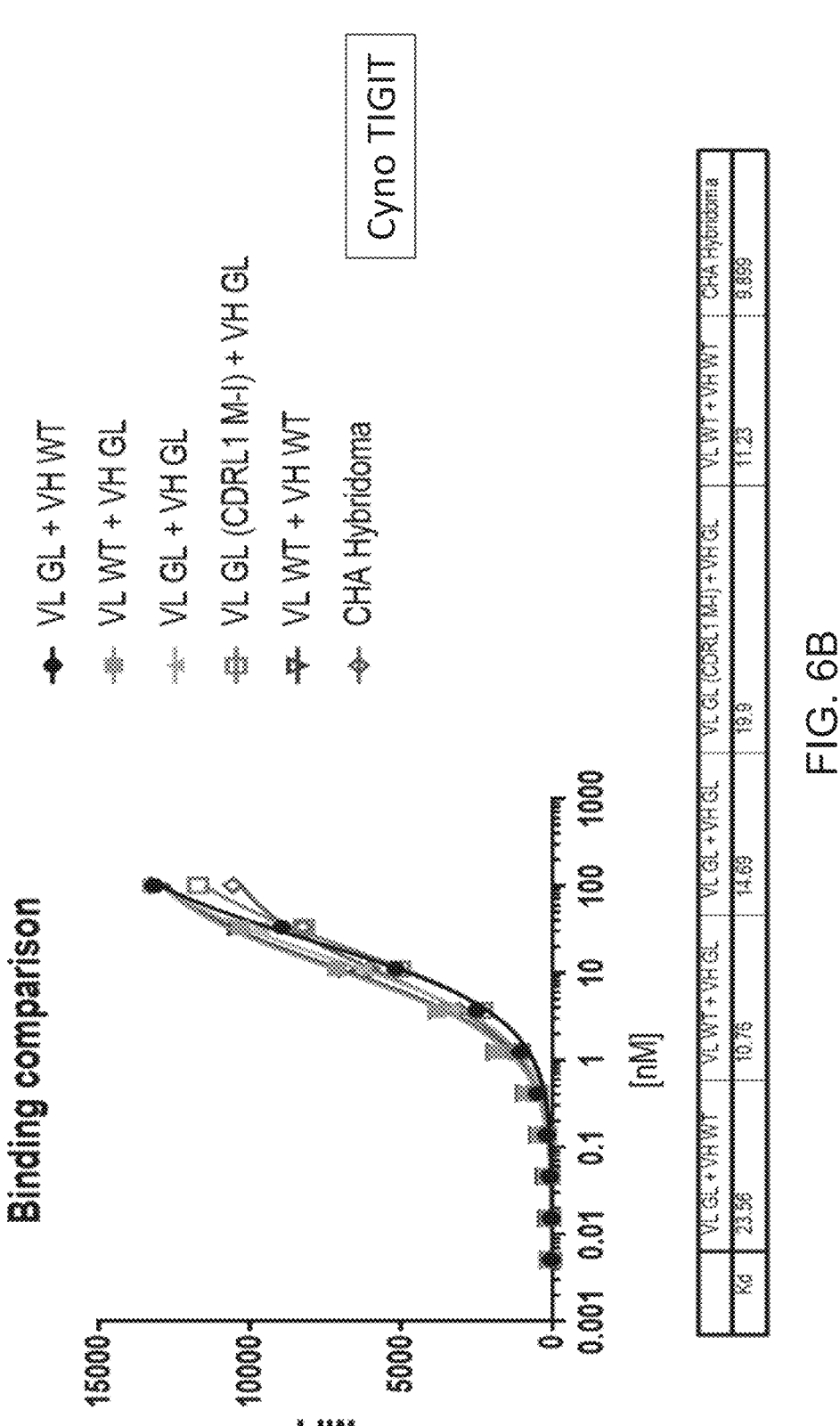
Figure 7:
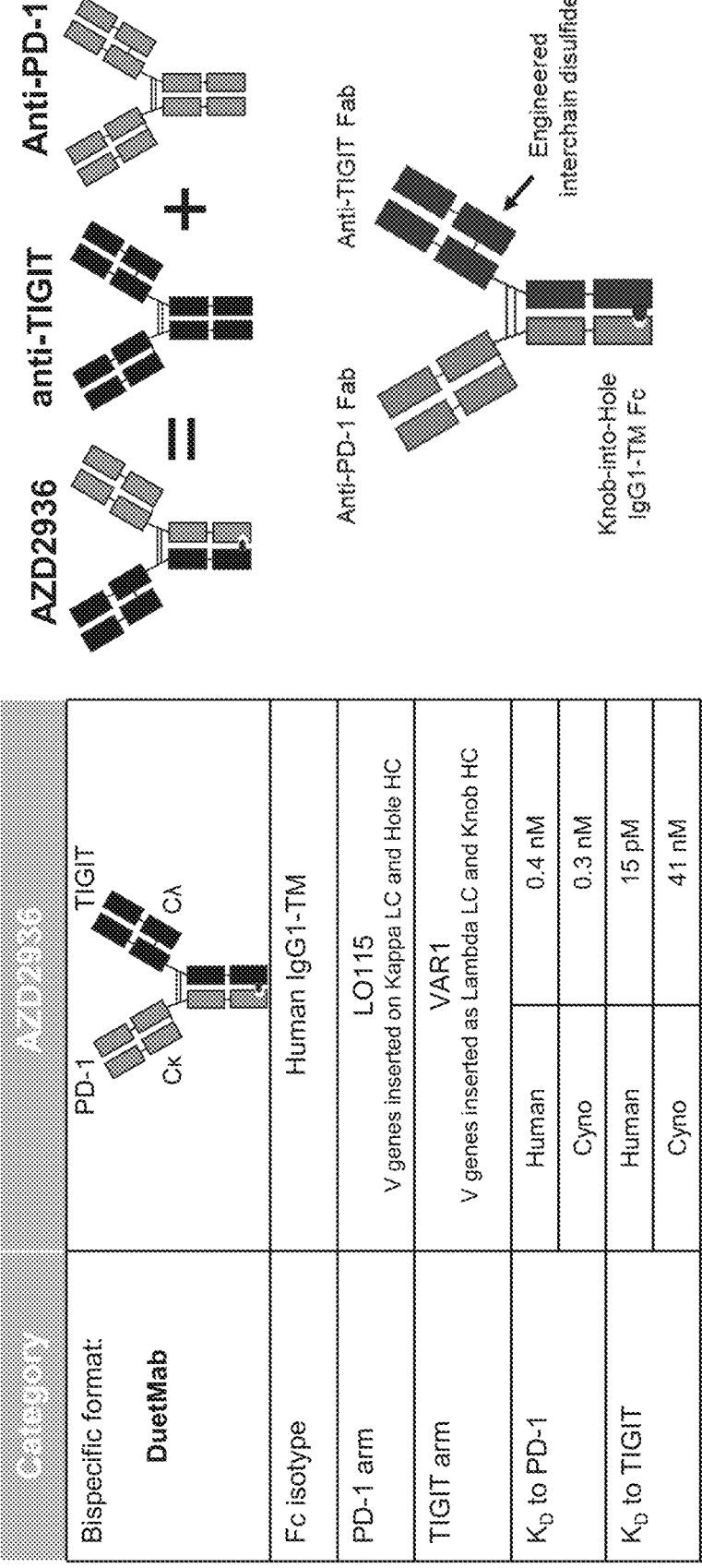
FIG. 7 shows the characteristics and format of particular aspects of the binding proteins disclosed herein.

Specifically, in the variable heavy region, the first E amino acid was mutated to Q to match the germline sequence. In the variable heavy region, the methionine residue in CDRL1 was mutated in one variant to isoleucine as in the germline sequence to mitigate potential oxidation. P-VAR1 VH and VL domains were successfully modified without affecting the productivity and kinetics of the variant. (Table 1, FIGS. 5 & 6). Additionally, the variants exhibited no significant monomer loss, aggregation or fragmentation in an accelerated thermal stability assay (Table 2).

TABLE 1

| | | | | | | | | | |
|---|---|---|---|---|---|---|---|---|---|
| DuetMab variants expression and pairing properties | | | | | | | | | |
| Sample ID | Culture volume | Day 10/12 titer* (mg/L) | % correct paired LC | % monomer MabSelect Sure | κ/λ Chromatography | Final % monomer | Final % correct paired LC | Endotoxin level | Final Yield |
| VLWT + VH WT | 500 ml | 72.2 | 92 | 82 | Kappa | 100 | 99 | <0.1 EU/mg | 4 mg |
| VL GL + VH WT | 500 ml | 60.8 | 98 | 82 | Na | 100 | 98 | <0.3 EU/mg | 5 mg |
| VL WT + VH GL | 500 ml | 60.5 | 97 | 86.5 | na | 100 | 97 | <0.5 EU/mg | 5 mg |
| VL GL + VH GL | 500 ml | 66.7 | 96 | 84 | na | 100 | 96 | <0.1 EU/mg | 7 mg |
| VL GL (CDRL1 M-I) + VH GL | 500 ml | 65.2 | 96 | 83 | na | 100 | 96 | <0.5 EU/mg | 8 mg |

All variants were subjected to an accelerated thermal stability assay at 45° C. for 2 weeks in 1 mg/mL PBS buffer. Monomer loss, aggregation and fragmentation were measured both before and after high temperature storage using standard techniques, with the results provided in Table 2.

TABLE 2

Monomer loss, aggregation or fragmentation in an accelerated thermal stability assay for PD1/TIGIT DuetMab variants

| Clone name | Monomer retention (mins) | Starting purity post-protein A | | | Post 45° C., 2 wks, 1 mg/ml PBS | | | Change | | |
|---|---|---|---|---|---|---|---|---|---|---|
| | | % Monomer | % Aggregate | % Fragment | % Monomer | % Aggregate | % Fragment | % Monomer loss | % increase in aggregate | % increase in fragment |
| P-VAR1 w.t. DuetMab | 9.2 | 100.0 | 0.0 | 0.0 | 97.6 | 0.0 | 2.4 | 2.4 | 0.0 | 2.4 |
| VAR1 VL GL (CDRL1 M-I) + VH GL DuetMab | 9.2 | 100.0 | 0.0 | 0.0 | 97.8 | 0.0 | 2.2 | 2.2 | 0.0 | 2.2 |
| VL GL + VH GL DuetMab | 9.2 | 100.0 | 0.0 | 0.0 | 98.0 | 0.2 | 1.8 | 2.0 | 0.2 | 1.8 |

Intrinsic kinetics of the PD1-TIGIT duetMab LO115/P-VAR1(VHWT-VLWT) and VAR1 (LO115/VHGL-VLGL (M-I)) were assessed via BiaCore according to the manufacturer's instructions. Binding experiments were carried out using a BIAcore T200 instrument (BIAcore). The binding results are shown in Table 3.

TABLE 3

Intrinsic kinetics of PD-1/TIGIT DuetMabs by BiaCore

| Ligand | Sample | ka (l/Ms) | kd (l/s) | KD (M) | Chi$^2$ (RU$^2$) |
|---|---|---|---|---|---|
| huTIGIT | P-VAR1 | 4.67E+06 | 4.64E−05 | 9.9E−12 | 0.0119 |
| huTIGIT | VAR1 | 4.37E+06 | 6.57E−05 | 15.0E−12 | 0.0150 |
| cyTIGIT | P-VAR1 | 1.03E+06 | 3.29E−02 | 32.1E−9 | 0.7350 |
| cyTIGIT | VAR1 | 9.99E+05 | 4.11E−02 | 41.1E−9 | 1.3400 |

TABLE 3-continued

Intrinsic kinetics of PD-1/TIGIT DuetMabs by BiaCore

| Ligand | Sample | ka (l/Ms) | kd (l/s) | KD (M) | Chi$^2$ (RU$^2$) |
|---|---|---|---|---|---|
| muTIGIT | P-VAR1 | 1.66E+06 | 3.78E−03 | 2.3E−9 | 0.1350 |
| muTIGIT | VAR1 | 2.17E+06 | 6.31E−03 | 2.9E−9 | 0.0285 |

Example 2: PD-1/TIGIT Bispecific Binding Proteins and Characterization of Binding Proteins A bispecific binding protein in DuetMab format that binds PD-1 and TIGIT was created using the sequences in Table 4 below. CDRs in Table 4 are highlighted based on Kabat definition system.

TABLE 4

Sequences of AZD2936

| PD1 LO115 HCDR1 | SEQ ID NO: 1 | DYGMH |
|---|---|---|
| PD1 LO115 HCDR2 | SEQ ID NO: 2 | YISSGSYTIYSADSVKG |
| PD1 LO115 HCDR3 | SEQ ID NO: 3 | RAPNSFYEYYFDY |
| PD1 LO115 LCDR1 | SEQ ID NO: 4 | SASSKHTNLYWSRHMY |
| PD1 LO115 LCDR2 | SEQ ID NO: 5 | LTSNRAT |
| PD1 LO115 LCDR3 | SEQ ID NO: 6 | QQWSSNPFT |
| PD1 LO115 variable heavy chain | SEQ ID NO: 7 | EVQLVESGGGLVQPGGSLRLSCAASGFTFSDYGMHWVR QAPGKGLEWVAYISSGSYTIYSADSVKGRFTISRDNAKN SLYLQMNSLRAEDTAVYYCARRAPNSFYEYYFDYWGQ GTTVTVSS |

TABLE 4-continued

Sequences of AZD2936

| | | |
|---|---|---|
| PD1 LO115<br>Hole heavy<br>chain | SEQ ID<br>NO: 8 | EVQLVESGGGLVQPGGSLRLSCAASGFTFSDYGMHWVR<br>QAPGKGLEWVAYISSGSYTIYSADSVKGRFTISRDNAKN<br>SLYLQMNSLRAEDTAVYYCARRAPNSFYEYYFDYWGQ<br>GTTVTVSSASTKGPSVFPLAPSSKSTSGGTAALGCLVKD<br>YFPEPVTVSWNSGALTSGVHTFPAVLQSSGLYSLSSVVT<br>VPSSSLGTQTYICNVNHKPSNTKVDKRVEPKSCDKTHTC<br>PPCPAPEFEGGPSVFLFPPKPKDTLMISRTPEVTCVVVDV<br>SHEDPEVKFNWYVDGVEVHNAKTKPREEQYNSTYRVV<br>SVLTVLHQDWLNGKEYKCKVSNKALPASIEKTISKAKG<br>QPREPQVCTLPPSREEMTKNQVSLSCAVKGFYPSDIAVE<br>WESNGQPENNYKTTPPVLDSDGSFFLVSKLTVDKSRWQ<br>QGNVFSCSVMHEALHNHYTQKSLSLSPGK |
| PD1 LO115<br>variable light<br>chain | SEQ ID<br>NO: 9 | QIVLTQSPATLSLSPGERATLSCSASSKHTNLYWSRHMY<br>WYQQKPGQAPRLLIYLTSNRATGIPARFSGSGSGTDFTLT<br>ISSLEPEDFAVYYCQQWSSNPFTFGQGTKLEIK |
| PD1 LO115<br>WT Kappa<br>light chain | SEQ ID<br>NO: 10 | QIVLTQSPATLSLSPGERATLSCSASSKHTNLYWSRHMY<br>WYQQKPGQAPRLLIYLTSNRATGIPARFSGSGSGTDFTLT<br>ISSLEPEDFAVYYCQQWSSNPFTFGQGTKLEIKRTVAAPS<br>VFIFPPSDEQLKSGTASVVCLLNNFYPREAKVQWKVDN<br>ALQSGNSQESVTEQDSKDSTYSLSSTLTLSKADYEKHKV<br>YACEVTHQGLSSPVTKSFNRGEC |
| TIGIT VAR1<br>HCDR1 | SEQ ID<br>NO: 11 | SYAMH |
| TIGIT VAR1<br>HCDR2 | SEQ ID<br>NO: 12 | VISYAGEVKYYADSVKG |
| TIGIT VAR1<br>HCDR3 | SEQ ID<br>NO: 13 | DPLPLHYYGMDV |
| TIGIT VAR1<br>LCDR1 | SEQ ID<br>NO: 14 | SGSSSNIGRRPVN |
| TIGIT VAR1<br>LCDR2 | SEQ ID<br>NO: 15 | SQNQRPS |
| TIGIT VAR1<br>LCDR3 | SEQ ID<br>NO: 16 | AVWDDIGRVLQ |
| TIGIT VAR1<br>variable<br>heavy chain | SEQ ID<br>NO: 17 | QVQLVESGGGVVQPGRSLRLSCAASGFTFSSYAMHWVR<br>QAPGKGLEWVAVISYAGEVKYYADSVKGRFTISRDNSK<br>NTLYLQMNSLRAEDTAVYYCARDPLPLHYYGMDVWG<br>QGTTVTVSS |
| TIGIT VAR1<br>Knob heavy<br>chain | SEQ ID<br>NO: 18 | QVQLVESGGGVVQPGRSLRLSCAASGFTFSSYAMHWVR<br>QAPGKGLEWVAVISYAGEVKYYADSVKGRFTISRDNSK<br>NTLYLQMNSLRAEDTAVYYCARDPLPLHYYGMDVWG<br>QGTTVTVSSASTKGPSVCPLAPSSKSTSGGTAALGCLVK<br>DYFPEPVTVSWNSGALTSGVHTFPAVLQSSGLYSLSSVV<br>TVPSSSLGTQTYICNVNHKPSNTKVDKRVEPKSVDKTHT<br>CPPCPAPEFEGGPSVFLFPPKPKDTLMISRTPEVTCVVVD<br>VSHEDPEVKFNWYVDGVEVHNAKTKPREEQYNSTYRV<br>VSVLTVLHQDWLNGKEYKCKVSNKALPASIEKTISKAK<br>GQPREPQVYTLPPCREEMTKNQVSLWCLVKGFYPSDIA<br>VEWESNGQPENNYKTTPPVLDSDGSFFLYSKLTVDKSR<br>WQQGNVFSCSVMHEALHNHYTQKSLSLSPGK |
| TIGIT VAR1<br>variable light<br>chain | SEQ ID<br>NO: 19 | QSVLTQPPSASGTPGQRVTISCSGSSSNIGRRPVNWYQQL<br>PGTAPKLLIYSQNQRPSGVPDRFSGSQSGTSASLAISGLQ<br>SEDEADYFCAVWDDIGRVLQLGGGTQLTVL |
| TIGIT VAR1<br>engineered<br>Lambda light<br>chain | SEQ ID<br>NO: 20 | QSVLTQPPSASGTPGQRVTISCSGSSSNIGRRPVNWYQQL<br>PGTAPKLLIYSQNQRPSGVPDRFSGSQSGTSASLAISGLQ<br>SEDEADYFCAVWDDIGRVLQLGGGTQLTVLGQPKAAPS<br>VTLFPPCSEELQANKATLVCLISDFYPGAVTVAWKADSS<br>PVKAGVETTTPSKQSNNKYAASSYLSLTPEQWKSHRSYS<br>CQVTHEGSTVEKTVAPTEVS |
| PD1 LO115<br>variable<br>heavy chain | SEQ ID<br>NO: 21 | GAGGTGCAGCTGGTGGAATCCGGCGGAGGACTGGTGC<br>AGCCTGGCGGCTCCCTGAGACTGTCTTGCGCCGCCTCC<br>GGCTTCACATTCTCCGACTACGGCATGCACTGGGTCC<br>GACAGGCCCCTGGAAAGGGCCTGGAATGGGTGGCCTA<br>CATCTCCTCCGGCTCCTACACCATCTACTCCGCCGACT<br>CCGTGAAGGGCCGGTTCACCATCTCCCGGGACAACGC |

TABLE 4-continued

| Sequences of AZD2936 |
|---|

|  |  | CAAGAACTCCCTGTACCTGCAGATGAACTCCCTGCGG<br>GCCGAGGACACAGCCGTGTACTACTGTGCCAGACGGG<br>CCCCTAACTCCTTCTACGAGTACTACTTCGACTACTGG<br>GGCCAGGGCACCACCGTGACCGTGTCCTCT |
|---|---|---|
| PD1 LO115<br>Hole heavy<br>chain | SEQ ID<br>NO: 22 | GAGGTGCAGCTGGTGGAATCCGGCGGAGGACTGGTGC<br>AGCCTGGCGGCTCCCTGAGACTGTCTTGCGCCGCCTCC<br>GGCTTCACATTCTCCGACTACGGCATGCACTGGGTCC<br>GACAGGCCCCTGGAAAGGGCCTGGAATGGGTGGCCTA<br>CATCTCCTCCGGCTCCTACACCATCTACTCCGCCGACT<br>CCGTGAAGGGCCGGTTCACCATCTCCCGGGACAACGC<br>CAAGAACTCCCTGTACCTGCAGATGAACTCCCTGCGG<br>GCCGAGGACACAGCCGTGTACTACTGTGCCAGACGGG<br>CCCCTAACTCCTTCTACGAGTACTACTTCGACTACTGG<br>GGCCAGGGCACCACCGTGACCGTGTCCTCTGCTAGCA<br>CCAAAGGTCCGAGCGTTTTTCCGCTGGCACCGAGCAG<br>CAAAAGCACCTCTGGTGGCACCGCAGCACTGGGTTGT<br>CTGGTGAAAGATTATTTTCCGGAACCGGTTACCGTTTC<br>TTGGAATAGCGGTGCACTGACCAGCGGTGTTCATACC<br>TTTCCGGCAGTTCTGCAGAGCAGCGGTCTGTATAGCCT<br>GTCTAGCGTTGTTACCGTTCCGAGCAGCAGCCTGGGC<br>ACCCAGACCTATATTTGCAATGTGAATCATAAACCGA<br>GCAATACAAAAGTTGATAAACGCGTTGAACCGAAAA<br>GCTGTGACAAAACTCACACGTGCCCACCGTGCCCAGC<br>ACCTGAGTTCGAGGGGGGACCGTCAGTCTTCCTCTTCC<br>CCCCAAAACCCAAGGACACCCTCATGATCTCCCGGAC<br>CCCTGAGGTCACATGCGTGGTGGTGGACGTGAGCCAC<br>GAAGACCCTGAGGTCAAGTTCAACTGGTACGTGGACG<br>GCGTGGAGGTGCATAATGCCAAGACAAAGCCGCGGG<br>AGGAGCAGTACAACAGCACGTACCGTGTGGTCAGCGT<br>CCTCACCGTCCTGCACCAGGACTGGCTGAATGGCAAG<br>GAGTACAAGTGCAAGGTCTCCAACAAAGCCCTCCCAG<br>CCAGCATCGAGAAAACCATCTCCAAAGCCAAAGGGC<br>AGCCCCGAGAACCACAGGTCTGCACCCTGCCCCCATC<br>CCGGGAGGAGATGACCAAGAACCAGGTCAGCCTGAG<br>CTGCGCGGTCAAAGGCTTCTATCCCAGCGACATCGCC<br>GTGGAGTGGGAGAGCAATGGGCAGCCGGAGAACAAC<br>TACAAGACCACGCCTCCCGTGCTGGACTCCGACGGCT<br>CCTTCTTCCTCGTTAGCAAGCTCACCGTGGACAAGAG<br>CAGGTGGCAGCAGGGGAACGTCTTCTCATGCTCCGTG<br>ATGCATGAGGCTCTGCACAACCACTACACGCAGAAGA<br>GCCTCTCCCTGTCTCCGGGTAAATGA |
| PD1 LO115<br>variable light<br>chain | SEQ ID<br>NO: 23 | CAGATCGTGCTGACCCAGTCCCCTGCCACCCTGTCCCT<br>GAGCCCTGGCGAGAGAGCCACCCTGAGCTGCTCCGCC<br>TCCTCCAAGCACACCAACCTGTACTGGTCCCGGCACA<br>TGTACTGGTATCAGCAGAAGCCCGGCCAGGCCCCTCG<br>GCTGCTGATCTACCTGACCTCTAACCGGGCCACCGGC<br>ATCCCTGCCAGATTCTCCGGCTCTGGCTCCGGCACCGA<br>CTTCACCCTGACCATCTCCAGCCTGGAACCCGAGGAC<br>TTCGCCGTGTACTACTGCCAGCAGTGGTCCTCCAACCC<br>CTTCACCTTCGGCCAGGGCACCAAGCTGGAAATCAAG |
| PD1 LO115<br>WT Kappa<br>light chain | SEQ ID<br>NO: 24 | CAGATCGTGCTGACCCAGTCCCCTGCCACCCTGTCCCT<br>GAGCCCTGGCGAGAGAGCCACCCTGAGCTGCTCCGCC<br>TCCTCCAAGCACACCAACCTGTACTGGTCCCGGCACA<br>TGTACTGGTATCAGCAGAAGCCCGGCCAGGCCCCTCG<br>GCTGCTGATCTACCTGACCTCTAACCGGGCCACCGGC<br>ATCCCTGCCAGATTCTCCGGCTCTGGCTCCGGCACCGA<br>CTTCACCCTGACCATCTCCAGCCTGGAACCCGAGGAC<br>TTCGCCGTGTACTACTGCCAGCAGTGGTCCTCCAACCC<br>CTTCACCTTCGGCCAGGGCACCAAGCTGGAAATCAAG<br>CGTACGGTGGCTGCACCATCTGTCTTCATCTTCCCGCC<br>ATCTGATGAGCAGTTGAAATCTGGAACTGCCTCTGTT<br>GTGTGCCTGCTGAATAACTTCTATCCCAGAGAGGCCA<br>AAGTACAGTGGAAGGTGGATAACGCCCTCCAATCGGG<br>TAACTCCCAGGAGAGTGTCACAGAGCAGGACAGCAA<br>GGACAGCACCTACAGCCTCAGCAGCACCCTGACGCTG<br>AGCAAAGCAGACTACGAGAAACACAAAGTCTACGCC<br>TGCGAAGTCACCCATCAGGGCCTGAGCTCGCCCGTCA<br>CAAAGAGCTTCAACAGGGGAGAGTGTTAG |
| TIGIT VAR1<br>variable<br>heavy chain | SEQ ID<br>NO: 25 | CAGGTGCAGCTGGTGGAGTCTGGAGGAGGCGTGGTCC<br>AGCCTGGGAGGTCCCTGAGACTCTCCTGTGCAGCCTC<br>TGGATTCACCTTCAGTAGCTATGCTATGCACTGGGTCC<br>GCCAGGCTCCAGGCAAGGGGCTGGAGTGGGTGGCAG<br>TTATATCATATGCGGGGGAGGTGAAATACTACGCAGA<br>CTCCGTGAAGGGCCGATTCACCATCTCCAGAGACAAT |

TABLE 4-continued

| Sequences of AZD2936 | | |
|---|---|---|
| | | TCCAAGAACACGCTGTATCTGCAAATGAACAGCCTGA<br>GAGCTGAGGACACGGCTGTGTATTACTGTGCGAGAGA<br>CCCGCTACCGCTACATTACTACGGTATGGACGTCTGG<br>GGCCAAGGGACCACGGTCACCGTCTCCTCA |
| TIGIT VAR1<br>Knob heavy<br>chain | SEQ ID<br>NO: 26 | CAGGTGCAGCTGGTGGAGTCTGGAGGAGGCGTGGTCC<br>AGCCTGGGAGGTCCCTGAGACTCTCCTGTGCAGCCTC<br>TGGATTCACCTTCAGTAGCTATGCTATGCACTGGGTCC<br>GCCAGGCTCCAGGCAAGGGGCTGGAGTGGGTGGCAG<br>TTATATCATATGCGGGGGAGGTGAAATACTACGCAGA<br>CTCCGTGAAGGGCCGATTCACCATCTCCAGAGACAAT<br>TCCAAGAACACGCTGTATCTGCAAATGAACAGCCTGA<br>GAGCTGAGGACACGGCTGTGTATTACTGTGCGAGAGA<br>CCCGCTACCGCTACATTACTACGGTATGGACGTCTGG<br>GGCCAAGGGACCACGGTCACCGTCTCCTCAGCGTCGA<br>CCAAAGGTCCGAGCGTGTGCCCGCTGGCACCGAGCAG<br>CAAAAGCACCTCTGGTGGCACCGCAGCACTGGGTTGT<br>CTGGTGAAAGATTATTTTCCGGAACCGGTTACCGTTTC<br>TTGGAATAGCGGTGCACTGACCAGCGGTGTTCATACC<br>TTTCCGGCAGTCCTGCAGAGCAGCGGTCTGTATAGCC<br>TGTCTAGCGTTGTTACCGTTCCGAGCAGCAGCCTGGG<br>CACCCAGACCTATATTTGCAATGTGAATCATAAACCG<br>AGCAATACCAAAGTTGATAAACGCGTTGAACCGAAAA<br>GCGTGGACAAAACTCACACGTGCCCACCGTGCCCAGC<br>ACCTGAGTTCGAGGGGGGACCGTCAGTCTTCCTCTTCC<br>CCCCAAAACCCAAGGACACCCTCATGATCTCCCGGAC<br>CCCTGAGGTCACATGCGTGGTGGTGGACGTGAGCCAC<br>GAAGACCCTGAGGTCAAGTTCAACTGGTACGTGGACG<br>GCGTGGAGGTGCATAATGCCAAGACAAAGCCGCGGG<br>AGGAGCAGTACAACAGCACGTACCGTGTGGTCAGCGT<br>CCTCACCGTCCTGCACCAGGACTGGCTGAATGGCAAG<br>GAGTACAAGTGCAAGGTCTCCAACAAAGCCCTCCCAG<br>CCAGCATCGAGAAAACCATCTCCAAAGCCAAAGGGC<br>AGCCCCGAGAACCACAGGTCTACACCCTGCCCCCATG<br>CCGGGAGGAGATGACCAAGAACCAGGTCAGCCTGTG<br>GTGCCTGGTCAAAGGCTTCTATCCCAGCGACATCGCC<br>GTGGAGTGGGAGAGCAATGGGCAGCCGGAGAACAAC<br>TACAAGACCACGCCTCCCGTGCTGGACTCCGACGGCT<br>CCTTCTTCCTCTATAGCAAGCTCACCGTGGACAAGAG<br>CAGGTGGCAGCAGGGGAACGTCTTCTCATGCTCCGTG<br>ATGCATGAGGCTCTGCACAACCACTACACGCAGAAGA<br>GCTTAAGCCTGTCTCCGGGTAAATGA |
| TIGIT VAR1<br>variable light<br>chain | SEQ ID<br>NO: 27 | CAGTCTGTGCTGACTCAGCCTCCCTCAGCGTCTGGGAC<br>CCCCGGGCAGAGGGTCACCATCTCTTGTTCTGGAAGC<br>AGCTCCAATATCGGAAGGAGGCCTGTAAACTGGTACC<br>AGCAGCTCCCAGGAACGGCCCCCAAACTCCTCATCTA<br>TAGTCAGAATCAGCGGCCCTCAGGGGTCCCTGACCGA<br>TTCTCTGGCTCCCAGTCTGGCACCTCAGCCTCCCTGGC<br>CATCAGTGGGCTCCAGTCTGAGGATGAGGCTGATTAT<br>TTCTGTGCAGTTTGGGATGACATCGGCCGCGTCCTGCA<br>GTTAGGCGGAGGCACCCAGCTGACCGTCCTA |
| TIGIT VAR1<br>engineered<br>Lambda light<br>chain | SEQ ID<br>NO: 28 | CAGTCTGTGCTGACTCAGCCTCCCTCAGCGTCTGGGAC<br>CCCCGGGCAGAGGGTCACCATCTCTTGTTCTGGAAGC<br>AGCTCCAATATCGGAAGGAGGCCTGTAAACTGGTACC<br>AGCAGCTCCCAGGAACGGCCCCCAAACTCCTCATCTA<br>TAGTCAGAATCAGCGGCCCTCAGGGGTCCCTGACCGA<br>TTCTCTGGCTCCCAGTCTGGCACCTCAGCCTCCCTGGC<br>CATCAGTGGGCTCCAGTCTGAGGATGAGGCTGATTAT<br>TTCTGTGCAGTTTGGGATGACATCGGCCGCGTCCTGCA<br>GTTAGGCGGAGGCACCCAGCTGACCGTCCTAGGTCAG<br>CCCAAGGCGGCCCCCTCGGTCACTCTGTTCCCGCCCTG<br>CTCTGAGGAGCTTCAAGCCAACAAGGCCACACTGGTG<br>TGTCTCATAAGTGACTTCTACCCGGGAGCCGTGACAG<br>TGGCCTGGAAGGCAGATAGCAGCCCCGTCAAGGCGG<br>GAGTGGAGACCACCACACCCTCCAAACAAAGCAACA<br>ACAAGTACGCGGCCAGCAGCTACCTGAGCCTGACGCC<br>TGAGCAGTGGAAGTCCCACAGAAGCTACAGCTGCCAG<br>GTCACGCATGAAGGGAGCACCGTGGAGAAGACAGTG<br>GCCCCTACAGAAGTGTCATGA |
| Parental<br>VAR1 VH | SEQ ID<br>NO: 35 | EVQLVETGGGLIQPGRSLRLSCAASGFTFSSYAMHWVR<br>QAPGKGLEWVAVISYAGEVKYY<br>ADSVKGRFTISRDNSKNTLYLQMNSLRAEDTAVYYCAR<br>DPLPLHYYGMDVWGQGTTVTVSS |

TABLE 4-continued

Sequences of AZD2936

```
Parental      SEQ ID   QSALTQPRSASGNPGQRVTISCSGSSSNMGRRPVNWYQ
VAR1 VL       NO: 36   QIPGTAPKLLIYSQNQRPSGVPDRFSGSQSGTSASLTISGL
                       QSEDEAEYFCAVWDDIGRVLQLGGGTQLAVL Germline      SEQ ID   QVQLVETGGGLIQPGRSLRLSCAASGFTFSSYAMHWVR
Parental      NO: 37   QAPGKGLEWVAVISYAGEVKYY
VAR1 VH                ADSVKGRFTISRDNSKNTLYLQMNSLRAEDTAVYYCAR
                       DPLPLHYYGMDVWGQGTTVTVSS Parental      SEQ ID   GAGGTGCAGCTGGTGGAGACTGGAGGAGGCTTGATCC
VAR1 VH       NO: 38   AGCCTGGGAGGTCCCTGAGACTCTCCTGTGCAGCCTC
nucleic acid           TGGATTCACCTTCAGTAGCTATGCTATGCACTGGGTCC
                       GCCAGGCTCCAGGCAAGGGGCTGGAGTGGGTGGCAG
                       TTATATCATATGCGGGGGAGGTGAAATACTACGCAGA
                       CTCCGTGAAGGGCCGATTCACCATCTCCAGAGACAAT
                       TCCAAGAACACGCTGTATCTGCAAATGAACAGCCTGA
                       GAGCTGAGGACACGGCTGTGTATTACTGTGCGAGAGA
                       CCCGCTACCGCTACATTACTACGGTATGGACGTCTGG
                       GGCCAAGGGACCACGGTCACCGTCTCCTCA Parental      SEQ ID   CAGTCTGCCCTGACTCAGCCTCGCTCAGCGTCTGGGA
VAR1 VL       NO: 39   ACCCCGGGCAGAGGGTCACCATCTCTTGTTCTGGAAG
nucleic acid           CAGCTCCAATATGGGAAGGAGGCCTGTAAACTGGTAC
                       CAGCAGATCCCAGGAACGGCCCCCAAACTCCTCATCT
                       ATAGTCAGAATCAGCGGCCCTCAGGGGTCCCTGACCG
                       ATTCTCTGGCTCCCAGTCTGGCACCTCAGCCTCCCTGA
                       CCATCAGTGGGCTCCAGTCTGAGGATGAGGCTGAATA
                       TTTCTGTGCAGTTTGGGATGACATCGGCCGCGTCCTGC
                       AGTTAGGCGGAGGCACCCAGCTGGCCGTCCTA Germline      SEQ ID   CAGGTGCAGCTGGTGGAGACTGGAGGAGGCTTGATCC
Parental      NO: 40   AGCCTGGGAGGTCCCTGAGACTCTCCTGTGCAGCCTC
VAR1 VH                TGGATTCACCTTCAGTAGCTATGCTATGCACTGGGTCC
nucleic acid           GCCAGGCTCCAGGCAAGGGGCTGGAGTGGGTGGCAG
                       TTATATCATATGCGGGGGAGGTGAAATACTACGCAGA
                       CTCCGTGAAGGGCCGATTCACCATCTCCAGAGACAAT
                       TCCAAGAACACGCTGTATCTGCAAATGAACAGCCTGA
                       GAGCTGAGGACACGGCTGTGTATTACTGTGCGAGAGA
                       CCCGCTACCGCTACATTACTACGGTATGGACGTCTGG
                       GGCCAAGGGACCACGGTCACCGTCTCCTCA
```

Concurrent Binding Study

Figure 8A:
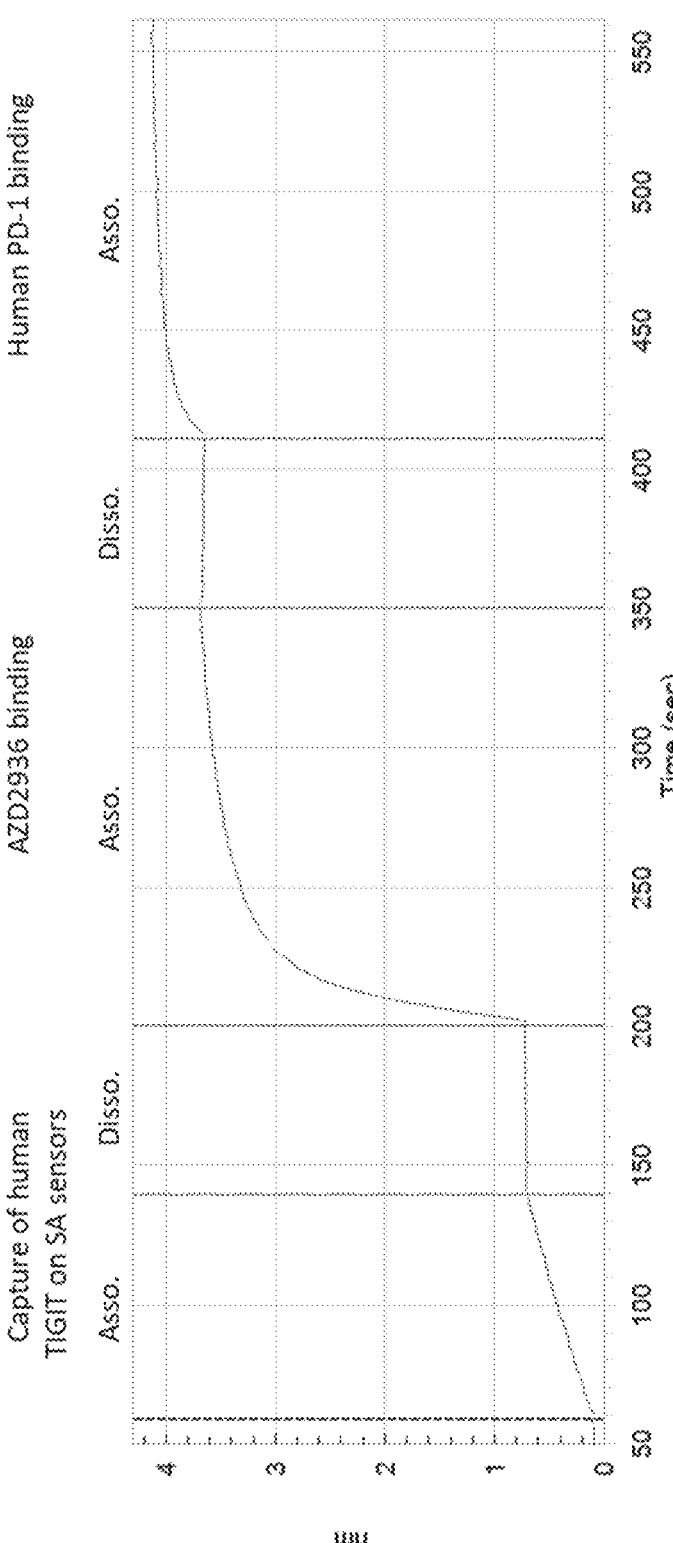
FIGS. 8A-8B.
Figure 8B:
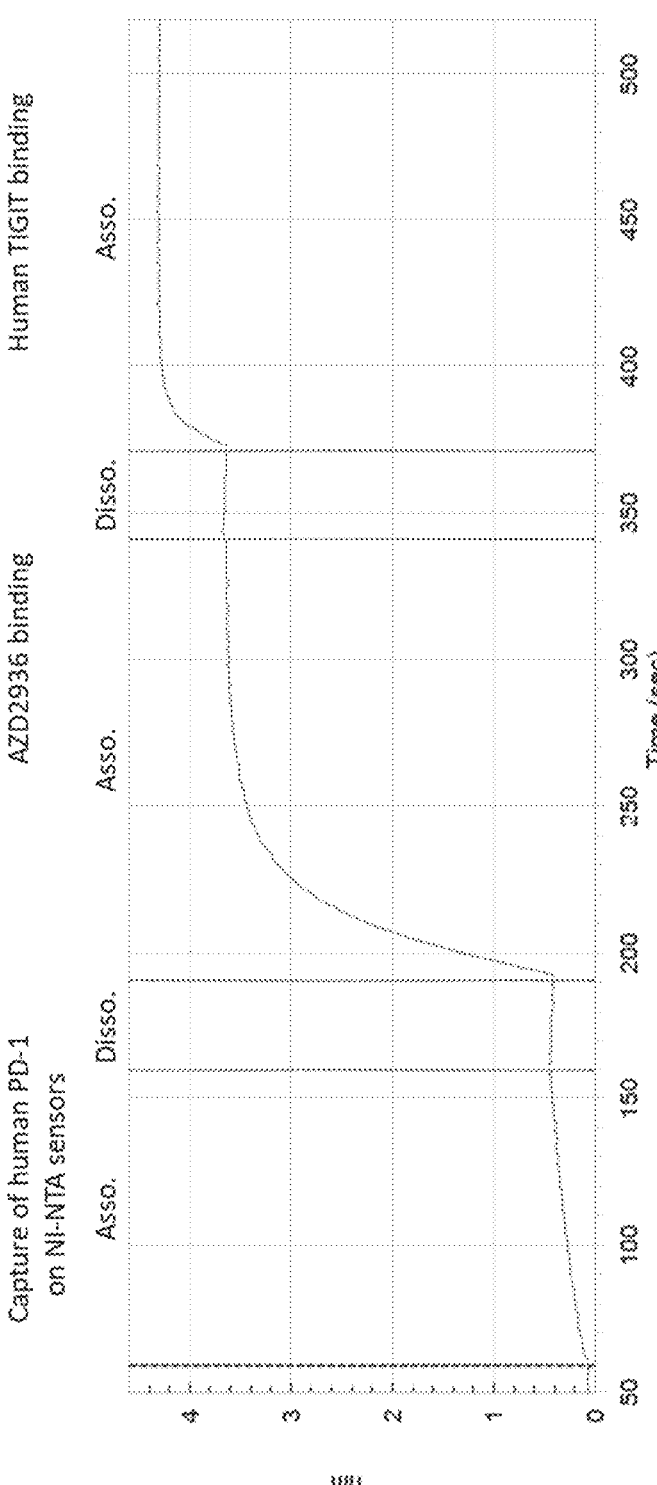

Concurrent binding studies to recombinant human PD-1 and TIGIT proteins were measured by biolayer interferometry on an Octet384 instrument (ForteBio, Fremont, CA). Biotinylated human TIGIT protein at 0.5 µg/mL in assay buffer [PBS pH 7.2, 3 mg/mL bovine serum albumin (BSA), 0.05% (v/v) Tween 20] was captured on streptavidin (SA) biosensors (ForteBio, Fremont, CA) as shown in FIG. 8A. Human PD-1 protein at 5 pg/mL in assay buffer was captured on nickel nitrilotriacetic acid (Ni-NTA) biosensors (ForteBio, Fremont, CA) as show in FIG. 8B. Following a washing step to remove any unbound protein, the respective loaded biosensors were subjected to successive association and dissociation interactions, first with 133 nM of AZD2936 and then with human PD-1 or human TIGIT antigens at 300 nM. Association and dissociation curves were calculated from a non-linear fit of the data using the Octet384 software v.9.0. The ability of AZD2936 to concurrently bind recombinant human PD-1 and TIGIT proteins was determined by Octet analysis. As shown in FIGS. 8A and 8B, AZD2936 demonstrated simultaneous binding to human TIGIT and human PD-1 antigen.

Example 3: Cellular Binding Assays

Figure 9A:
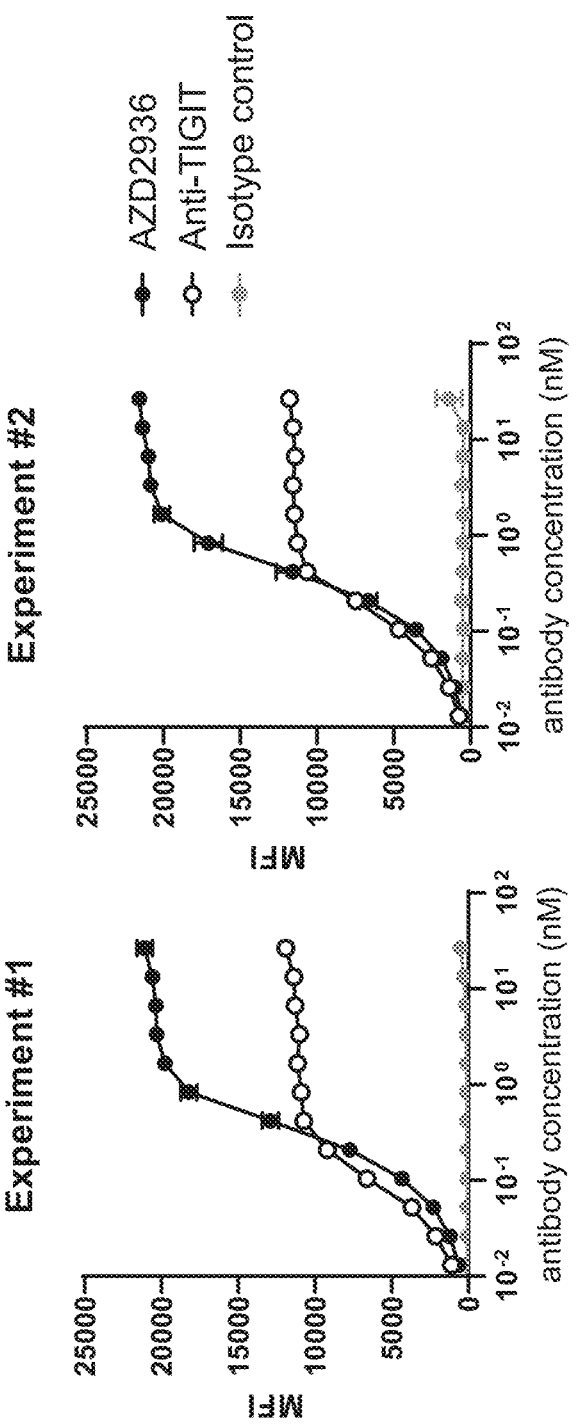
FIGS. 9A-9C show that AZD2936 demonstrated PD-1 and TIGIT binding activity as compared to monospecific antibodies.
Figure 9B:
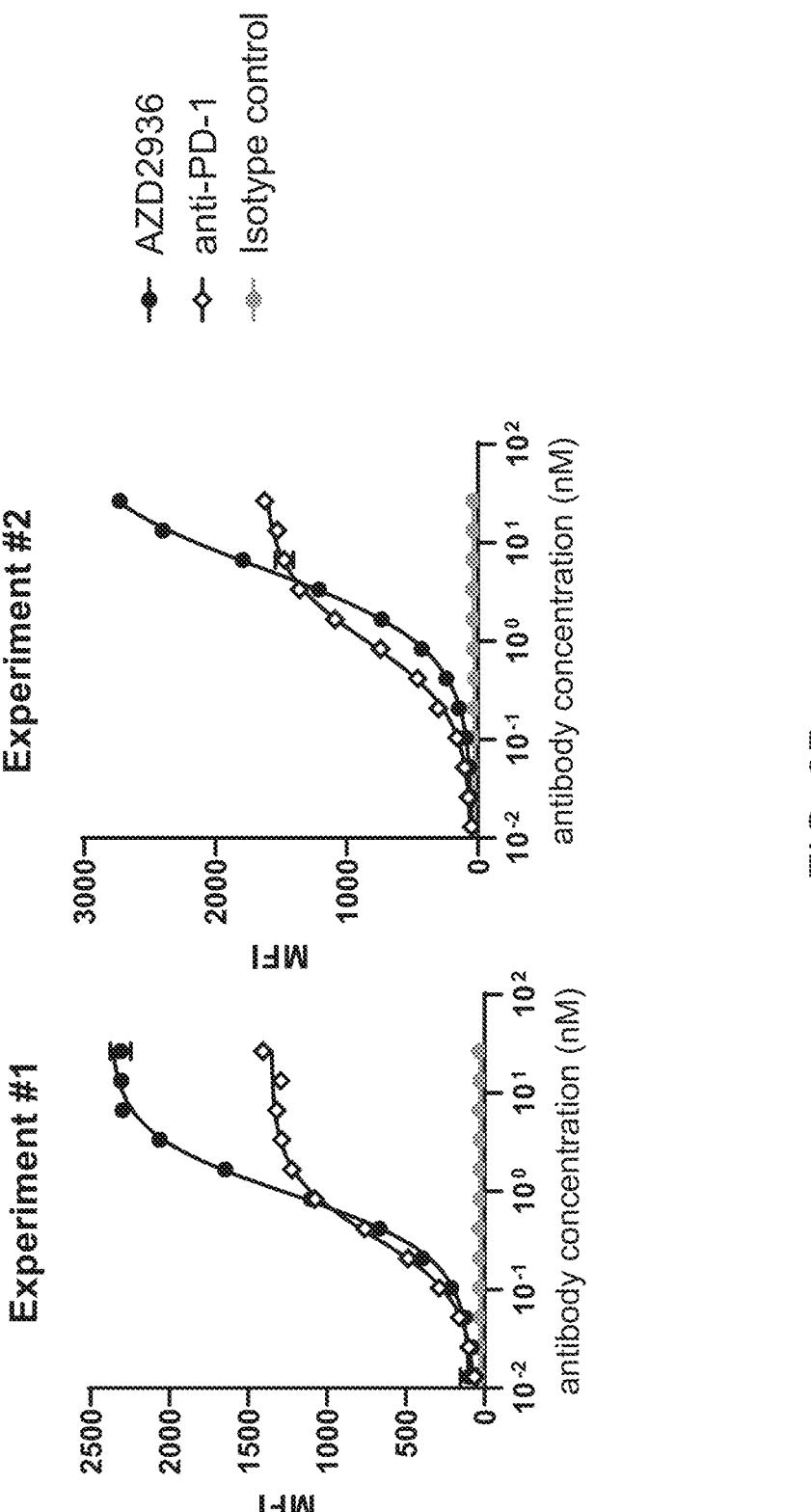
Figure 9C:
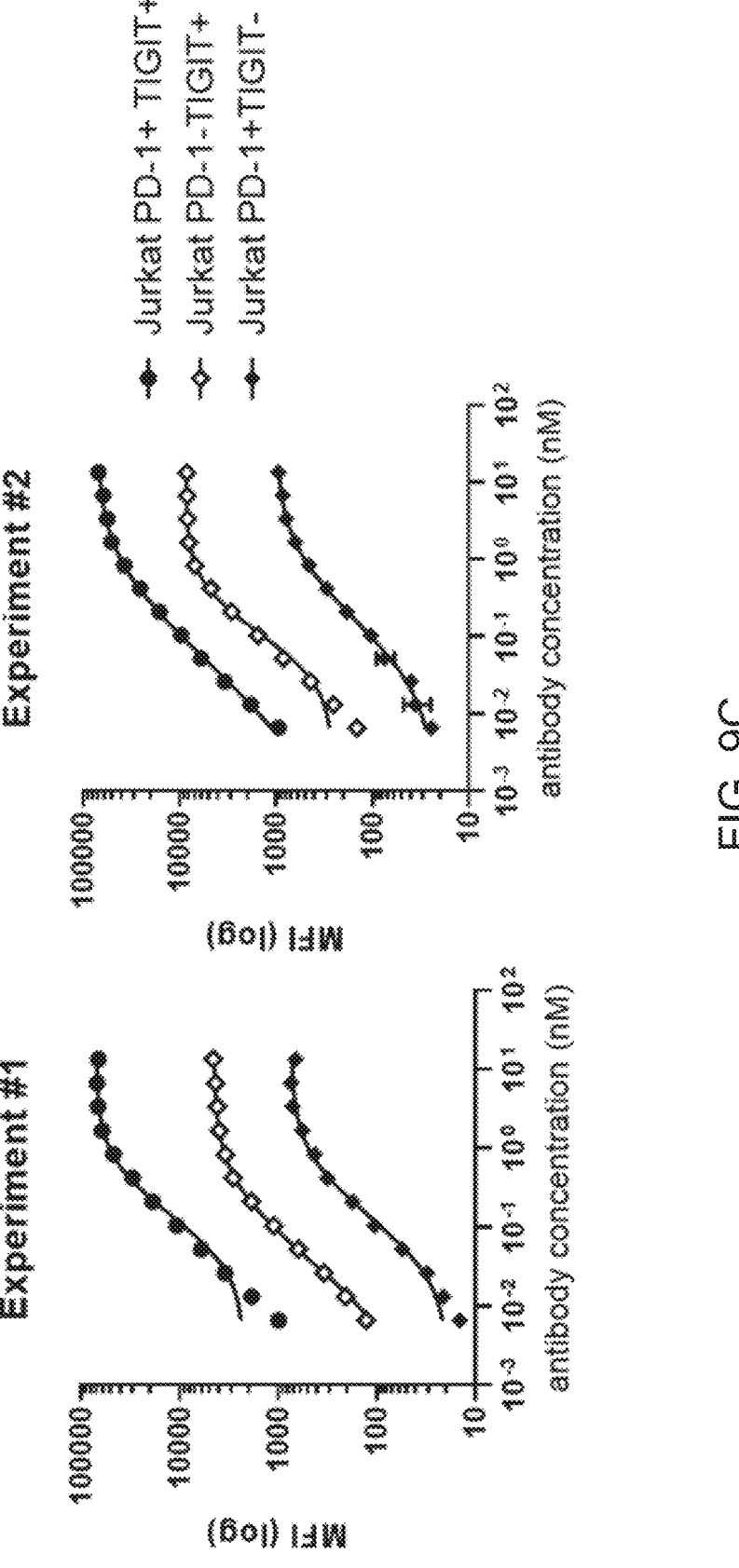

AZD2936 binding was tested against PD1 and TIGIT expressed on cell surface against monospecific anti-PD1 (LO115), monospecific anti-TIGIT (VAR1), and an isotype control as shown in FIGS. 9A-9C. Specifically, cellular based equilibrium binding assays were performed to measure the apparent affinity of AZD2936 binding to human PD-1 and TIGIT receptors expressed on the cell surface of engineered cell lines. For this purpose, Jurkat cell lines were engineered to express human PD-1 and/or TIGIT receptors. To determine if these cellular subsets were relevant for evaluation of AZD2936 binding, cell surface receptor densities of human PD-1 and TIGIT were quantified. As shown in Table 5, PD-1 receptor density on the single-positive Jurkat PD-1+TIGIT⁻ cells was determined at 11700 (SD±6690) receptors/cell and TIGIT receptor density on the single-positive Jurkat PD-1−TIGIT+ cells was determined at 147000 (SD±91500) receptors/cell. PD-1 and TIGIT receptor densities on the double-positive Jurkat PD 1+TIGIT+ cells were 621000 (SD±210000) and 149000 (SD±89100), exhibiting an 4.17:1 excess of PD-1 receptor over TIGIT receptor.

TABLE 5

| PD-1 and TIGIT Receptor Density on Engineered Jurkat Cell lines, n = 4 | | | |
|---|---|---|---|
| Cell Line | PD-1 (receptors/cell, mean ± SD) | TIGIT (receptors/cell, mean ± SD) | PD-1/TIGIT (ratio) |
| Jurkat PD-1$^+$TIGIT$^-$ | 11700 (±6690) | ND | ND |
| Jurkat PD-1$^-$TIGIT$^+$ | ND | 147000 (±91500) | ND |
| Jurkat PD-1$^+$TIGIT$^+$ | 621000 (±210000) | 149000 (±89100) | 4.17 |

ND = not determined; PD-1 = programmed cell-death protein 1; TIGIT = T cell immunoreceptor with Ig and immunoreceptor tyrosine-based inhibitory motif domains. SD = Standard Deviation.

Binding of AZD2936 was evaluated alongside bivalent mAbs, and detected on 3 Jurkat cell lines engineered to express human PD-1 and/or human TIGIT receptors. AZD2936 bound to Jurkat PD-1$^-$ TIGIT$^+$ cells in a concentration dependent manner and maintained the cellular binding properties of the anti-TIGIT mAb to TIGIT receptors (FIG. 9A). Compared to the bivalent anti-TIGIT antibody, AZD2936 demonstrated increased (2.85-fold) binding EC$_{50}$ values (Table 6) and increased maximal binding (FIG. 9A). AZD2936 bound to Jurkat PD-1$^+$TIGIT$^-$ cells in a concentration dependent manner. Compared to the bivalent anti-PD-1 antibody for binding on the PD-1$^+$TIGIT$^-$ Jurkat cells, AZD2936 demonstrated increased (4.82-fold) binding EC$_{50}$ values (Table 7) and increased maximal binding (FIG. 9B). These results demonstrated that monovalent binding is sufficient for the engagement of TIGIT or PD-1 on the Jurkat cells.

TABLE 6

| AZD2936 and Anti-TIGIT Binding Activity on TIGIT$^+$ Jurkat Cells | | | | |
|---|---|---|---|---|
| | Experiment #1 EC$_{50}$ (nM) | Experiment #2 EC$_{50}$ (nM) | Mean EC$_{50}$ (nM) | Fold Change vs. anti-TIGIT |
| AZD2936 | 0.303 | 0.375 | 0.339 | 2.85 |
| Anti-TIGIT | 0.092 | 0.147 | 0.119 | 1.00 |

TABLE 7

| AZD2936 and anti-PD-1 Binding Activity on PD-1$^+$ Jurkat Cells | | | | |
|---|---|---|---|---|
| | Experiment #1 EC$_{50}$ (nM) | Experiment #2 EC$_{50}$ (nM) | Mean EC$_{50}$ (nM) | Fold Change vs. anti-PD-1 |
| AZD2936 | 0.944 | 5.490 | 3.217 | 4.82 |
| Anti-PD-1 | 0.349 | 0.985 | 0.667 | 1.00 |

TABLE 8

| AZD2936 Binding Activity on PD-1$^+$TIGIT$^-$, PD-1$^-$TIGIT$^+$ and PD-1$^+$TIGIT$^+$ Jurkat Cells | | | |
|---|---|---|---|
| | Experiment #1 EC$_{50}$ (nM) | Experiment #2 EC$_{50}$ (nM) | Mean EC$_{50}$ (nM) |
| PD-1$^+$TIGIT$^+$ Jurkat | 0.495 | 0.769 | 0.632 |
| PD-1$^-$TIGIT$^+$ Jurkat | 0.282 | 0.346 | 0.314 |
| PD-1$^+$TIGIT$^-$ Jurkat | 0.584 | 1.01 | 0.797 |

The cellular binding properties of AZD2936 to the Jurkat cell lines expressing either PD-1 (PD-1$^+$TIGIT$^-$) or TIGIT (PD-1$^-$ TIGIT$^+$) or both receptors (PD-1$^+$TIGIT$^+$) were determined by a flow cytometry binding assay. As shown in FIG. 9C, AZD2936 bound to all three types of Jurkat cells with similar cellular binding properties. To evaluate the difference in AZD2936 binding affinity between the three cell lines, EC$_{50}$ values were determined (Table 8). The mean EC$_{50}$ of AZD2936 to the PD-1 single expressing cell line was 0.797 nM. The mean EC$_{50}$ of AZD2936 to the TIGIT$^+$ PD-1$^+$ dual expressing cell line was 0.632 nM. Binding to the cell line engineered to express TIGIT only receptors yielded the lowest mean EC$_{50}$ value at 0.314 nM.

NFAT-Luciferase Reporter Two-cell Co-culture Assays

Figure 10A:
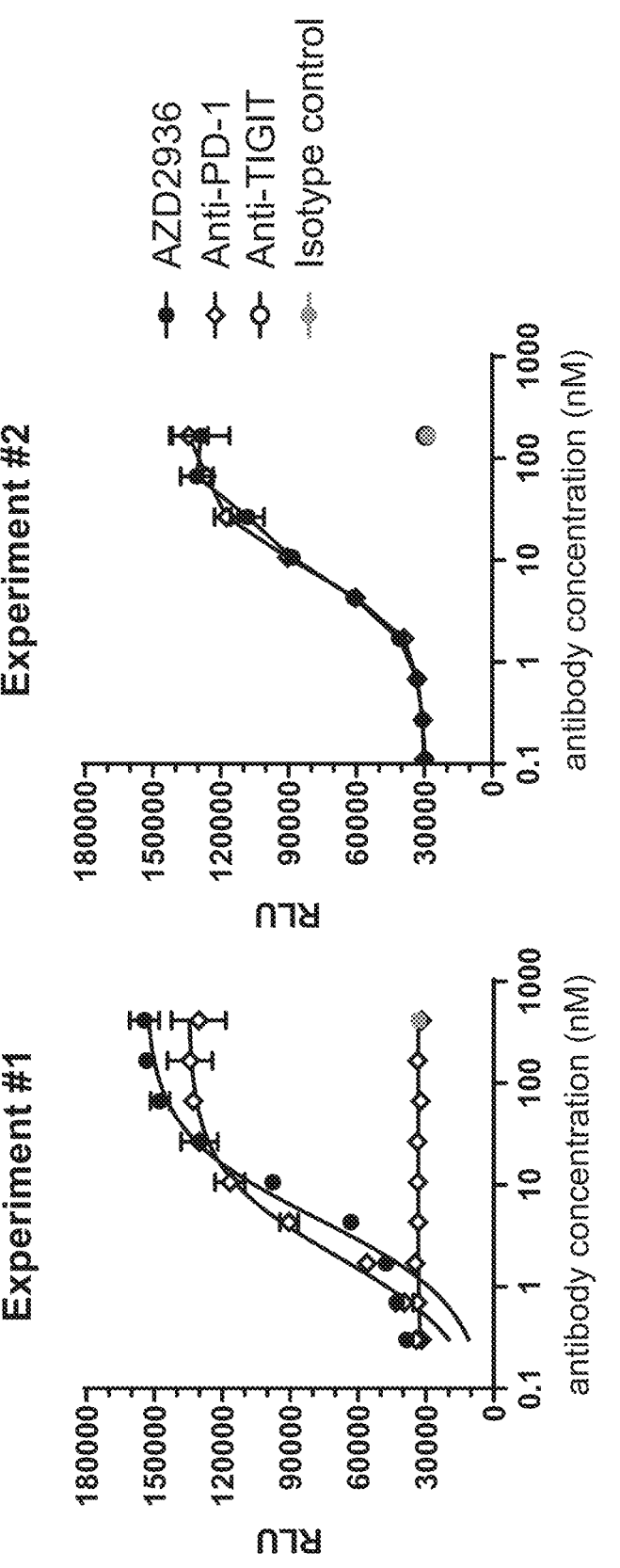
FIGS. 10A-10C shows that AZD2936 demonstrated PD-1 and TIGIT ligand blocking activity to enhance TCR mediated signaling using the Jurkat reporter assay as compared to monospecific antibodies.
Figure 10B:
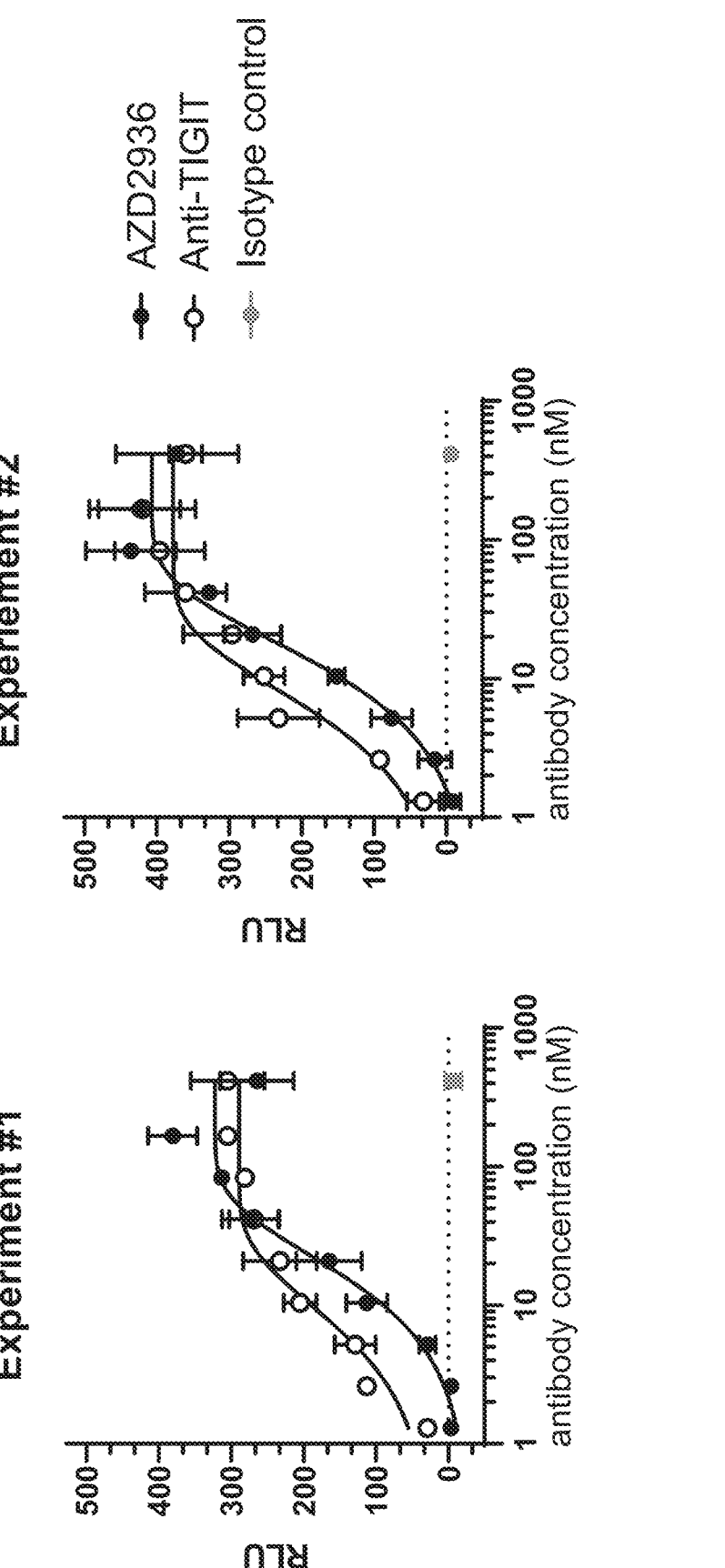
Figure 10C:
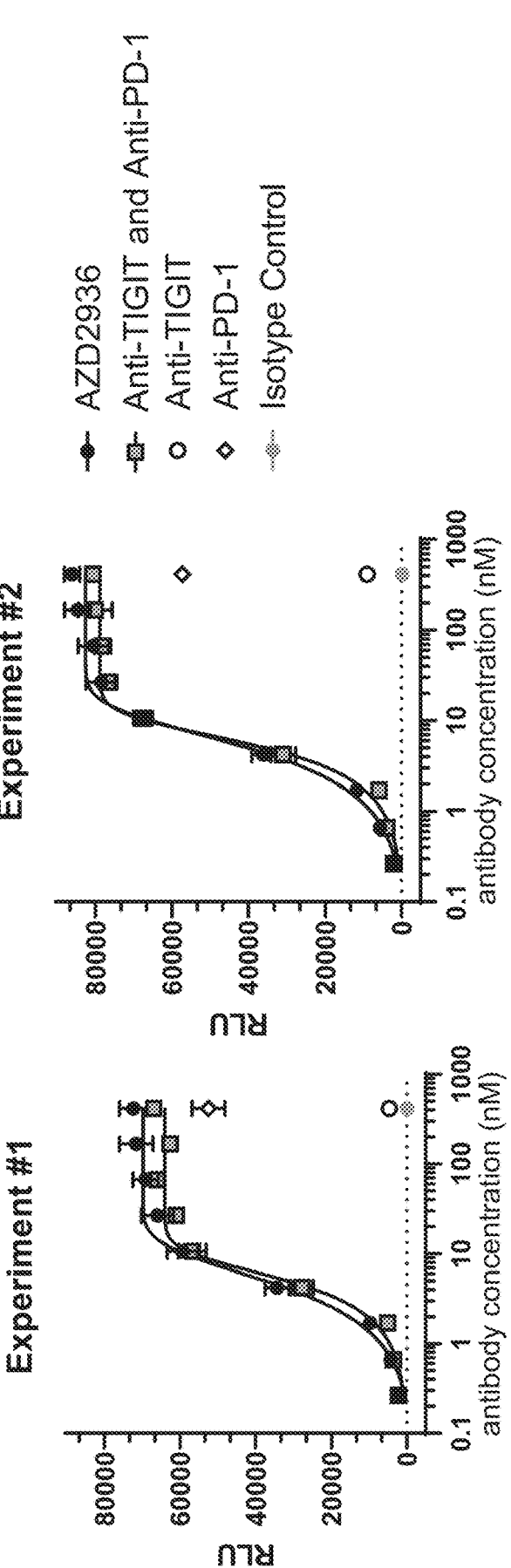

AZD2936 was tested against monospecific anti-PD1 (LO115), monospecific anti-TIGIT (VAR1), and an isotype control as shown in FIGS. 10A-10C. AZD2936 was shown to be active and have stronger ligand blocking activity for both PD-1 and TIGIT as compared to the monospecific antibodies. Specifically, to assess the ability of AZD2936 to block PD-1/PD-L1 and/or TIGIT/CD155 interactions, two-cell co-culture bioactivity assays were utilized using CHO-K1 cells genetically engineered to express the anti-CD3 scFv of OKT3, PD-L1 and CD155 and Jurkat NFAT luciferase reporter T cells genetically engineered to express human PD-1, human TIGIT or both antigens. In the assay, luciferase activity under the control of NFAT response elements was measured in response to stimulation by OKT3. NFAT signaling occurs downstream of the TCR signaling, and has been reported to correlate with other measures of T-cell activation, such as proliferation and cytokine release. Full blockade of PD-1/PD-L1 and/or TIGIT/CD155 interactions facilitated maximum TCR agonism and subsequent luciferase activity.

The activity of AZD2936 to block PD-1/PD-L1 interactions was tested in the two-cell co culture assay with CHO-K1 OKT3 PD-L1 CD155 cells and PD-1$^+$TIGIT$^-$ Jurkat T cell NFAT-luciferase reporter cells. AZD2936 showed a concentration-dependent activity in two duplicate experiments with a mean EC50 of 4.26 nM (EC50 of 4.70 and 3.83 nM from Experiment #1 and #2, respectively) (FIG. 10A and Table 9). In the same assay, the mean EC50 of anti-PD-1 were 3.03 nM (EC50 of 1.93 and 4.14 nM from Experiment #1 and #2, respectively). Neither anti-TIGIT antibody nor isotype control antibody showed activity in this assay.

The activity of AZD2936 to block TIGIT/CD155 interactions was tested. In this assay, CD155 aAPC/CHO-K1 cells were co cultured with Jurkat PD-1$^-$TIGIT$^+$ NFAT-luciferase reporter cells and the luciferase activities induced post the treatment of AZD2936, anti-TIGIT mAb, and an isotype control mAb were compared. In this assay, AZD2936 showed increased activity over the isotype control antibody with a mean EC50 of 15.3 nM from two experiments (EC50 of 17.0 nM and 13.7 nM in Experiment #1 and #2, respectively) (FIG. 10B and Table 10). In the same experiment, treatment of anti TIGIT resulted in a mean EC50 of 2.22 nM from two experiments (EC50 of 1.59 and 2.85 nM in Experiment #1 and #2, respectively).

The activity of AZD2936 to block PD-1/PD-L1 and TIGIT/CD155 interactions in an assay was tested with CHO-K1 OKT3 PD-L1 CD155 cells and PD-1$^+$TIGIT$^+$ Jurkat T cell NFAT-luciferase reporter cells. AZD2936 showed activity in two duplicate experiments with a mean EC50 of 5.82 nM (EC50 of 5.57 and 6.07 nM in two separate experiments) (FIG. 10C and Table 11).

TABLE 9

Bioactivity of AZD2936 and Anti-PD-1 Antibody in Human
PD-1⁺TIGIT⁻ Jurkat T Cell NFAT-Luciferase Reporter
Two-cell Co-culture Assays

| | Experiment #1 $EC_{50}$ (nM) | Experiment #2 $EC_{50}$ (nM) | Mean $EC_{50}$ (nM) | Fold Change of Mean $EC_{50}$ vs. Anti-PD-1 |
|---|---|---|---|---|
| AZD2936 | 4.70 | 3.83 | 4.26 | 1.40 |
| Anti-PD-1 | 1.93 | 4.14 | 3.03 | 1.00 |

$EC_{50}$ = half maximal effective concentration; NFAT = nuclear factor of activated T cells;
PD-1 = programmed cell-death protein 1; TIGIT = T cell immunoreceptor with Ig and
immunoreceptor tyrosine-based inhibitory motif domains.
$EC_{50}$ was derived from the mean values taken from 3 replicates.

TABLE 10

Bioactivity of AZD2936 and Anti-TIGIT Antibodies in Human
PD-1⁻TIGIT⁺ Jurkat T Cell NFAT-Luciferase Reporter
Two-cell Co-culture Assays

| | Experiment #1 $EC_{50}$ (nM) | Experiment #2 $EC_{50}$ (nM) | Mean $EC_{50}$ (nM) | Fold Change of Mean $EC_{50}$ vs. Anti-TIGIT |
|---|---|---|---|---|
| AZD2936 | 17.0 | 13.7 | 15.3 | 6.89 |
| Anti-TIGIT | 1.59 | 2.85 | 2.22 | 1.00 |

$EC_{50}$ = half maximal effective concentration; NFAT = nuclear factor of activated T cells;
PD-1 = programmed cell-death protein 1; TIGIT = T cell immunoreceptor with Ig and
immunoreceptor tyrosine-based inhibitory motif domains.
$EC_{50}$ was derived from the mean values taken from 3 replicates.

TABLE 11

Bioactivity of AZD2936 and the Combination of Anti-PD-1 and Anti-TIGIT
Antibodies in Human PD-1⁺TIGIT⁺ Jurkat T Cell NFAT-Luciferase Reporter
Two-cell Co-culture Assays

| | Experiment #1 $EC_{50}$ (nM) | Experiment #2 $EC_{50}$ (nM) | Mean $EC_{50}$ (nM) | Fold Change of Mean $EC_{50}$ vs. Anti-TIGIT and Anti-PD-1 combination |
|---|---|---|---|---|
| AZD2936 | 5.57 | 6.07 | 5.82 | 0.93 |
| Combination of Anti-TIGIT and Anti-PD-1 antibodies | 6.09 | 6.45 | 6.27 | 1.00 |

$EC_{50}$ = half maximal effective concentration; NFAT = nuclear factor of activated T cells; PD-1 = programmed
cell-death protein 1; TIGIT = T cell immunoreceptor with Ig and immunoreceptor tyrosine-based inhibitory motif
domains.
EC50 was derived from the mean values taken from 3 replicates

Example 4: OE21 Tumor Cell Killing Assay

The ability of AZD2936 to kill OE21 tumor cells was assessed in an in vitro assay system. Abbreviations used in this section are: ANOVA=analysis of variance; CMV=cytomegalovirus; EBV=Epstein Barr virus; ELISA=enzyme-linked immunosorbent assay; IFN-7=Interferon-γ; ns=not significant; OE21-VP=human Caucasian esophageal squamous cell carcinoma cell line engineered to express viral peptides (VP); PBMC=peripheral blood mononuclear cells; PD-1=programmed cell-death protein 1; TIGIT=T cell immunoreceptor with Ig and immunoreceptor tyrosine-based inhibitory motif domains.

HLA-Matched, Antigen-Specific T Cell and Tumor Cell Co-Culture System and Generation of OE21 Tumor Cell Lines Stably Expressing Viral Peptide Antigens A HLA-matched, antigen-specific T cell and tumor cell co-culture model was generated to evaluate the in vitro activity and potency of AZD2936 on T cell-mediated killing of tumor cells. The HLA-A*02:01 positive human oesophageal squamous cell carcinoma cell line, OE21, was engineered to express six viral antigen peptides known to bind HLA-A*02:01 (OE21-VP). The six viral peptides utilized were human Epstein Barr virus LMP2 356-364 peptide (amino acid sequence of FLYALALLL; SEQ ID NO:29), LMP2 426-434 (amino acid sequence of CLGGLLTMV; SEQ ID NO:30), BMLF1 280-288 (amino acid sequence GLCTLVAML; SEQ ID NO:31); Influenza M1 58-66 (amino acid sequence GILGFVFTL; SEQ ID NO:32), Influenza A PA46-54 (amino acid sequence FMYSDFHFI; SEQ ID NO:33); and Cytomegalovirus pp65 495-503 (amino acid sequence NLVPMVATV; SEQ ID NO:34). The transgene encoding viral peptides and GFP reporter cassettes driven from the constitutive human ubiquitin-C promoter were generated by gene synthesis (GeneArt™, Pleasanton, CA). Transgenes were inserted into lentiviral expression vectors using standard molecular biology techniques. Sequence-verified transgene constructs were then used to generate lentiviral particles from a HEK293FT (Life Technologies, Grand Island, NY) producer cell line using the pPACKH1 HIV Lentivector Packaging Kit (Systems Bioscience, Palo Alto, CA) as per the manufacturer's instructions. Single cell transgene-overexpressing clonal lines were selected by fluorescence-activated cell sorting (FACS) to isolate GFP+ cells, and cell lines exhibiting uniform transgene expression profiles were banked and progressed for further characterization.

Expansion of GLCTLVAML (SEQ ID NO:31) and NLVPMVATV (SEQ ID NO:34) Peptide Specific T Cells from HLA-A*02:01 Positive Healthy Donors Peripheral blood mononuclear cells (PBMC) from HLA-A*02:01 positive heathy donors were screened for reactivity to EBV BMLF1 280-288 peptide (GLCTLVAML) and CMV pp65 495-503 peptide (NLVPMVATV) using flow cytometry for activation markers. Briefly, PBMC were treated with 1 pg/mL peptide and 55 international unit (IU)/mL IL-2 for seven days, subsequently stained with a fluorescently conjugated CD3, CD8, CD25, and TIM3 antibodies and evaluated by flow cytometry for binding. The donors were identified as EBV or CMV reactive if >10% CD3+CD8+ T cells stain positively for both CD25 and TIM-3. PBMC reactive to the EBV BMLF1 280-288 peptide or CMV pp65 495-503 peptide were isolated from healthy donor (HLA A*02:01 positive) blood using a RoboSep™-S automated cell separator (StemCell Technologies, Cambridge, MA) in combination with an EasySep™ Direct Human PBMC isolation kit (StemCell Technologies), as per the manufacturer's instructions. As shown in FIG. 1B, isolated PBMC were then resuspended at $1.5 \times 10^7$ cells/mL in a 1:1 mixture of complete RPMI culture media containing RPMI-1640™ (Gibco) and AIM-V™ media (Gibco), 5% HI human serum (Sigma Aldrich), 100 U/mL penicillin (Gibco), and 100 µg/mL streptomycin (Gibco), in the presence of 1 µg/mL peptide (MBL International Corporation) and 55 IU/mL recombinant human IL-2 (PeproTech) for half an hour before subsequent culture in a G-Rex6® Well Plate (Wilson Wolf Corporation) at 40 mL IL-2 media per well for 7 days at 37° C., 5% $CO_2$ prior to analysis.

Analysis of GLCTLVAML (SEQ ID NO:31) and NLVPMVATV (SEQ ID NO:34) Peptide-Specific CD8+ T Cells Expanded PBMC were analyzed by flow cytometry using a LSR II® instrument (BD Biosciences) to quantify antigen-specific CD8+ T cells. After expansion, PBMC were washed with FACS Buffer (PBS pH 7.2 (Gibco), 2% FBS (Gibco), and 2 mM EDTA (Gibco)) and incubated with fluorescently labeled HLA-A*02:01/GLCTLVAML or HLA-A*02:01/NLVPMVATV dextramer (ImmuDex™) for 30 minutes at room temperature. PBMC were additionally co-stained with fluorescently labeled anti-CD3 (clone HIT3a, Biolegend), anti-CD8 (clone HIT8A, Biolegend), anti-PD-1 (clone EH12.2H7, Biolegend), and anti-TIGIT (clone A15153G, Biolegend™) to distinguish different cell populations. After washing twice with FACS buffer, cells were analyzed for detection of bound antibodies by flow cytometry. The number of antibodies bound to the cell surface was detected using FACSDiva™ software (BD Biosciences). Data analysis was performed using the FlowJo™ software (BD Biosciences). The percentage of antigen-specific CD8+ T cells (gated based on singlet, no debris, CD3+, CD8+ and positive for GLCTLVAML or NLVPMVATV dextramer) following expansion was determined using the formula:

$$\text{Total number of antigen–specific } CD8 + T \text{ cells} = A \times (B/100);$$

Where A is the total number of cells collected, and B is the % of Singlet, Minus Debris, CD3+CD8+ T cells that are dextramer positive.

T-Cell Killing Assay

A co-culture assay system was developed to measure the ability of AZD2936 to modify antigen-specific CD8+ T cell killing of tumor cells. Tumor cell lysis was evaluated utilizing the Agilent xCELLigence RTCA® platform, whereby loss of cellular impedance was used as a surrogate for tumor cell death (Oberg et al., Front Immunol. 2014; 5:643). Briefly, OE21-VP cells were harvested from cell culture flasks using trypsin, washed once with complete RPMI™ culture medium, resuspended in complete RPMI™ medium, and added to each well of 96-well RTCA E-Plates® at 10,000 cells per well. The tumor cells were cultured in E-Plates® for 24 hours at 37° C. in 5% $CO_2$ as per the manufacturer's instructions. Test and control articles were added to wells immediately before peptide specific CD8+ T cells were added at optimized effector to target (E:T) ratios, which were pre-determined for each donor CD8+ T cell population utilized in this study (at a 2:1 effector T cells to tumor target ratio). Tumor cell death and percent cytolysis were monitored over a range of 3-8 days after T cell addition (donor-dependent), and values calculated using RTCA Pro® software as per the manufacturer's instructions.

Analysis of EC50 Values

Loss of cellular impedance was calculated on RTCA PRO® software (Agilent), which measured real-time cellular impedance as a marker of tumor cell killing. The area under the curve for real-time cytolysis (Cytolysis*Hours) was determined and plotted to calculate the EC50 values in Prism Software® (GraphPad Software, San Diego, CA) for test and control article co-cultures at concentrations ranging from 0.0001 nM to 10 nM as compared to T cell co-cultures without inclusion of test or control articles alone (baseline effect). Impedance was continuously measured every 10 minutes until completion of the study, which occurred 6 days after T cell addition.

Measurement of IFN-γ Concentrations in Co-Culture Supernatants

To evaluate the amount of IFN-γ detected within the supernatants of co-cultures containing OE21-VP tumor cells and tumor reactive CD8+ T cells, separate parallel co-cultures were established in Nunc 96 well plates (Sigma Aldrich) alongside xCELLigence® RTCA E-Plates®. For evaluation of IFN-γ release, supernatants were harvested from co-cultures in the Nunc 96 well plates twenty four hours later. Comparison of IFN-γ levels was evaluated at the 200 pM concentration of test and control articles. IFN-γ was measured using Mesoscale Discovery multi-spot ELISA for human IFN-γ as per the manufacturer's instructions.

Statistical Methods

For cytolysis and IFN-γ release, statistical analysis was performed in Prism®, version 8.0.1 for Windows® (GraphPad Software, San Diego, CA). One-Way ANOVA, Assuming Sphericity (equal variability of differences), Tukey's multiple comparison tests were performed. EC50 values were modeled with a nonlinear fit curve using logarithmic dose versus normalized response. For evaluation of differences in EC50 values between AZD2936 and anti-PD-1 treatment groups, EC50 values were log-transformed, group means were compared using a two-sided unpaired student's t-test and evaluated assuming unequal variances for the two groups. p-values are presented in each figure as non-significant (ns) $p > 0.05$, $*p < 0.05$, $p < 0.01$, $*p < 0.001$, $****p < 0.0001$.

CD8 positive T cells were collected and pooled from five healthy human donors. Primary human PBMC expanded with the EBV or CMV peptide were co-cultured with test and control articles (0.2 nM isotype control, 0.2 nM anti-PD-1, 0.2 nM anti-TIGIT, 0.1 nM anti-PD-1+0.1 nM anti-TIGIT, or 0.2 nM AZD2936) and OE21-VP tumor cells.

Figure 11:
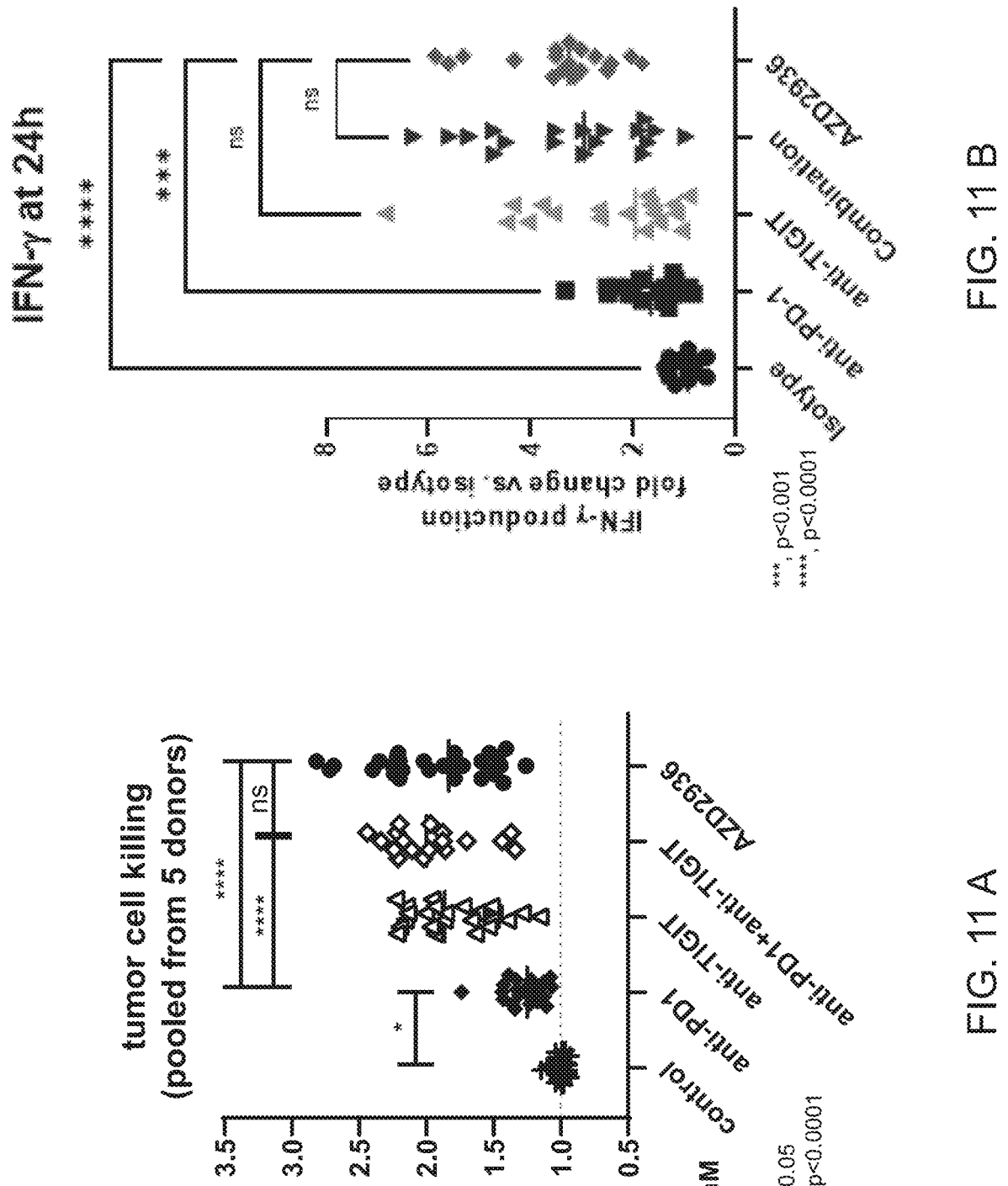
FIGS. 11A-11D show the cell killing activity of AZD2936 and stimulation of IFN-γ release in a cell killing assay as described in Example 4.

FIG. 11A shows that AZD2936 had increased activity over anti-PD-1 in this CD8 T cell-mediated in vitro cell killing assay. As shown in FIG. 11A, AZD2936 shows a significant improvement in OE21-VP tumor cell killing compared with administration of anti-PD1 antibody alone.

Upon antigen recognition, CD8+ T cells secrete IFN-γ, a cytokine which further promotes anti-tumor immunity and CD8+ T cell cytotoxic effects (Bhat et al Cell Death Dis., 2017 Jun. 1; 8(6):e2836). Thus, IFN-γ release was evaluated following peptide-specific CD8+ T cell co culture with OE21-VP cells.

Primary human PBMC expanded with the EBV or CMV peptide were co-cultured with test and control articles (0.2 nM isotype control, 0.2 nM anti-PD-1, 0.2 nM anti-TIGIT, 0.1 nM anti-PD-1+0.1 nM anti-TIGIT, or 0.2 nM AZD2936) and OE21-VP tumor cells. The concentration of IFN-γ of the T cell and tumor cell co culture assay was measured from supernatants collected twenty four hours after T cell addition. Results are shown in FIG. 11B. The concentration of IFN-γ was determined using Mesoscale Discovery multi-spot ELISA for human IFN-γ. Fold change of all values compared to an average for the isotype control are reported. The data represents 4 distinct donors. Statistical significance was calculated using one-way ANOVA and Tukey's multiple comparison test. Horizontal lines represent intragroup arithmetic mean values. *, $p < 0.001$, **, $p < 0.0001$.

As shown in FIG. 11B, in co-cultures of T cells isolated and expanded from the PBMC of four healthy donors, AZD2936 induced a statistically significantly increased amount of IFN-γ in the supernatant of co-cultures with tumor cells compared to isotype control and anti-PD-1.

Figures 11C, 11D:
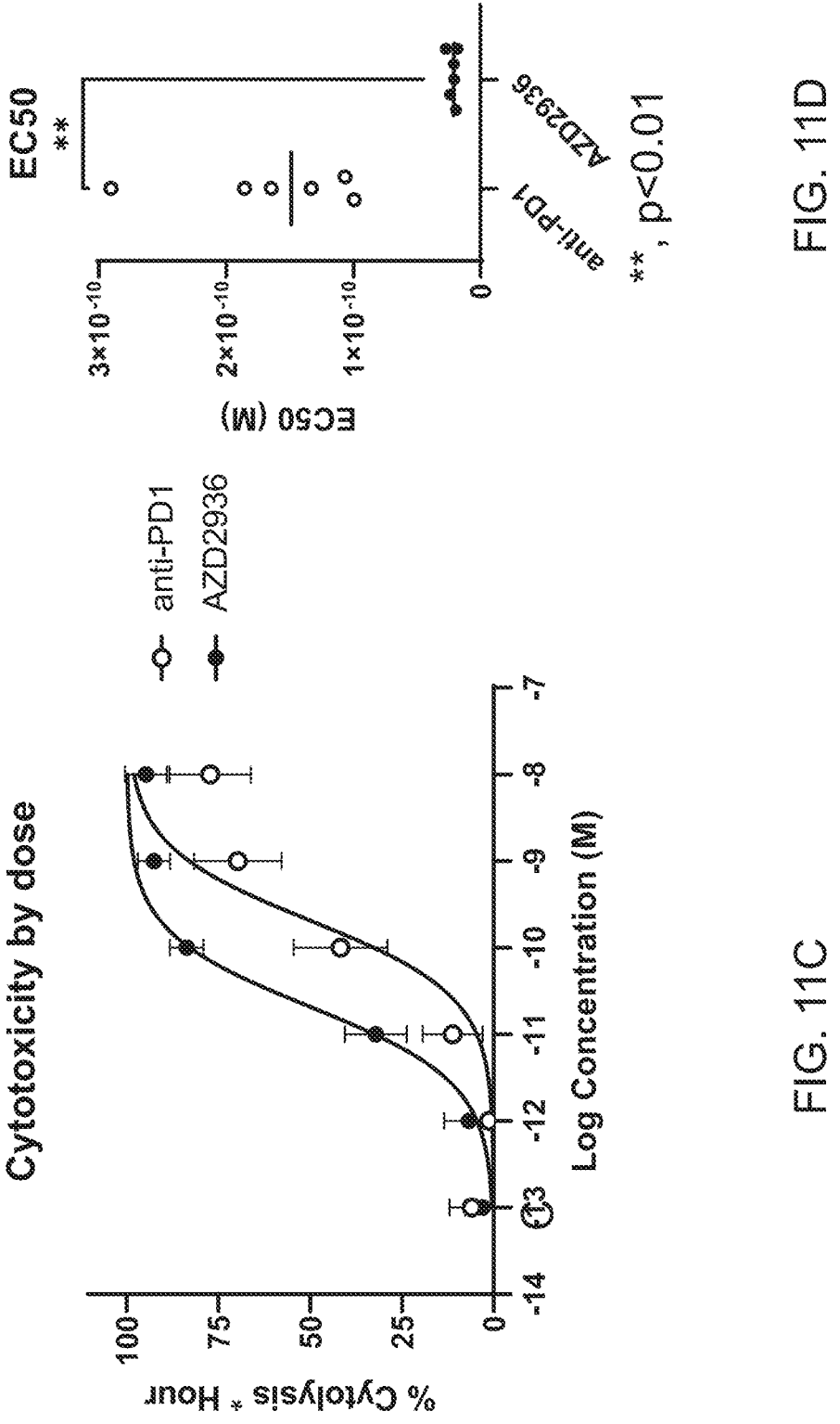
Figures 12A, 12B:
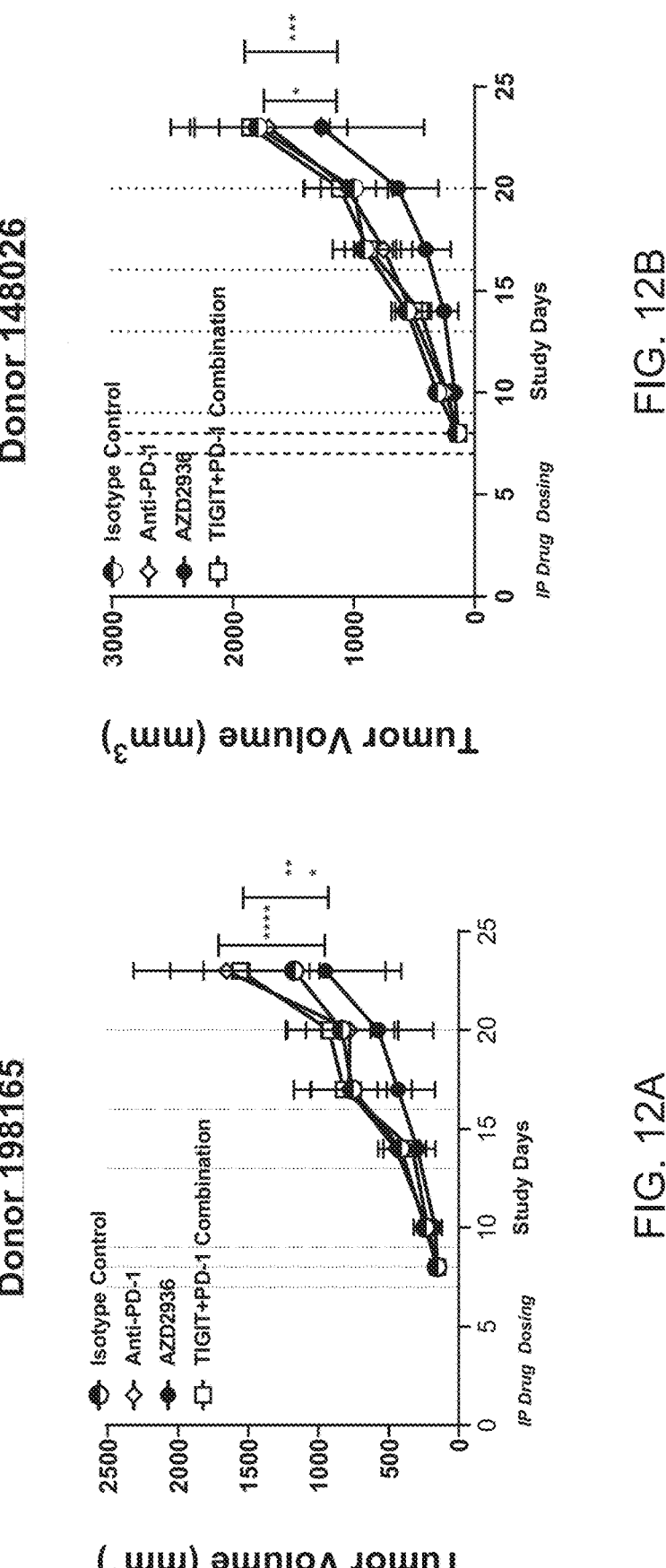
FIGS. 12A-12D shows that AZD2936 had a stronger anti-tumor activity than anti-PD-1 in the OE21 tumor model. Dotted vertical lines in 12A and 12B show intraperitoneal injection (IP) drug dosing.
Figures 12C, 12D:
Figures 13A, 13B:
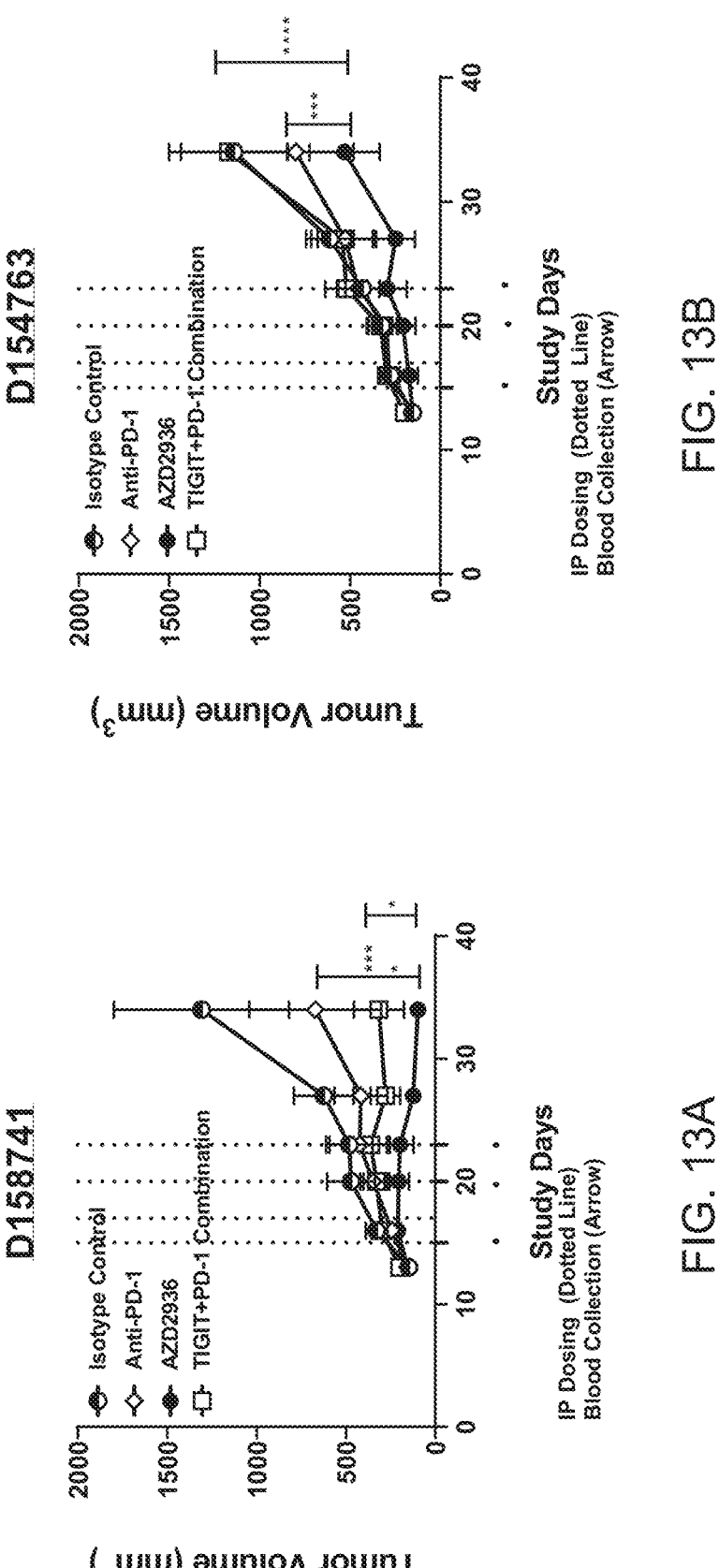
FIGS. 13A-13D shows that AZD2936 had a greater anti-tumor activity than anti-PD-1 in the PC9-MART1 tumor model. Dotted vertical lines in 13A and 13B show intraperitoneal injection (IP) drug dosing.
Figures 13C, 13D:
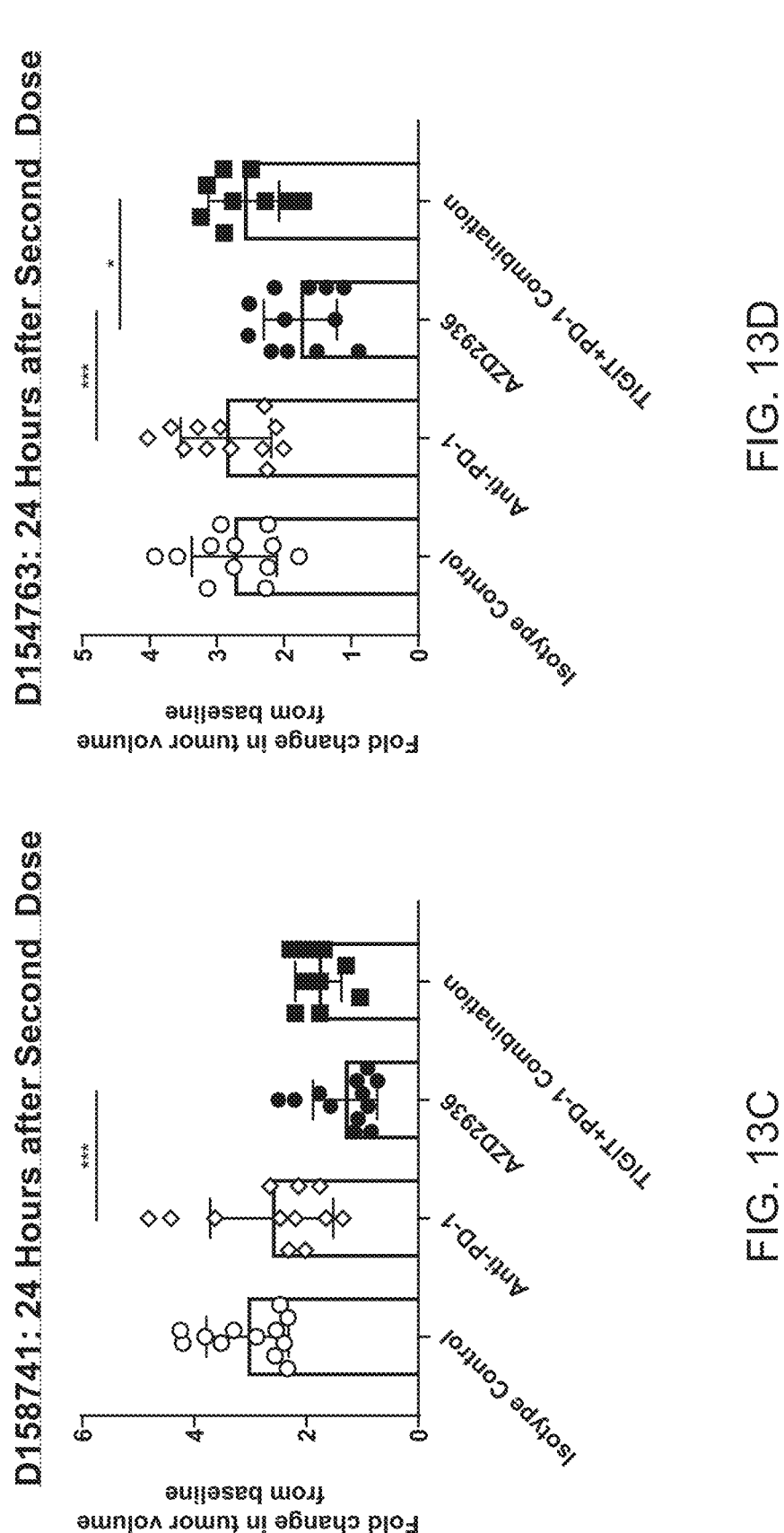

The in vitro cell killing assay was also used to determine the difference in cytotoxicity between AZD2936 and anti-PD-1 antibody. A concentration titration of antibodies from 10 nM to 0.1 pM showed the arithmetic mean EC50 for AZD2936 was 21.9±3.4 pM (SD) and 163±70.6 pM (SD) for anti PD 1 (FIG. 11D), yielding a 6.44-fold increase in potency of AZD2936 in comparison to anti-PD-1 (FIG. 11C).

Example 5: OE21 and PC9-MART1 Human Xenograft Tumor Mouse Models

The OE21 tumor model and the PC9-MART1 tumor model (FIGS. 12A-12D, and 13A-13D, respectively) were used to investigate AZD2936's ability to inhibit tumor growth. The activity of AZD2936 was investigated in human tumor xenograft mouse models using immunodeficient nonobese diabetic/severe combined immunodeficiency (NOD-scid) IL-2 receptor gamma null (NSG) mice. Animals were inoculated subcutaneously with human cancerous cell lines engineered to express peptide antigens presented by HLA-A*2:01. One model utilized OE21-VP, an esophageal carcinoma cell line engineered to express viral peptides. Another model utilized PC9-MART1, a lung adenocarcinoma cell line engineered to express a melanoma antigen-1.

Tumor cell lines were injected in the flank of mice by subcutaneous (SC) injection and after tumors grew in volume to approximately 200 mm³, each mouse received an IV injection of human T cells specific for antigens expressed by the tumor cell lines. Animals received the first dose of the test and control articles within 24 hours after randomization, and were subsequently administered three additional doses of the test and control articles.

Intraperitoneal administration of AZD2936 to animals significantly inhibited the growth of tumors as compared to the activity of its parental bivalent anti-PD-1 antibody (Anti PD-1), Anti-TIGIT and Anti-PD-1 combination and a bivalent isotype control antibody targeting an irrelevant antigen, R347 (Isotype Control) as shown in FIGS. 12A-12D, and 13A-13D. AZD2936 treatment inhibited tumor growth for the entire duration of the studies and in two xenograft mouse models utilizing T cells with different antigen specificities. Antitumor activity of AZD2936 occurred utilizing tumor-specific T cells derived from two independent, healthy donors each for the OE21-VP and the PC9-MART-1 models.

Example 6: Characterization of Effector Function for AZD2936

Therapeutic antibodies rely on two types of functionalities to exert clinical efficacy: target specific binding by the Fab domain and immune-mediated effector functions via interaction of the Fc domain. When IgG antibodies bind cell surface antigens via their Fab domains, the Fc portion of the antibodies can bind to complement component 1q (C1q), the first member of the antibody triggered classical complement pathway or can engage with Fc gamma receptors (FcγRs) expressed on natural killer and other myeloid cells.

The interaction with C1q initiates the complement cascade, resulting in the formation of membrane attack complex that kills the target cell by disrupting its cell membrane, a process described as complement-dependent cytotoxicity (CDC). The interaction of the Fc domain of an antibody with FcγRIIIa induces cross-linking of the FcγRs, which triggers the release of cytotoxic granules containing perforin and granzymes, leading to the death of the target cell bound by the antigen binding domain of the antibody, a process called antibody-dependent cellular cytotoxicity (ADCC) (Nimmerjahn and Ravetch, Nature Reviews Immunology, 8:34-47, 2008). AZD2936 is a monovalent, bispecific, humanized, IgG1 monoclonal antibody engineered to have mutations within its Fc domain to diminish Fc-mediated effector functionality. These Fc mutations are a triple mutation L234F/L235E/P331S. The potential of AZD2936 to initiate CDC and ADCC activity was evaluated utilizing a Jurkat cell line engineered to express TIGIT and PD-1.

Figure 14A:
FIGS. 14A-14B show the percentage of live, PD-1 and TIGIT expressing Jurkat cells (FIG. 14A) or Daudi cells (FIG. 14B) following incubation with AZD2936, IgG1-TM isotype control, rituximab, or IgG1 isotype control, together with complement containing human serum or heat-inactivated human serum as described in Example 6. Error bars represent SD (n=2).
Figure 14A:
Figure 14A:
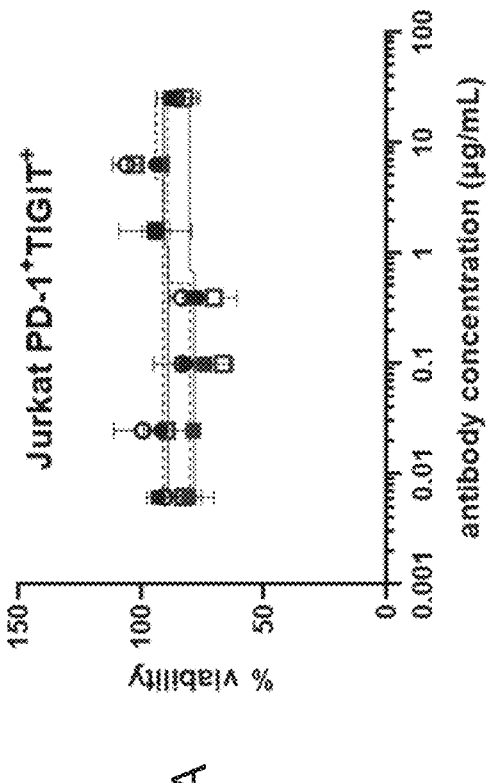
Figure 14B:
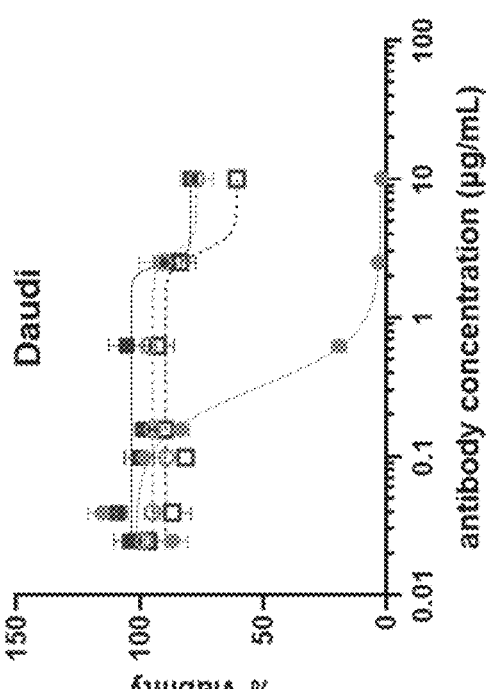

The percentage of live, PD-1 and TIGIT expressing Jurkat cells (FIG. 14A) or Daudi cells (FIG. 14B) following incubation with AZD2936, IgG1-TM isotype control, rituximab, or IgG1 isotype control, together with complement containing human serum or heat-inactivated human serum was estimated by addition of Cell-Titer Glo®. Cell-Titer Glo® produces a luminescent signal proportional to the number of live cells in each well. These results show that AZD2936 did not trigger CDC in the Jurkat PD-1⁺TIGIT⁺ cells (FIG. 14A). Conversely, rituximab, an anti-CD20 antibody known to have CDC activity, demonstrated concentration-dependent effects on CD20 expressing Daudi cells in the presence of the same human serum used in the assay with AZD2936, but not in the presence of a heat-inactivated serum control (FIG. 14B). IgG1 isotype control did not have any effect on the percentage of viable cells for either cell type. No sample using heat-inactivated serum resulted in a concentration-dependent decrease in viability, confirming that the observed cell death was mediated by CDC.

Figure 15:
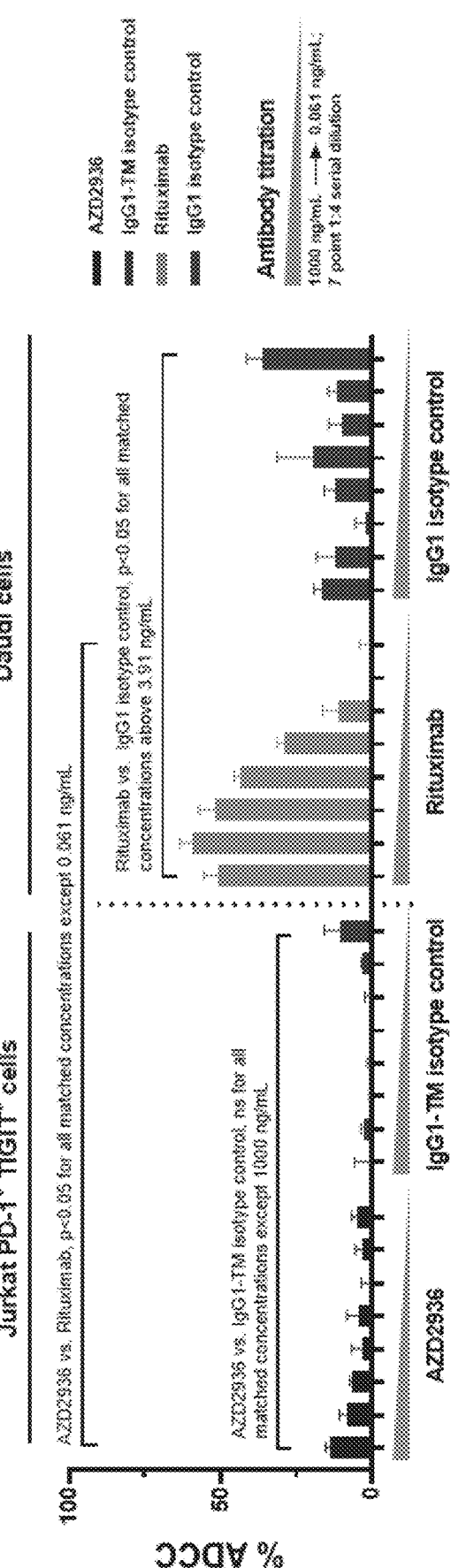
FIG. 15 shows the specific killing of Jurkat cells expressing PD-1 and TIGIT or Daudi cells by primary human PBMC. Concentration-dependent ADCC was mediated by Rituximab but not IgG1 isotype control, AZD2936, or IgG1™ isotype control as described in Example 6. Error bars represent SD (n=2).

Antibody-dependent cellular cytotoxicity (ADCC) activity was evaluated utilizing PBMC from healthy donors as the effector cells and a PD-1 and TIGIT expressing Jurkat cell line as the target cell. In this assay, AZD2936 demonstrated similar activity as the isotype control samples, and yielded a statistically significant reduction in ADCC activity compared to the positive control, rituximab using CD20 expressing Daudi cells as the target cell, at all matched concentrations above 0.061 ng/mL (FIG. 15). The results of this study show AZD2936 did not trigger ADCC or CDC against a PD-1 and TIGIT expressing Jurkat cell line.

50

What is claimed is:

1. A bispecific binding protein that specifically binds to PD-1 and TIGIT comprising:

a) a first binding domain that specifically binds to PD-1, wherein the first binding domain comprises a heavy chain variable domain comprising a HCDR1 comprising the amino acid sequence of SEQ ID NO: 1, a HCDR2 comprising the amino acid sequence of SEQ ID NO: 2, and a HCDR3 comprising the amino acid sequence of SEQ ID NO: 3, and a light chain variable domain comprising a LCDR1 comprising the amino acid sequence of SEQ ID NO: 4, a LCDR2 comprising the amino acid sequence of SEQ ID NO: 5 and a LCDR3 comprising the amino acid sequence of SEQ ID NO: 6; and b) a second binding domain that specifically binds to TIGIT, wherein the second binding domain comprises a heavy chain variable domain comprising a HCDR1 comprising the amino acid sequence of SEQ ID NO: 11, a HCDR2 comprising the amino acid sequence of SEQ ID NO: 12, and a HCDR3 comprising the amino acid sequence of SEQ ID NO: 13, and a light chain variable domain comprising a LCDR1 comprising the amino acid sequence of SEQ ID NO: 14, a LCDR2 comprising the amino acid sequence of SEQ ID NO: 15, and a LCDR3 comprising the amino acid sequence of SEQ ID NO: 16;

wherein first binding domain that specifically binds to PD-1 comprises a heavy chain variable domain comprising an amino acid sequence that is at least 90% identical to the amino acid sequence of SEQ ID NO: 7 and a light chain variable domain comprising an amino acid sequence that is at least 90% identical to the amino acid sequence of SEQ ID NO: 9; and wherein the second binding domain that specifically binds to TIGIT comprises a heavy chain variable domain comprising an amino acid sequence that is at least 90% identical to the amino acid sequence of SEQ ID NO: 17 and a light chain variable domain comprising an amino acid sequence that is at least 90% identical to the amino acid sequence of SEQ ID NO: 19.

2. The bispecific binding protein of claim 1, wherein first binding domain that specifically binds to PD-1 comprises a heavy chain comprising an amino acid sequence that is at least 90% identical to the amino acid sequence of SEQ ID NO: 8 and a light chain comprising an amino acid sequence that is at least 90% identical to the amino acid sequence of SEQ ID NO: 10.

3. The bispecific binding protein of claim 2, wherein the second binding domain that specifically binds to TIGIT comprises a heavy chain comprising an amino acid sequence that is at least 90% identical to the amino acid sequence of SEQ ID NO: 18 and a light chain comprising an amino acid sequence that is at least 90% identical to the amino acid sequence of SEQ ID NO: 20.

4. The bispecific binding protein of claim 1, wherein the bispecific binding protein is an IgG1 antibody and comprises a L234F/L235E/P331S triple mutation (TM).

5. The bispecific binding protein of claim 1, wherein the equilibrium dissociation constant ($K_D$) of the bispecific binding protein—human TIGIT interaction is from about 9 pM to about 15 pM.

6. The bispecific binding protein of claim 5, wherein the equilibrium dissociation constant ($K_D$) of the bispecific binding protein—human PD-L1 interaction is from about 0.3 nM to about 0.5 nM.

7. The bispecific binding protein of claim 1, comprising a variant Fc region wherein the variant Fc region comprises at least one substitution selected from 221K, 221Y, 225E, 225K, 225W, 228P, 234D, 234E, 234N, 234Q, 234T, 234H, 234Y, 234I, 234V, 234F, 235A, 235D, 235R, 235W, 235P, 235S, 235N, 235Q, 235T, 235H, 235Y, 235I, 235V, 235E, 235F, 236E, 237L, 237M, 237P, 239D, 239E, 239N, 239Q, 239F, 239T, 239H, 239Y, 240I, 240A, 240T, 240M, 241W, 241L, 241Y, 241E, 241R, 243W, 243L, 243Y, 243R, 243Q, 244H, 245A, 247L, 247V, 247G, 250E, 250Q, 251F, 252L, 252Y, 254S, 254T, 255L, 256E, 256F, 256M, 257C, 257M, 257N, 262I, 262A, 262T, 262E, 263I, 263A, 263T, 263M, 264L, 264I, 264W, 264T, 264R, 264F, 264M, 264Y, 264E, 265A, 265G, 265N, 265Q, 265Y, 265F, 265V, 265I, 265L, 265H, 265T, 266I, 266A, 266T, 266M, 267Q, 267L, 268E, 269H, 269Y, 269F, 269R, 270E, 280A, 284M, 292P, 292L, 296E, 296Q, 296D, 296N, 296S, 296T, 296L, 296I, 296H, 296G, 297S, 297D, 297E, 298A, 298H, 298I, 298T, 298F, 299I, 299L, 299A, 299S, 299V, 299H, 299F, 299E, 305I, 308F, 313F, 316D, 318A, 318S, 320A, 320S, 322A, 322S, 325Q, 325L, 325I, 325D, 325E, 325A, 325T, 325V, 325H, 326A, 326D, 326E, 326G, 326M, 326V, 327G, 327W, 327N, 327L, 328S, 328M, 328D, 328E, 328N, 328Q, 328F, 328I, 328V, 328T, 328H, 328A, 329F, 329H, 329Q, 330K, 330G, 330T, 330C, 330L, 330Y, 330V, 330I, 330F, 330R, 330H, 331G, 331A, 331L, 331M, 331F, 331W, 331K, 331Q, 331E, 331S, 331V, 331I, 331C, 331Y, 331H, 331R, 331N, 331D, 331T, 332D, 332S, 332W, 332F, 332E, 332N, 332Q, 332T, 332H, 332Y, 332A, 333A, 333D, 333G, 333Q, 333S, 333V, 334A, 334E, 334H, 334L, 334M, 334Q, 334V, 334Y, 339T, 370E, 370N, 378D, 392T, 396L, 416G, 419H, 421K, 428L, 428F, 433K, 433L, 434A, 434W, 434Y, 436H, 440Y and 443W as numbered by the EU index as set forth in Kabat.

8. The bispecific binding protein of claim 7, wherein the variant Fc region comprises a M252Y/S254T/T256E (YTE) mutation.

9. The bispecific binding protein of claim 7, wherein the Fc variant region comprises a L234F/L235E/P331S triple mutation (TM).

10. The bispecific binding protein of claim 1, comprising an Fc region, wherein the Fc region has reduced fucosylation or is afucosylated.

11. A pharmaceutical composition comprising bispecific binding protein of claim 1, and a pharmaceutically acceptable carrier.

12. The pharmaceutical composition of claim 11, further comprising an anti-cancer compound selected from pemetrexed, carboplatin, gemcitabine, cisplatin, paclitaxel or combinations thereof.

13. A nucleic acid comprising a nucleotide sequence encoding the bispecific binding protein of claim 1.

14. A vector comprising the nucleic acid of claim 13.

15. A host cell comprising the vector of claim 14.

16. A method of treating cancer in a subject, the method comprising administering to the subject a therapeutically effective amount of the nucleic acid of claim 13.

17. A method of treating cancer in a subject, the method comprising administering to the subject the bispecific binding protein of claim 1.

18. The method of claim 17, wherein the cancer is one or more of ovarian cancer, breast cancer, colorectal cancer, prostate cancer, cervical cancer, uterine cancer, testicular cancer, bladder cancer, head and neck cancer, melanoma, pancreatic cancer, renal cell carcinoma, lung cancer, or non-small cell lung cancer (NSCLC).

19. A method of treating cancer in a subject, the method comprising administering to the subject a therapeutically effective amount of the bispecific binding protein of claim 1 in combination with an anti-cancer compound selected from pemetrexed, carboplatin, gemcitabine, cisplatin, paclitaxel or combinations thereof.

20. A method of treating cancer in a subject, the method comprising administering the nucleic acid of claim 13 in combination with an anti-cancer compound selected from pemetrexed, carboplatin, gemcitabine, cisplatin, paclitaxel or combinations thereof.

* * * * *